(12) United States Patent
Hassan et al.

(10) Patent No.: US 11,806,371 B2
(45) Date of Patent: Nov. 7, 2023

(54) OXALOBACTER FORMIGENES (OF)-DERIVED FACTORS FOR THE TREATMENT OF TREATMENT/PREVENTION OF EXCESS OXALATE LEVELS

(71) Applicant: The University of Chicago, Chicago, IL (US)

(72) Inventors: Hatim A. Hassan, Chicago Ridge, IL (US); Donna Arvans, Chicago, IL (US)

(73) Assignee: The University of Chicago, Chicago, IL (US)

( * ) Notice: Subject to any disclaimer, the term of this patent is extended or adjusted under 35 U.S.C. 154(b) by 31 days.

(21) Appl. No.: 16/479,516

(22) PCT Filed: Jan. 19, 2018

(86) PCT No.: PCT/US2018/014494
§ 371 (c)(1),
(2) Date: Jul. 19, 2019

(87) PCT Pub. No.: WO2018/136779
PCT Pub. Date: Jul. 26, 2018

(65) Prior Publication Data
US 2020/0188451 A1 Jun. 18, 2020

Related U.S. Application Data

(60) Provisional application No. 62/448,178, filed on Jan. 19, 2017.

(51) Int. Cl.
*A61K 35/741* (2015.01)
*A61K 38/16* (2006.01)
*C07K 14/21* (2006.01)
*A61K 35/00* (2006.01)

(52) U.S. Cl.
CPC .......... *A61K 35/741* (2013.01); *A61K 38/164* (2013.01); *C07K 14/21* (2013.01); *A61K 2035/115* (2013.01)

(58) Field of Classification Search
None
See application file for complete search history.

(56) References Cited

U.S. PATENT DOCUMENTS 5,359,030 A 10/1994 Ekwuribe et al.
5,681,811 A 10/1997 Ekwuribe et al.
6,552,167 B1 4/2003 Rose

OTHER PUBLICATIONS

Arvans et al. J. Am. Soc. Nephrol. 28: 876-887, Oct. 13, 2016.*
Arvans et al. J. Am. Soc. Nephrol. 28: 876-887, published online Oct. 13, 2016.*
Allison et al. Arch. Microbiol. 141: 1-7, 1985.*
Hatch et al. Kidney International, 69: 691-698, 2006.*
Lazar et al. Mol. Cellular Biol. 8: 1247-1252, 1988.*
Alexander et al., Kidney stones and kidney function loss: a cohort study. BMJ. Aug. 29, 2012;345:e5287.
Allison et al., Oxalobacter formigenes gen. nov., sp. nov.: oxalate-degrading anaerobes that inhabit the gastrointestinal tract. Arch Microbiol. Feb. 1985;141(1):1-7.
Allmendinger et al., Fluoroolefin dipeptide isosteres—I.: The synthesis of GlyY(CF=CH)Gly and Racemk PheY(CF&H)Gly. Tetrahydron Lett. 1990; 31, 7297.
Amin et al., Extracellular Nucleotides Inhibit Oxalate Transport by Human Intestinal Caco2-BBE Cells Through PKC-delta Activation. Am J Physiol Cell Physiol. Jul. 1, 2013;305(1):C78-89.
Borthakur et al., The probiotic Lactobacillus acidophilus stimulates chloride/hydroxyl exchange activity in human intestinal epithelial cells. J Nutr. Jul. 2008;138(7):1355-9.
Caudarella et al., Renal stone formation in patients with inflammatory bowel disease. Scanning Microsc. Mar. 1993;7(1):371-9; discussion 379-80.
Chorev et al., A dozen years of retro-inverso peptidomimetics. Acc. Chem. Res, 1993; 26:266-73.
Coe et al., Kidney stone disease. J Clin Invest. Oct. 2005;115(10):2598-608.
Daniel et al., Microbial degradation of oxalate in the gastrointestinal tracts of rats. Appl Environ Microbiol. Aug. 1987;53(8):1793-7.
Danpure et al., Peroxisomal alanine:glyoxylate aminotransferase deficiency in primary hyperoxaluria type 1. FEBS Lett. May 26, 1986;201(1):20-4.
Dawson et al., Urolithiasis and hepatotoxicity are linked to the anion transporter Sat1 in mice. J Clin Invest. Mar. 2010;120(3):706-12.
Delgado et al., The uses and properties of PEG-linked proteins. Crit Rev Ther Drug Carrier Syst. 1992;9(3-4):249-304.
Eisner et al., Diabetic kidney stone formers excrete more oxalate and have lower urine pH than nondiabetic stone formers. J Urol. Jun. 2010;183(6):2244-8.
Ellis et al., Proteome Dynamics of the Specialist Oxalate degrader. J Proteomics Bioinform. 2016;9(1):19-24.
Francis et al., PEGylation of cytokines and other therapeutic proteins and peptides: the importance of biological optimisation of coupling techniques. Int J Hematol. Jul. 1998;68(1):1-18.
Freel et al., Parsing apical oxalate exchange in Caco-2BBe1 monolayers: siRNA knockdown of SLC26A6 reveals the role and properties of PAT-1. Am J Physiol Gastrointest Liver Physiol. Nov. 2009;297(5):G918-29.
Gombotz et al., Biodegradable polymers for protein and peptide drug delivery. Bioconjug Chem. Jul.-Aug. 1995;6(4):332-51.
Hassan et al., Cholinergic signaling inhibits oxalate transport by human intestinal T84 cells. Am J Physiol Cell Physiol. Jan. 1, 2012;302(1):C46-58.

(Continued)

*Primary Examiner* — S. Devi
(74) *Attorney, Agent, or Firm* — Casimir Jones, S.C.; David W. Staple

(57) ABSTRACT

Provided herein are compositions comprising *Oxalobacter formigenes* (Of)-derived factors and variants and fragments thereof, and method of use thereof for the treatment/prevention excess oxalate levels and conditions and diseases related thereto.

4 Claims, 6 Drawing Sheets

Specification includes a Sequence Listing.

(56) References Cited

OTHER PUBLICATIONS

Hatch et al., A human strain of Oxalobacter (HC-1) promotes enteric oxalate secretion in the small intestine of mice and reduces urinary oxalate excretion. Urolithiasis. Oct. 2013;41(5):379-84.
Hatch et al., Enteric oxalate elimination is induced and oxalate is normalized in a mouse model of primary hyperoxaluria following intestinal colonization with Oxalobacter. Am J Physiol Gastrointest Liver Physiol. Mar. 2011;300(3):G461-9.
Hatch et al., Intestinal transport of an obdurate anion: oxalate. Urol Res. Feb. 2005;33(1):1-16.
Hoffman et al., The stereoselective synthesis of 2-alkyl. gamma.-keto acid and heterocyclic ketomethylene peptide isostere core units using chiral alkylation by 2-triflyloxy esters. O. J. Org. Chem., 1995;60:5107-5113.
Hoppe et al., Oxalate degrading bacteria: new treatment option for patients with primary and secondary hyperoxaluria? Urol Res. Nov. 2005;33(5):372-5.
Hoppe et al., Oxalobacter formigenes: a potential tool for the treatment of primary hyperoxaluria type 1. Kidney Int. Oct. 2006;70(7):1305-11.
Jiang et al., Calcium oxalate urolithiasis in mice lacking anion transporter Slc26a6. Nat Genet. Apr. 2006;38(4):474-8.
Jiang et al., Specificity of anion exchange mediated by mouse Slc26a6. J Biol Chem. Sep. 13, 2002;277(37):33963-7.
Langmead et al., Ultrafast and memory-efficient alignment of short DNA sequences to the human genome. Genome Biol. 2009;10(3):R25.
Lavielle et al., Importance of the leucine side-chain to the spasmogenic activity and binding of substance P analogues.Int J Pept Protein Res. Sep. 1993;42(3):270-7.
Love et al., Moderated estimation of fold change and dispersion for RNA-seq data with DESeq2. Genome Biol. 2014;15(12):550.
Luisi et al., ψ(SO2—NH) transition state isosteres of peptides. Synthesis of the glutathione disulfide analogue. Tetrahedron Lett. 1993; 34(14): 2391-2392.
Mittl et al., Sel1-like repeat proteins in signal transduction. Cell Signal. Jan. 2007;19(1):20-31.

Nelson et al., Enteric hyperoxaluria, nephrolithiasis, and oxalate nephropathy: potentially serious and unappreciated complications of Roux-en-Y gastric bypass. Surg Obes Relat Dis. Sep.-Oct. 2005;1(5):481-5.
Ostresh et al., "Libraries from libraries": chemical transformation of combinatorial libraries to extend the range and repertoire of chemical diversity.Proc Natl Acad Sci U S A. Nov. 8, 1994;91(23):11138-42.
Pardi et al., Renal and urologic complications of inflammatory bowel disease. Am J Gastroenterol. Apr. 1998;93(4):504-14.
Robertson et al., The cause of idiopathic calcium stone disease: hypercalciuria or hyperoxaluria? Nephron. 1980;26(3):105-10.
Salido et al., Alanine-glyoxylate aminotransferase-deficient mice, a model for primary hyperoxaluria that responds to adenoviral gene transfer. Proc Natl Acad Sci U S A. Nov. 28, 2006;103(48):18249-54.
Saski et al., Protection of ψ (CH2NH) peptide bond with 2, 4-dimethoxybenzyl group in solid-phase peptide synthesis. Chem. Pharm. Bull. Jan. 1997;45(1):13-7.
Schmidt et al., Structure-activity relationships of dermorphin analogues containing N-substituted amino acids in the 2-position of the peptide sequence. Int J Pept Protein Res. Jul. 1995;46(1):47-55.
Sherman et al., Compatibility of thioamides with reverse turn features: synthesis and conformational analysis of two model cyclic pseudopeptides containing thioamides as backbone modifications. J. Am. Chem. Soc. Jan. 1990; 112(1): 433-441.
Sidhu et al., Direct correlation between hyperoxaluria/oxalate stone disease and the absence of the gastrointestinal tract-dwelling bacterium Oxalobacter formigenes: possible prevention by gut recolonization or enzyme replacement therapy. J Am Soc Nephrol. Nov. 1999;10 Suppl 14:S334-40.
Tao et al., Soluble factors from Lactobacillus GG activate MAPKs and induce cytoprotective heat shock proteins in intestinal epithelial cells. Am J Physiol Cell Physiol. Apr. 2006;290(4):C1018-30.
Zalipsky, Functionalized poly(ethylene glycol) for preparation of biologically relevant conjugates. Bioconjug Chem. Mar.-Apr. 1995;6(2):150-65.
International Search Report for PCT/US2018/014494; dated Jul. 19, 2018; 6 pgs.

* cited by examiner

OXALOBACTER FORMIGENES (OF)-DERIVED FACTORS FOR THE TREATMENT OF TREATMENT/PREVENTION OF EXCESS OXALATE LEVELS

CROSS-REFERENCE TO RELATED APPLICATIONS

The present invention claims priority to U.S. Provisional Patent Application Ser. No. 62/448,178, filed Jan. 19, 2017, which is incorporated by reference in its entirety.

STATEMENT REGARDING FEDERAL FUNDING

This invention was made with government support under Grant No. DK067245 and Grant No. DK042086 awarded by the National Institute of Health. The government has certain rights in the invention.

FIELD

Provided herein are compositions comprising *Oxalobacter formigenes* (O)-derived factors and variants and fragments thereof, and method of use thereof for the treatment/prevention excess oxalate levels and conditions and diseases related thereto.

BACKGROUND

Nephrolithiasis, or the formation of mineral deposit blockages in the kidney (kidney stones (KS)), is the second most prevalent kidney disease in USA after hypertension, with a rising prevalence and complications including advanced chronic kidney disease (CKD) and end stage renal disease (ESRD). It remains a major source of patient discomfort and disability, lost working days, and health-care expenditure, with an annual economic cost approaching $10 billion. Hyperoxaluria (HO) is a major risk factor for KS, and 70-80% of KS are composed of calcium oxalate. Urinary oxalate is an important determinant of supersaturation, and the risk for stone formation is affected by small increases in urine oxalate. Oxalate is a metabolic end product that cannot be further metabolized and is highly toxic. The mammalian intestine plays a crucial role in oxalate homeostasis, by regulating the amount of absorbed dietary oxalate and providing an avenue for enteric oxalate excretion. Anion exchanger SLC26A6 (A6)-mediated intestinal oxalate secretion plays a critical role in preventing hyperoxaluria and calcium oxalate kidney stones (COKS). Inflammatory bowel disease patients have a significantly increased risk of KS due to the associated enteric hyperoxaluria. Obesity is a risk factor for KS and obese stone formers often have mild to moderate hyperoxaluria. Hyperoxaluria is also emerging as a major complication (developing in >50% of patients) of bariatric surgery for obesity. With the rising prevalence of obesity and increased utilization of bariatric surgery, it is expected that the incidence of hyperoxaluria and related COKS (including the associated cost burden) will continue to increase at a significant rate. Primary hyperoxaluria (PH) is an inherited disease in which there is endogenous oxalate overproduction, which leads to recurrent KS and/or progressive nephrocalcinosis, ESRD, as well as significant hyperoxalemia, systemic oxalosis and premature death. Systemic deposition of calcium oxalate (oxalosis) leads to bone disease, cardiac arrhythmias, cardiomyopathy, skin ulcers, erythropoietin refractory anemia, and digital gangrene. The only treatment known to fully correct the underlying metabolic defect is liver transplantation or combined kidney-liver transplantation once ESRD develops. In addition, significant hyperoxalemia is also seen in ESRD. Cardiovascular diseases are the leading cause of morbidity and mortality in ESRD patients, and a recent report suggest that the ESRD-associated hyperoxalemia may contribute to this increased risk.

Unfortunately, there is currently no specific therapy that effectively lowers urine and/or plasma oxalate level(s), and the risk of recurrent COKS, nephrocalcinosis, oxalate nephropathy, ESRD, and systemic oxalosis remains substantial in the absence of treatment. *Oxalobacter formigenes* (Of) is an anaerobic bacterium that utilizes oxalate as its exclusive energy source. Of colonization correlates with reduced risk of COKS formation in a number of studies, presumably by reducing intestinal oxalate absorption and urinary oxalate excretion. In addition to degrading intraluminal dietary oxalate, Of also interacts with colonic epithelium by inducing distal colonic oxalate secretion, leading to reduced urinary excretion via a potential unknown secretagogue. Of colonization of PH1 mice (a mouse model of primary hyperoxaluria type 1) significantly reduced serum and urinary oxalate levels due to induction of colonic oxalate secretion. However, all PH1 mice lost colonization within 18 days when switched from a high oxalate/low calcium diet (1.5% oxalate/0.5% calcium; needed to induce and maintain colonization) to regular mouse chow (0.25% oxalate/1% calcium). In addition, colonization cannot be maintained without reducing dietary calcium, which contradicts the current recommendations to increase dietary calcium for preventing recurrent KS. Moreover, it has been suggested from studies in PH patients & PH1 mice that the intraluminal environment in PH is not supportive of sustained Of colonization. Collectively, maintaining Of colonization in the absence of high exogenous oxalate remains problematic (and therefore making use of live Of as a potential therapeutic agent impractical). Treatments and/or therapies for reducing and/or maintaining healthy serum and urinary oxalate levels are needed.

SUMMARY

Provided herein are compositions comprising *Oxalobacter formigenes* (Of)-derived factors and variants and fragments thereof, and method of use thereof for the treatment/prevention of excess oxalate levels and conditions and diseases related thereto. In some embodiments, the Of-derived factors are derived from the OxB strain and/or OXCC13 strain.

In some embodiments, provided herein are methods comprising administering to the subject one or more *Oxalobacter formigenes* (Of)-derived factors, and/or bioactive variants and/or fragments thereof, that result in stimulation of oxalate transport. In some embodiments, conditioned media (CM) (or factors derived therefrom) stimulates oxalate transport by human intestinal Caco2-BBE (C2) cells by activating protein kinase A (PKA) activation and increasing the transport activity of SLC26A6. In some embodiments, Of-derived factors are administered by administering Of CM to the subject. In some embodiments, the Of CM is fractionated, purified, and/or otherwise processed prior to administration. In some embodiments, one or more Of-derived factors are administered by administering peptides and/or polypeptides purified and/or isolated from Of and/or Of CM. In some embodiments, one or more Of-derived factors are administered by administering peptides and/or polypeptides, and/or bioactive variants and/or fragments thereof, produced recombinantly or synthetically. In some embodiments, one or more of the Of-derived factors are Sel1-like repeat (SLR) proteins. In some embodiments, one or more of the Of-derived factors are Sel1 proteins. In some embodiments, one or more of the Of-derived factors are bioactive variants and/or fragments of Of-derived peptidases. In some embodiments, one or more of the Of-derived factors are bioactive variants and/or fragments of SLR proteins (e.g., Sel1 proteins). In some embodiments, one or more of the Of-derived factors comprises 70% or more (e.g., 70%, 75%, 80%, 85%, 90%, 95%, or more, or ranges therebetween) sequence identity to all or a portion of an Of-derived SLR protein (e.g., Sel1 protein). In some embodiments, the SLR protein (e.g., Sel1 protein) or proteins are selected from the group consisting of Sel1, Hrd3, Chs4, Nif1, PodJ, ExoR, AlgK, HcpA, Hsp12, EnhC, LpnE, MotX, and MerG. In some embodiments, Of-derived factor is a bioactive peptide fragment of one of Sel1, Hrd3, Chs4, Nif1, PodJ, ExoR, AlgK, HcpA, Hsp12, EnhC, LpnE, MotX, and MerG, and/or a bioactive peptide having at least 70% (e.g., 70%, 75%, 80%, 85%, 90%, 95%, or more, or ranges therebetween) sequence identity to a fragment thereof. In some embodiments, the Of-derived factor comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, the Of-derived factor comprises a bioactive variant having 70% or more (e.g., 70%, 75%, 80%, 85%, 90%, 95%, or more, or ranges therebetween) sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, the Of-derived factor comprises a bioactive peptide or polypeptide fragment having 70% or more (e.g., 70%, 75%, 80%, 85%, 90%, 95%, or more, or ranges therebetween) sequence identity to a portion of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, administration comprises rectal administration, oral administration, both rectal and oral, injection, or any other suitable route).

In some embodiments, methods are provided of treating or preventing hyperoxaluria and/or hyperoxalemia comprising performing the methods described herein. In some embodiments, treating or preventing hyperoxaluria and/or hyperoxalemia lowers a subject's risk of calcium oxalate kidney stones, nephrocalcinosis, oxalate nephropathy, end stage renal disease, and/or systemic oxalosis.

In some embodiments, provided herein are pharmaceutical compositions comprising one or more *Oxalobacter formigenes* (Of)-derived factors, and/or bioactive variants and/or fragments thereof. In some embodiments, the Of-derived factors are derived from the OxB strain and/or OXCC13 strain. In some embodiments, Of-derived factors (e.g., proteins/fragments/peptides) from other Of human strains (e.g. OXCC13, HOxBLS, HC-1, etc.) corresponding to those identified in the OxB strain are provided and/or find use in embodiments herein. In some embodiments, the pharmaceutical composition comprises Of conditioned media (CM). In some embodiments, the Of CM is fractionated, purified, and/or otherwise processed. In some embodiments, one or more Of-derived factors comprise peptides and/or polypeptides purified and/or isolated from Of and/or Of CM. In some embodiments, one or more Of-derived factors comprise recombinantly or synthetically produced peptides and/or polypeptides. In some embodiments, one or more of the Of-derived factors are selected from polypeptides comprising all or a portion of SEQ ID NOS; 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 101, or 102. In some embodiments, all or a portion of one or more of the Of-derived factors are encoded by all or a portion of a nucleotide of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 96, 100, 101, and 102. In some embodiments, one or more of the Of-derived factors are Sel1-like repeat (SLR) proteins. In some embodiments, one or more of the Of-derived factors are bioactive variants and/or fragments of SLR proteins (e.g., Sel1 protein). In some embodiments, one or more of the Of-derived factors comprises 70% or more (e.g., 70%, 75%, 80%, 85%, 90%, 95%, or more, or ranges therebetween) sequence identity to all or a portion of an Of-derived SLR protein (e.g., Sel1 protein). In some embodiments, the SLR protein (e.g., Sel1 protein) or proteins are selected from the group consisting of Sel1, Hrd3, Chs4, Nif1, PodJ, ExoR, AlgK, HcpA, Hsp12, EnhC, LpnE, MotX, and MerG. In some embodiments, the Of-derived factor is a peptide fragment of one of Sel1, Hrd3, Chs4, Nif1, PodJ, ExoR, AlgK, HcpA, Hsp12, EnhC, LpnE, MotX, and MerG, and/or a bioactive peptide having at least 70% or more (e.g., 70%, 75%, 80%, 85%, 90%, 95%, or more, or ranges therebetween) sequence identity to a fragment thereof. In some embodiments, the Of-derived factor comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, the Of-derived factor comprises a bioactive variant having 70% or more (e.g., 70%, 75%, 80%, 85%, 90%, 95%, or more, or ranges therebetween) sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, the Of-derived factor comprises a bioactive peptide or polypeptide fragment having 70% or more (e.g., 70%, 75%, 80%, 85%, 90%, 95%, or more, or ranges therebetween) sequence identity to a portion of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 90, SEQ ID NO: 92, SEQ ID NO: 94, SEQ ID NO: 96, SEQ ID NO: 101, and/or, SEQ ID NO: 102. In some embodiments, the pharmaceutical composition is formulated for rectal administration, oral administration, and/or injection.

In some embodiments, provided herein are methods of treating or preventing hyperoxaluria and/or hyperoxalemia comprising administering a pharmaceutical described herein to a subject. In some embodiments, treating or preventing hyperoxaluria and/or hyperoxalemia lowers the subject's risk of the risk of calcium oxalate kidney stones, nephrocalcinosis, oxalate nephropathy, end stage renal disease, and/or systemic oxalosis.

DEFINITIONS

Figure 1:
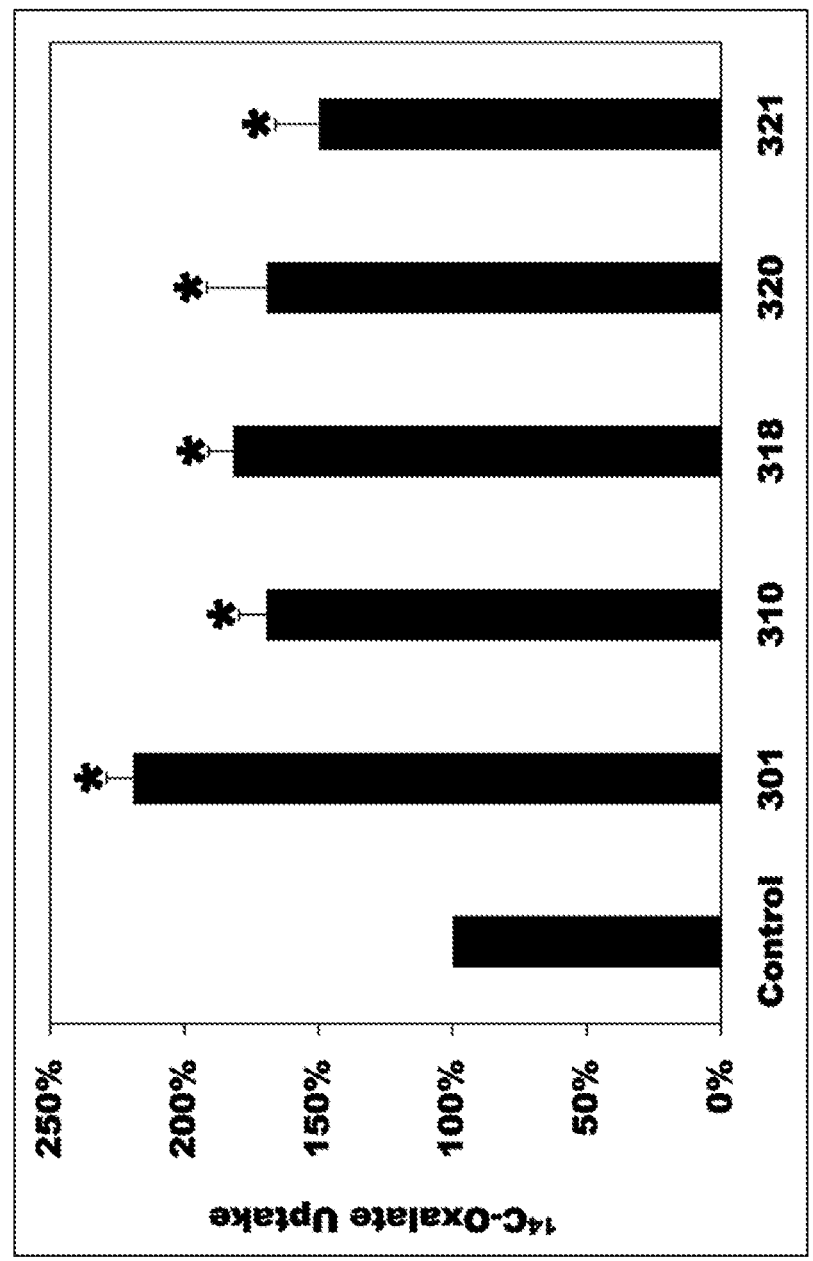
FIG. 1. Sel1 Proteins 301, 310, 318, 320, and 321 significantly stimulate $^{14}C$-oxalate influx into Caco2-BBE (C2) cells.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an Of-derived factor" is a reference to one or more Of-derived factors and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "hyperoxaluria" refers to the excessive urinary excretion of oxalate by a subject (e.g., >25 mg/day).

As used herein, the term "hyperoxalemia" refers to excessive plasma levels of oxalate in a subject. Various studies report a normal range of oxalate in the plasma of 1 to 3 µmol per liter. Subjects with levels exceeding that range are considered to suffer from hyperoxalemia.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" or "variant peptide" refers to a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature) or may be a peptide that is not a subsequence of a naturally occurring protein or polypeptide. For example, a "mutant SLR peptide" (e.g., a "mutant Sel1 protein") may be a subsequence of a mutant version of SLR protein (e.g., Sel1 protein) or may be distinct sequence not found in naturally-occurring SLR proteins (e.g., Sel1 proteins).

As used herein, the term "mutant polypeptide" or "variant polypeptide" refers to a polypeptide having a distinct amino acid sequence from the "wild-type" sequence. A mutant polypeptide may be a naturally-occurring protein that is not the most common sequence in nature (or a polypeptide fragment thereof) or may be a polypeptide that is not a subsequence of a naturally occurring protein or polypeptide. For example, a "mutant SLR polypeptide" may be a naturally occurring SLR protein (e.g., Sel1 protein), a polypeptide fragment of a SLR protein (e.g., Sel1 protein), or may be distinct sequence not found in naturally-occurring SLR proteins (e.g., Sel1 proteins).

As used herein, the term "artificial peptide" or "artificial polypeptide" refers to a peptide or polypeptide having a distinct amino acid sequence from those found in natural peptides and/or proteins. An artificial protein is not a subsequence of a naturally occurring protein, either the wild-type (i.e., most abundant) or mutant versions thereof. For example, an artificial SLR peptide or polypeptide is not a subsequence of naturally occurring SLR protein (e.g., Sel1 protein). An artificial peptide or polypeptide may be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the R carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs. Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated for a disease or condition.

As used herein, the term "effective amount" refers to the amount of a sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The beneficial or intended clinical result may include alleviation of symptoms, a reduction in the severity of the disease, inhibiting a underlying cause of a disease or condition, steadying diseases in a non-advanced state, delaying the progress of a disease, and/or improvement or alleviation of disease conditions.

As used herein, the term "pharmaceutical composition" refers to the combination of an active agent (e.g., Of-derived factor) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions comprising *Oxalobacter formigenes* (Of)-derived factors and variants and fragments thereof, and methods of use thereof for the treatment/prevention excess oxalate levels and conditions and diseases related thereto.

Most kidney stones (KS) are composed of calcium oxalate, and small increases in urine oxalate affect the stone risk. The mammalian intestine plays a crucial role in oxalate homeostasis. Intestinal oxalate secretion mediated by anion exchanger SLC26A6 (A6) plays a major role in limiting net intestinal absorption of ingested oxalate; thereby preventing hyperoxaluria and calcium oxalate kidney stones (COKS). Hyperoxaluria and a high incidence of KS are commonly seen in IBD patients. Hyperoxaluria is also emerging as a major complication of bariatric surgery for obesity. Primary hyperoxaluria (PH) is an inherited disease in which there is endogenous oxalate overproduction. Enhancing intestinal oxalate secretion is expected to lead to reduced urine and plasma oxalate levels. In addition to degrading intraluminal dietary oxalate, the probiotic bacterium *oxalobacter formigenes* (Of) also interacts with colonic epithelium by inducing colonic oxalate secretion, leading to reduced urinary excretion. Significant difficulties exist in sustaining Of colonization in animals and humans in the absence of high exogenous oxalate.

Experiments were conducted during development of embodiments herein to determine whether Of CM affects intestinal oxalate transport using the human intestinal Caco2-BBE (C2) cells. DIDS (anion exchange inhibitor)-sensitive apical oxalate influx was measured in the presence of an outward Cl gradient as an assay of Cl-oxalate exchange, ≥50% of which is mediated by A6. Compared with control medium, Of CM significantly stimulated oxalate uptake (>2.4-fold), whereas CM from *Lactobacillus acidophilus* (La) did not. Treating the CM with heat or pepsin completely abolished this bioactivity, and selective ultrafiltration of the CM revealed that the Of-derived factors have molecular masses of 10-30 kDa. Treatment with the PKA inhibitor H89 or DIDS completely blocked the CM-induced oxalate transport. A6 Knockdown also significantly restricted the induction of oxalate transport by CM. In a mouse model of primary hyperoxaluria type 1, rectal administration of Of CM significantly reduced (>32.5%) urinary oxalate excretion and stimulated (>42%) distal colonic oxalate secretion, reflecting the in vivo retention of biologic activity and the therapeutic potential of these factors.

Experiments conducted during development of embodiments herein to identify the Of-derived bioactive factor(s) inducing colonic oxalate secretion determined that small molecular weight protein(s) and/or peptide(s) secreted by Of in its culture conditioned medium (CM) significantly stimulate(s) oxalate transport (>2.4-fold) by human intestinal Caco2-BBE cells through mechanisms including PKA activation and increased A6 transport activity. Rectal administration of Of CM significantly reduced (>32.5%) urinary oxalate excretion and stimulated (>42%) distal colonic oxalate secretion in PH1 mice. Probiotic bacteria have several health benefits; however, the difficulties in determining intestinal bacterial bioavailability and biosafety concerns when administering live probiotics are problems facing current probiotic clinical applications. These issues are compounded by the difficulties described above in maintaining Of colonization in the absence of high exogenous dietary oxalate.

Experiments conducted during development of embodiments herein demonstrate that Of-derived factors retain their biological activity when administered in vivo and effectively reduce urinary oxalate excretion in hyperoxaluric mice, thereby demonstrating the utility of the Of-derived factors as therapeutic agents for prevention and/or treatment of hyperoxaluria, hyperoxalemia, COKS, and related diseases/conditions.

Figure 2:
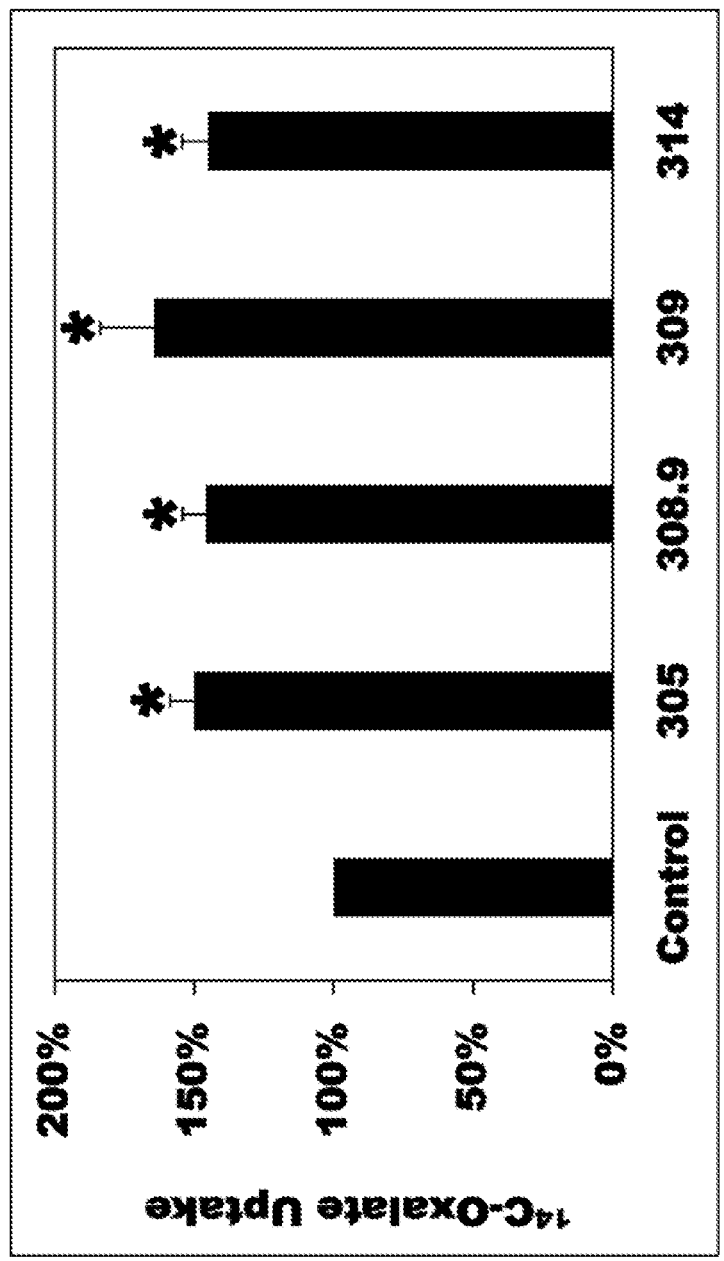
FIG. 2. Non-Sel1 proteins 305, 308.9, 309, and 314 significantly stimulate $^{14}C$-oxalate influx into Caco2-BBE (C2) cells.

Experiments conducted during development of embodiments herein have identified Sel1 repeat proteins as among the Of-derived factors responsible for stimulation of oxalate transport by C2 cells. Sel1 repeat proteins are involved in signal transduction pathways, and this is very important since we found that Of CM signals through PKA to stimulate oxalate transport by C2 cells. 12 Sel1 repeat proteins were purified and the effects of different concentrations and different incubation periods of the purified proteins on oxalate transport by C2 cells were assessed. Sel1 proteins 301, 310, 318, 320, and 321 significantly stimulate (~1.5-2.2-fold) oxalate transport by C2 cells (FIG. 1). The combination of 301+318+320 have a better stimulatory effect (2.5-fold) compared to 301 (FIG. 3). 301+318 also stimulated oxalate transport by ~2.5-fold. Sel1 proteins 304, 317, 319, 322, 323, 324, and 325 also stimulated oxalate transport by C2 cells by ~1.3-1.6-fold. Since all of the 12 tested Sel1 proteins significantly stimulated oxalate transport by C2 cells, it is very likely that the remaining 32 Sel1 proteins (individually or in combination) will also stimulate oxalate and this will be tested. siRNA knockdown of the oxalate transporters SLC26A2 and SLC26A6 greatly reduced Sel1 (Comb3=301+318+320)-induced stimulation of oxalate transport (FIG. 5) as observed with the CM. In addition, 301-induced stimulation of oxalate transport is completely blocked by the PKA inhibitor H89, indicating that Sel1 proteins act through the PKA signaling pathway to stimulate oxalate transport, which is similar to the CM. Collectively, Sel1 proteins almost fully mimic the effects of the CM. Importantly, 3 non Sel1 proteins (311, 315, and 316) have no significant effects on oxalate transport by C2 cells (FIG. 4), strongly indicating that the Sel1-induced stimulation of oxalate transport by C2 cells is specific. In addition to Sel1 proteins, 4 other non Sel1 proteins (305, 308.9, 309, and 314) also stimulated oxalate transport (FIG. 2). In some embodiments, compositions are provided herein that comprise one or more Sel1 proteins or Sel1-derived variants or fragments (e.g., Sel1-derived peptides or polypeptides that stimulate oxalate transport). In some embodiments, methods are provided of treating/preventing excess oxalate levels in the urine and/or plasma by the administration of Sel1 proteins or Sel1-derived variants or fragments (e.g., Sel1-derived peptides or polypeptides that stimulate oxalate transport) to a subject. In some embodiments, compositions are provided herein that comprise one or more Sel1 proteins or Sel1-derived variants or fragments (e.g., Sel1-derived peptides or polypeptides that stimulate oxalate transport). In some embodiments, methods are provided of treating/preventing excess oxalate levels in the urine and/or plasma by the administration of Sel1 proteins or Sel1-derived variants or fragments (e.g., Sel1-derived peptides or polypeptides that stimulate oxalate transport) to a subject.

Sel1-like repeat (SLR) proteins (e.g. Sel1, Hrd3, Chs4, Nif1, PodJ, ExoR, AlgK, HcpA, Hsp12, EnhC, LpnE, MotX, and MerG) are involved in signal transduction pathways. In some embodiments, Of conditioned medium (CM) signals (e.g., through PKA) to stimulate oxalate transport (e.g., by C2 cells) as a result of the signal transduction functions of the SLR proteins (e.g., Sel1 proteins); although embodiments herein are not limited to any particular mechanism of action and an understanding of the mechanism of action is not necessary to practice such embodiments. SLR proteins (e.g., Sel1 proteins) have repeat units (e.g., repeat peptides). Most repeats are 5 to 40 amino acids (e.g., 5, 6, 7, 8, 9, 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, or ranges therebetween), but longer repeat peptides (e.g., 45, 50, 55, 60, 65, 70, 75, 80, 85, 90, 95, 100, or longer or ranges therebetween) are within the scope of the SLR proteins (e.g., Sel1 proteins) herein. In some embodiments, repeat units fold into two to four secondary structural elements. In some embodiments, SLR proteins (e.g., Sel1 proteins) serve as adaptor proteins for the assembly of membrane-bound macromolecular complexes. Several bacterial and eukaryotic SLR proteins (e.g. Sel1 & Hrd3) are activated upon cellular stress. In some embodiments, Of Sel1 proteins are activated when oxalate is low in the culture medium (e.g., as evidenced by the observation of a CM of higher (>2-fold) bioactivity under this condition). Bacterial LpnE, EnhC, HcpA, ExoR, and AlgK proteins mediate the interactions between bacterial and eukaryotic host cells. In some embodiments, the SLR motif establishes a link between signal transduction pathways from eukaryotes and bacteria. In some embodiments, an SLR protein (e.g., Sel1 proteins) comprises leader sequences. In some embodiments, SLR proteins (e.g., Sel1 proteins) without leader sequences, such as PodJ or leaderless analogs of natural SLR proteins (e.g., Sel1 proteins), are active in the periplasmic space. In some embodiments, bacterial SLR proteins (e.g., Sel1 proteins), such as HcpA, ExoR, EnhC and LpnE are responsible for the adaptation of bacteria to different eukaryotic hosts.

The Of genome has 44 Sel1 proteins and one SelR domain, with many of these proteins having molecular masses between 10-30 kDa (e.g., where most of the CM stimulatory activity lies) (Table 1). In addition, several other Sel1 proteins with molecular masses between 32-139 kDa were also identified (Table 1). Many of the Sel1 proteins are predicted to have signal peptides and therefore are secreted proteins. Moreover, Sel1 proteins with molecular masses of 25 (#1361), 33 (#1414), and 68 (#1362) kDa blast in common with another Sel1 protein having a molecular mass of 59 (#1344) kDa. Five Sel1 proteins (#s 1360-1364) resides in an operon, with carbon starvation protein CstA located immediately upstream of this operon. Sel1 proteins #1343, 1344, and 1356 are also located near this operon. In some embodiments, although most of the CM stimulatory activity is mediated by factors with molecular masses between 10-30 kDa, the results of selective ultrafiltration using 30 kDa cutoff column (FIG. 6B) indicates that the factors exist as a multifunctional complex requiring a bacterial product of >30 kDa for optimal functioning. The latter result indicates that different combinations of Sel1 and other identified proteins will providen a level of oxalate transport stimulation similar to (or greater than) that observed with the CM.

TABLE 1

Of-derived proteins

| Name | Protien | Description | DNA seq | Protein seq |
|---|---|---|---|---|
| 301 | 194 | Sel1 repeat :: PF08238 | SEQ ID NO: 1 | SEQ ID NO: 2 |
| 317 | 1343 | Sel1 repeat :: PF08238 | SEQ ID NO: 15 | SEQ ID NO: 16 |
| 310 | 1344 | Sel1 repeat :: PF08238 | SEQ ID NO: 21 | SEQ ID NO: 22 |
| 318 | 1356 | Sel1 repeat :: PF08238 | SEQ ID NO: 9 | SEQ ID NO: 10 |
| 319 | 1360 | Sel1 repeat :: PF08238 | SEQ ID NO: 11 | SEQ ID NO: 12 |
| 320 | 1361 | Sel1 repeat :: PF08238 | SEQ ID NO: 3 | SEQ ID NO: 4 |
| 321 | 1362 | Sel1 repeat :: PF08238 | SEQ ID NO: 5 | SEQ ID NO: 6 |
| 304 | 1363 | Sel1 repeat :: PF08238 | SEQ ID NO: 7 | SEQ ID NO: 8 |
| 322 | 1364 | Sel1 repeat :: PF08238 | SEQ ID NO: 23 | SEQ ID NO: 24 |
| 323 | 1414 | Sel1 repeat :: PF08238 | SEQ ID NO: 13 | SEQ ID NO: 14 |
| 324 | 1548 | Sel1 repeat :: PF08238 | SEQ ID NO: 17 | SEQ ID NO: 18 |
| 325 | 1549 | Sel1 repeat :: PF08238 | SEQ ID NO: 19 | SEQ ID NO: 20 |
|  | 193 | Sel1 repeat :: PF08238 | SEQ ID NO: 25 | SEQ ID NO: 26 |
|  | 235 | Sel1 repeat :: PF08238 | SEQ ID NO: 100 |  |
|  | 238 | Sel1 repeat :: PF08238 | SEQ ID NO: 27 | SEQ ID NO: 28 |
|  | 240 | Sel1 repeat :: PF08238 | SEQ ID NO: 29 | SEQ ID NO: 30 |
|  | 275 | Sel1 repeat :: PF08238 | SEQ ID NO: 31 | SEQ ID NO: 32 |
|  | 841 | Sel1 repeat :: PF08238 | SEQ ID NO: 33 | SEQ ID NO: 34 |
|  | 1112 | Sel1 repeat :: PF08238 | SEQ ID NO: 35 | SEQ ID NO: 36 |
|  | 1124 | Sel1 repeat :: PF08238 | SEQ ID NO: 37 | SEQ ID NO: 38 |
|  | 1143 | Sel1 repeat :: PF08238 | SEQ ID NO: 39 | SEQ ID NO: 40 |
|  | 1250 | Sel1 repeat :: PF08238 | SEQ ID NO: 41 | SEQ ID NO: 42 |
|  | 1257 | SelR domain :: PF01641 | SEQ ID NO: 43 | SEQ ID NO: 44 |
|  | 1412 | Sel1 repeat :: PF08238 | SEQ ID NO: 45 | SEQ ID NO: 46 |
|  | 1419 | Sel1 repeat :: PF08238 | SEQ ID NO: 47 | SEQ ID NO: 48 |
|  | 1423 | Sel1 repeat :: PF08238 | SEQ ID NO: 49 | SEQ ID NO: 50 |
|  | 1551 | Sel1 repeat :: PF08238 | SEQ ID NO: 51 | SEQ ID NO: 52 |
|  | 1715 | Sel1 repeat :: PF08238 | SEQ ID NO: 53 | SEQ ID NO: 54 |
|  | 1790 | Sel1 repeat :: PF08238 | SEQ ID NO: 55 | SEQ ID NO: 56 |
|  | 1942 | Sel1 repeat :: PF08238 | SEQ ID NO: 57 | SEQ ID NO: 58 |
|  | 1945 | Sel1 repeat :: PF08238 | SEQ ID NO: 59 | SEQ ID NO: 60 |
|  | 1954 | Sel1 repeat :: PF08238 | SEQ ID NO: 61 | SEQ ID NO: 62 |
|  | 1955 | Sel1 repeat :: PF08238 | SEQ ID NO: 63 | SEQ ID NO: 64 |
|  | 1960 | Sel1 repeat :: PF08238 | SEQ ID NO: 65 | SEQ ID NO: 66 |
|  | 1969 | Sel1 repeat :: PF08238 | SEQ ID NO: 67 | SEQ ID NO: 68 |
|  | 1970 | Sel1 repeat :: PF08238 | SEQ ID NO: 69 | SEQ ID NO: 70 |
|  | 2000 | Sel1 repeat :: PF08238 | SEQ ID NO: 71 | SEQ ID NO: 72 |
|  | 2001 | Sel1 repeat :: PF08238 | SEQ ID NO: 73 | SEQ ID NO: 74 |
|  | 2022 | Sel1 repeat :: PF08238 | SEQ ID NO: 75 | SEQ ID NO: 76 |
|  | 2025 | Sel1 repeat :: PF08238 | SEQ ID NO: 77 | SEQ ID NO: 78 |
|  | 2123 | Sel1 repeat :: PF08238 | SEQ ID NO: 79 | SEQ ID NO: 80 |
|  | 2176 | Sel1 repeat :: PF08238 | SEQ ID NO: 81 | SEQ ID NO: 82 |
|  | 2239 | Sel1 repeat :: PF08238 | SEQ ID NO: 83 | SEQ ID NO: 84 |
|  | 2249 | Sel1 repeat :: PF08238 | SEQ ID NO: 85 | SEQ ID NO: 86 |
|  | 2270 | Sel1 repeat :: PF08238 | SEQ ID NO: 87 | SEQ ID NO: 88 |
| 314 | 8 | LD-carboxypeptidase :: PF02016 | SEQ ID NO: 89 | SEQ ID NO: 90 |
| 309 | 1525 | Peptidase family S49 :: PF01343 | SEQ ID NO: 91 | SEQ ID NO: 92 |
| 305 | 1524 | haloacid dehalogenase-like hydrolase :: PF00702 | SEQ ID NO: 98 | SEQ ID NO: 101 |
| 315 | 272 | Outer membrane efflux protein :: PF02321 | SEQ ID NO: 93 | SEQ ID NO: 94 |
| 316 | 1285 | Outer membrane efflux protein :: PF02321 | SEQ ID NO: 95 | SEQ ID NO: 96 |
| 308 | 769 | EAL domain :: PF00563 | SEQ ID NO: 99 | SEQ ID NO: 102 |
| 311 | 1847 | MotA/TolQ/ExbB proton channel family :: PF01618 |  |  |

To evaluate whether one or more of these SLR proteins (e.g., Sel1 proteins) are responsible for mediating the CM-induced stimulation of oxalate transport, a subset of Sel1 proteins were cloned and overexpressed in E. coli and the recombinant purified proteins were prepared. 12 Sel1 proteins and 7 additional Of-derived factors were purified (Table 2) and the effects of different concentrations and incubation periods of the purified proteins on oxalate transport by C2 cells were evaluated. Experiments conducted during development of embodiments herein demonstrate that Sel1 proteins (#s 194, 1356, 1361, and 1362), significantly stimulate (up to 2.5-fold) oxalate transport by C2 cells. In addition to the Sel1 proteins, LD-carboxypeptidase (#8), a peptidase (#1525), haloacid dehalogenase-like hydrolase (1524=305), and guanylate cyclase (769=308) also stimulated (~1.4-1.6-fold) oxalate transport by C2 in preliminary studies (FIG. 2). On the other hand, outer membrane efflux proteins (#s 272 and 1285) and MotA/TolQ/ExbB proton channel family (1847=311) failed to stimulate oxalate transport by C2 cells.

TABLE 2

Purified Of-derived proteins

| Protein name | Protein | DNA seq | Protein seq |
|---|---|---|---|
| 301 | 194\|Sel1 repeat :: PF08238 | SEQ ID NO: 1 | SEQ ID NO: 2 |
| 320 | 1361\|Sel1 repeat :: PF08238 | SEQ ID NO: 3 | SEQ ID NO: 4 |
| 321 | 1362\|Sel1 repeat :: PF08238 | SEQ ID NO: 5 | SEQ ID NO: 6 |
| 304 | 1363\|Sel1 repeat :: PF08238 | SEQ ID NO: 7 | SEQ ID NO: 8 |
| 318 | 1356\|Sel1 repeat :: PF08238 | SEQ ID NO: 9 | SEQ ID NO: 10 |
| 319 | 1360\|Sel1 repeat :: PF08238 | SEQ ID NO: 11 | SEQ ID NO: 12 |
| 323 | 1414\|Sel1 repeat :: PF08238 | SEQ ID NO: 13 | SEQ ID NO: 14 |
| 317 | 1343\|Sel1 repeat :: PF08238 | SEQ ID NO: 15 | SEQ ID NO: 16 |
| 324 | 1548\|Sel1 repeat :: PF08238 | SEQ ID NO: 17 | SEQ ID NO: 18 |
| 325 | 1549\|Sel1 repeat :: PF08238 | SEQ ID NO: 19 | SEQ ID NO: 20 |
| 310 | 1344\|Sel1 repeat :: PF08238 | SEQ ID NO: 21 | SEQ ID NO: 22 |
| 309 | 1525\|Peptidase family S49 :: PF01343 | SEQ ID NO: 91 | SEQ ID NO: 92 |
| 315 | 272\|Outer membrane efflux protein :: PF02321 | SEQ ID NO: 93 | SEQ ID NO: 94 |
| 316 | 1285\|Outer membrane efflux protein :: PF02321 | SEQ ID NO: 95 | SEQ ID NO: 96 |
| 314 | 8\|LD-carboxypeptidase :: PF02016 | SEQ ID NO: 89 | SEQ ID NO: 90 |
| 322 | 1364\|Sel1 repeat :: PF08238 | SEQ ID NO: 23 | SEQ ID NO: 24 |
| 305 | 1524\|haloacid dehalogenase-like hydrolase :: PF00702 | SEQ ID NO: 98 | SEQ ID NO: 101 |
| 308 | 769\|EAL domain :: PF00563 | SEQ ID NO: 99 | SEQ ID NO: 102 |
| 311 | 1847\|MotA/TolQ/ExbB proton channel family :: PF01618 | | |

Experiments conducted during development of embodiments herein demonstrate the capacity for Of conditioned media, Of-derived factors, SLR proteins (e.g., Sel1 proteins), SLR peptides (e.g., Sel1 peptides), SLR variant polypeptides (e.g., Sel1 variant polypeptides), etc. to reduce oxalate concentrations and thereby treat and/or prevent conditions related to excess oxalate in the blood, urine, etc.

In some embodiments, Of-derived factors that find use in embodiments herein are derived from any suitable species or strain of *Oxalobacter formigenes*, such as, for example, HC-1, Va3, OxK, OxB, OXCC13, BA1, HOxBLS, HOxRW, POxC, etc. In some embodiments, variants, fragments, and/or peptidomimetics of bioactive factors derived from suitable Of strains are provided.

In some embodiments, media conditioned by the growth of *Oxalobacter formigenes* (CM) is provided. In some embodiments, Of CM is provided in a pharmaceutical composition for the treatment/prevention of conditions related to excess oxalate. In some embodiments, Of CM is processed (e.g., fractionated, purified, concentrated, diluted, filtered, etc.) prior to administration to a subject. In some embodiments, Of CM is formulated for administration by any suitable techniques described herein or known in the field.

In some embodiments, bioactive Of-derived factors are provided for the treatment/prevention of conditions related to excess oxalate. In some embodiments, such factors are obtained, isolated, and/or purified from Of CM. In some embodiments, such factors are obtained, isolated, and/or purified from Of cultures. In some embodiments, are prepare recombinantly and/or synthetically. In some embodiments, bioactive Of-derived factors are SLR proteins (e.g., Sel1 proteins), such as Sel1, Hrd3, Chs4, Nif1, PodJ, ExoR, AlgK, HcpA, Hsp12, EnhC, LpnE, MotX, MerG, and variants, fragment, and peptidomimetics thereof.

Provided herein are compositions (e.g., Of conditioned media, Of-derived factors, SLR proteins (e.g., Sel1 proteins), SLR peptides (e.g., Sel1 peptides), SLR variant polypeptides (e.g., Sel1 variant polypeptides), etc.) which stimulate the clearance of oxalate (e.g., activate oxalate transport) from a biological environment (e.g., blood, urine, etc.). In some embodiments, compositions significantly reduce oxalate concentrations (e.g., urine oxalate, blood oxalate, etc.) for example, by at least 10%, 15%, 20%, 25%, 30%, 35%, 40%, 45%, 50%, 55%, 60%, 65%, 70%, 75%, 80%, 85%, 90%, 95%, or ranges therebetween. In some embodiments, compositions herein stimulate oxalate transport, thereby reducing in vivo oxalate levels in the blood (e.g., plasma oxalate levels), urine, etc., through mechanisms such as, for example, PKA activation and increased activity of SLC26 family members (e.g., SLC26A6) or other transporter(s); although embodiments herein are not limited to any particular mechanism of action and an understanding of the mechanism of action is not necessary to practice such embodiments.

In some embodiments, provided herein are compositions, kits, systems, and/or methods to treat, prevent, reduce the likelihood, treat/prevent a side effect of one or more of: hyperoxalemia, hyperoxaluria, nephrolithiasis, chronic kidney disease, end stage renal disease, calcium oxalate kidney stones, nephrocalcinosis, oxalate nephropathy, primary hyperoxaluria (PH), enteric hyperoxaluria (seen for example in IBD, following small bowel surgery or bariatric surgery, obesity, and celiac disease) and systemic oxalosis. In some embodiments, the reduction in oxalate levels and/or activation of oxalate transport is activated by compositions and methods described herein. In some embodiments, oxalate transport pathways are activated by the compositions and methods described herein. In some embodiments, compositions and methods are utilized in the treatment and/or prevention of hyperoxalemia, hyperoxaluria, and/or related diseases and conditions. In some embodiments, compositions and methods are utilized in screening for peptides and polypeptides useful in the treatment and/or prevention of hyperoxalemia, hyperoxaluria, and/or related diseases and conditions.

In some embodiments, provided herein are pharmaceutical compositions, Of CM, Of-derived factors, SLR peptides (e.g., Sel1 peptides), SLR proteins (e.g., Sel1 proteins), SLR polypeptides (e.g., Sel1 polypeptides), nucleic acids encoding peptides, proteins and polypeptides, molecular complexes of the foregoing, etc. for the treatment or prevention of hyperoxalemia, hyperoxaluria, and/or related diseases and conditions. In some embodiments, provided herein are SLR-peptides and SLR-polypeptides (e.g., comprising less than 100% sequence identity with full length native SLR proteins (e.g., SEQ ID NO: 2, SEQ ID NO: 4, SEQ ID NO:

6, SEQ ID NO: 8, SEQ ID NO: 10, SEQ ID NO: 12, SEQ ID NO: 14, SEQ ID NO: 16, SEQ ID NO: 90, SEQ ID NO: 92, Sel1, Hrd3, Chs4, Nif1, PodJ, ExoR, AlgK, HcpA, Hsp12, EnhC, LpnE, MotX, MerG), or a fragment of full length SLR protein or variant thereof. In some embodiments, a peptide/polypeptide is artificial. In some embodiments, a polypeptide or peptide described herein is prepared by methods known to those of ordinary skill in the art. For example, the peptide or polypeptide can be synthesized using solid phase polypeptide synthesis techniques (e.g. Fmoc or Boc chemistry). Alternatively, the peptide or polypeptide can be produced using recombinant DNA technology (e.g., using bacterial or eukaryotic expression systems). Further, a peptide or polypeptide may be expressed within a subject (e.g., following administration of an appropriate vector). Accordingly, to facilitate such methods, provided herein are genetic vectors (e.g., plasmids, viral vectors (e.g. AAV), etc.) comprising a sequence encoding the polypeptide, as well as host cells comprising such vectors. Furthermore, provided herein are the peptides and polypeptides produced via such methods.

In some embodiments, the administration of Of-derived factors (e.g., peptides and polypeptides) and compositions related thereto (e.g. variants and mimetics of Of-derived factors, nucleic acids encoding Of-derived factors, etc.) is provided. In some embodiments, provided herein is the administration of bioactive agents which reduce oxalate levels in vivo, or are otherwise described herein. Examples of such peptides and polypeptides include those selected from the group consisting of SEQ ID NOS: 2, 4, 6, 8, 10, 12, 14, 16, 90, 92, 94, 96, 101, and 102. Other examples include SLR proteins (e.g., Sel1, Hrd3, Chs4, Nif1, PodJ, ExoR, AlgK, HcpA, Hsp12, EnhC, LpnE, MotX, MerG) derived from various Of strains, and variants and fragments thereof.

In some embodiments, a peptide or polypeptide is provided comprising or consisting of all or a portion of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 90, SEQ ID NO: 92, SEQ ID NO: 94, SEQ ID NO: 96, SEQ ID NO: 101, and SEQ ID NO: 102. In some embodiments, a peptide or polypeptide is provided comprising at least 50% sequence identity to one of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 90, SEQ ID NO: 92, SEQ ID NO: 94, SEQ ID NO: 96, SEQ ID NO: 101, and SEQ ID NO: 102 (e.g. at least 60% sequence identity, at least 70% sequence identity, at least 80% sequence identity, at least 90% sequence identity, at least 95% sequence identity, etc.). In some embodiments, peptide and polypeptides comprise at least one mutation from a wild-type sequence (e.g., SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 90, SEQ ID NO: 92, SEQ ID NO: 94, SEQ ID NO: 96, SEQ ID NO: 101, and SEQ ID NO: 102).

In some embodiments, a peptide/polypeptide is provided that is a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 90, SEQ ID NO: 92, SEQ ID NO: 94, SEQ ID NO: 96, SEQ ID NO: 101, and SEQ ID NO: 102. In some embodiments, a peptide/polypeptide is provided that comprises one or more substitutions (e.g., 1, 2, 3, 4, 5, 6, 7, 8, 9, 10, 11, 12, 13, 14, 15, 16, 17, 18, 19, 20, or more) compared to a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 90, SEQ ID NO: 92, SEQ ID NO: 94, SEQ ID NO: 96, SEQ ID NO: 101, and SEQ ID NO: 102.

In some embodiments, a peptide or polypeptide is provided comprising or consisting of all or a portion of an Of-derived SLR protein (e.g., Sel1 protein) that facilitates reduction of in vivo oxalate levels, such as an SLR protein (e.g., Sel1, Hrd3, Chs4, Nif1, PodJ, ExoR, AlgK, HcpA, Hsp12, EnhC, LpnE, MotX, MerG) derived from an Of strains, and variants and fragments thereof. In some embodiments, a peptide or polypeptide is provided comprising at least 50% sequence identity to an SLR protein (e.g., Sel1, Hrd3, Chs4, Nif1, PodJ, ExoR, AlgK, HcpA, Hsp12, EnhC, LpnE, MotX, MerG) derived from an Of strains (e.g. at least 60% sequence identity, at least 70% sequence identity, at least 80% sequence identity, at least 90% sequence identity, at least 95% sequence identity, etc.). In some embodiments, peptide and polypeptides comprise at least one mutation from a wild-type sequence (e.g., Sel1, Hrd3, Chs4, Nif1, PodJ, ExoR, AlgK, HcpA, Hsp12, EnhC, LpnE, MotX, MerG).

In some embodiments, a peptide/polypeptide is provided that is a fragment of an SLR protein (e.g., Sel1, Hrd3, Chs4, Nif1, PodJ, ExoR, AlgK, HcpA, Hsp12, EnhC, LpnE, MotX, MerG) derived from an Of strain. In some embodiments, a peptide/polypeptide is provided that comprises one or more substitutions (e.g., 1, 2, 3, 4, 5, 6, 7, 8, 9, 10, 11, 12, 13, 14, 15, 16, 17, 18, 19, 20, or more) compared to a fragment of an SLR protein (e.g., Sel1, Hrd3, Chs4, Nif1, PodJ, ExoR, AlgK, HcpA, Hsp12, EnhC, LpnE, MotX, MerG) derived from an Of strain.

Embodiments are not limited to the specific sequences listed herein. In some embodiments, peptides/polypeptides meeting limitations described herein (e.g., Of-derived, reduce oxalate in vivo, biostable, bioavailable, biocompatible, etc.), Land having substitutions not explicitly described are within the scope of embodiments here. In some embodiments, the peptides/polypeptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides/polypeptides described herein may be modified by conservative residue substitutions, for example, of the charged residues (K to R, R to K, D to E and E to D). Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, any embodiments described herein may comprise mimetics corresponding to all or a portion of the Of-derived factors and/or SLR proteins (e.g., Sel1 proteins) described herein, with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, δ-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methyl-arginine), ε-N-methyllysine, allo-hydroxylysine, 2,3-diaminopropionic acid, 2,2'-diaminopimelic acid, ornithine, sym-dimethylarginine, asym-dimethyl arginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46, 47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, the peptides/polypeptides described herein are provided as fusions with other peptides or polypeptides. Such fusions may be expressed from a recombinant DNA which encodes the SLR and/or Of-derived peptide/polypeptide and the additional peptide/polypeptide or may be formed by chemical synthesis. For instance, the fusion may comprise a SLR and/or Of-derived peptide/polypeptide and an enzyme of interest, a luciferase, RNasin or RNase, and/or a channel protein (e.g., ion channel protein), a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein, a targeting sequence (e.g., a myristylation sequence), a mitochondrial localization sequence, or a nuclear localization sequence. The additional peptide/polypeptide may be fused to the N-terminus and/or the C-terminus of the SLR and/or Of-derived peptide/polypeptide. In one embodiment, the fusion protein comprises a first peptide/polypeptide at the N-terminus and another (different) peptide/polypeptide at the C-terminus of the SLR and/or Of-derived peptide/polypeptide. Optionally, the elements in the fusion are separated by a connector sequence, e.g., preferably one having at least 2 amino acid residues, such as one having 13 and up to 40 or 50 amino acid residues. The presence of a connector sequence in a fusion protein of the invention does not substantially alter the function of either element (e.g., the SLR and/or Of-derived peptide/polypeptide) in the fusion relative to the function of each individual element, likely due to the connector sequence providing flexibility (autonomy) for each element in the fusion. In certain embodiment, the connector sequence is a sequence recognized by an enzyme or is photocleavable. For example, the connector sequence may include a protease recognition site.

In some embodiments, provided herein are pharmaceutical compositions comprising of one or more SLR and/or Of-derived peptide/polypeptide described herein and a pharmaceutically acceptable carrier. Any carrier which can supply an active peptide or polypeptide (e.g., without destroying the peptide or polypeptide within the carrier) is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intracisternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), etc.

In some embodiments, provided herein are methods for treating patients suffering from (or at risk of) hyperoxaluria, hyperoxalemia, and/or in need of treatment (or preventative therapy). In some embodiments, a pharmaceutical composition comprising at least one Of-derived and/or SLR peptide/polypeptide described herein is delivered to such a patient in an amount and at a location sufficient to treat the condition. In some embodiments, peptides and/or polypeptides (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application methods of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to an ascertainable degree.

A pharmaceutical composition may be administered in the form which is formulated with a pharmaceutically acceptable carrier and optional excipients, adjuvants, etc. in accordance with good pharmaceutical practice. The Of-derived and/or SLR peptide/polypeptide pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical peptide or polypeptide. In general, the therapeutically effective pharmaceutical compound is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, an Of-derived and/or SLR peptide/polypeptide pharmaceutical composition is provided in a unit dosage form for administration to a subject, comprising one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In various embodiments, the peptides and polypeptides disclosed herein are derivatized by conjugation to one or more polymers or small molecule substituents.

In certain of these embodiments, the peptides and polypeptides described herein are derivatized by coupling to polyethylene glycol (PEG). Coupling may be performed using known processes. See, Int. J. Hematology, 68:1 (1998); Bioconjugate Chem., 6:150 (1995); and Crit. Rev. Therap. Drug Carrier Sys., 9:249 (1992) all of which are incorporated herein by reference in their entirety. Those skilled in the art, therefore, will be able to utilize such well-known techniques for linking one or more polyethylene glycol polymers to the peptides and polypeptides described herein. Suitable polyethylene glycol polymers typically are commercially available or may be made by techniques well known to those skilled in the art. The polyethylene glycol polymers preferably have molecular weights between 500 and 20,000 and may be branched or straight chain polymers.

The attachment of a PEG to a peptide or polypeptide described herein can be accomplished by coupling to amino, carboxyl or thiol groups. These groups will typically be the N- and C-termini and on the side chains of such naturally occurring amino acids as lysine, aspartic acid, glutamic acid and cysteine. Since the peptides and polypeptides of the present disclosure can be prepared by solid phase peptide chemistry techniques, a variety of moieties containing diamino and dicarboxylic groups with orthogonal protecting groups can be introduced for conjugation to PEG.

The present disclosure also provides for conjugation of the peptides and polypeptides described herein to one or more polymers other than polyethylene glycol.

In some embodiments, the peptides and polypeptides described herein are derivatized by conjugation or linkage to, or attachment of, polyamino acids (e.g., poly-his, poly-arg, poly-lys, etc.) and/or fatty acid chains of various lengths to the N- or C-terminus or amino acid residue side chains. In certain embodiments, the peptides and polypeptides described herein are derivatized by the addition of polyamide chains, particularly polyamide chains of precise lengths, as described in U.S. Pat. No. 6,552,167, which is incorporated by reference in its entirety. In yet other embodiments, the peptides and polypeptides are modified by the addition of alkylPEG moieties as described in U.S. Pat. Nos. 5,359,030 and 5,681,811, which are incorporated by reference in their entireties.

In select embodiments, the peptides and polypeptides disclosed herein are derivatized by conjugation to polymers that include albumin and gelatin. See, Gombotz and Pettit, Bioconjugate Chem., 6:332-351, 1995, which is incorporated herein by reference in its entirety.

In further embodiments, the peptides and polypeptides disclosed herein are conjugated or fused to immunoglobulins or immunoglobulin fragments, such as antibody Fc regions.

In some embodiments, the pharmaceutical compositions described herein (e.g., comprising SLR proteins (e.g., Sel1 proteins), Of-derived factors, and/or variants and fragments thereof) find use in the treatment and/or prevention of hyperoxaluria, hyperoxalemia, and related conditions. In some embodiments, the compositions are administered to a subject. In certain embodiments, the patient is an adult. In other embodiments, the patient is a child.

In various embodiments, the peptide/polypeptide is administered in an amount, on a schedule, and for a duration sufficient to decrease triglyceride levels by at least 5%, 10%, 15%, 20% or 25% or more as compared to levels just prior to initiation of treatment. In some embodiments, the peptide/polypeptide is administered in an amount, on a dosage schedule, and for a duration sufficient to decrease oxalate levels (e.g., in urine, in plasma) by at least 10%, 15%, 20%, 25%, 30%, 35%, 40%, 45% or 50%. In particular embodiments, the peptide/polypeptide is administered in an amount, on a schedule, and for a time sufficient to decrease oxalate levels (e.g., in urine, in plasma) by at least 55%, 60%, 65%, even at least about 70% or more.

In certain embodiments, the peptide/polypeptide is administered in an amount, expressed as a daily equivalent dose regardless of dosing frequency, of 50 micrograms ("mcg") per day, 60 mcg per day, 70 mcg per day, 75 mcg per day, 100 mcg per day, 150 mcg per day, 200 mcg per day, or 250 mcg per day. In some embodiments, the polypeptide is administered in an amount of 500 mcg per day, 750 mcg per day, or 1 milligram ("mg") per day. In yet further embodiments, the polypeptide is administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day.

In various embodiments, the peptide/polypeptide is administered on a monthly dosage schedule. In other embodiments, the peptide/polypeptide is administered biweekly. In yet other embodiments, the polypeptide is administered weekly. In certain embodiments, the peptide/polypeptide is administered daily ("QD"). In select embodiments, the polypeptide is administered twice a day ("BID").

In typical embodiments, the peptide/polypeptide is administered for at least 3 months, at least 6 months, at least 12 months, or more. In some embodiments, the peptide/polypeptide is administered for at least 18 months, 2 years, 3 years, or more.

EXPERIMENTAL

Example 1

Of interacts with colonic epithelium and induces distal colonic oxalate secretion, leading to reduced urinary excretion (ref. 14; incorporated by reference in its entirety). Of whole cells, cell membranes, and lysates have been tested on oxalate transport across rat distal colonic tissues mounted in Ussing chambers, and were found to have no effect (ref. 14; incorporated by reference in its entirety). Both the whole cells and lysates caused significant degradation of oxalate in the chamber, necessitating heat treatment of samples to eradicate this inherent enzymatic activity. To further understand this phenomenon, Of was obtained from ATCC (strain OxB) and was grown in an anaerobic chamber (ref. 2; incorporated by reference in its entirety). Of cultures were centrifuged (3,000 g at 4° C. for 10 min) and the supernatant (conditioned medium=CM) was filtered through a 0.22 μm filter to sterilize and remove all bacterial cells and stored at −80° C. (ref. 5; incorporated by reference in its entirety). C2 cells were used as a model to evaluate the effects of Of CM on intestinal oxalate transport. Apical $^{14}$C-oxalate flux studies in C2 cells were performed. Apical oxalate uptake by C2 cells was assessed by imposing an outward Cl gradient by removing extracellular Cl $[Cl_i>Cl_o]$ and measuring DIDS (anion exchange inhibitor)-sensitive influx of radioactive $^{14}$C-oxalate in exchange for intracellular Cl [i.e. apical Cl-oxalate exchange activity, ≥50% of which is mediated by A6 in C2 cells (ref. 12; incorporated by reference in its entirety)]. A6 operates in the direction of exchanging intracellular oxalate for mucosal Cl during the process of transepithelial intestinal oxalate secretion. However, A6 can operate in either direction (ref. 21; incorporated by reference in its entirety), and therefore its activity was measured by the more convenient assay of cellular oxalate uptake. C2 cells grown on TRANSWELLS were treated apically with Of culture medium (OM) or CM (1:50 dilution×24 h) before measuring $^{14}$C-oxalate uptake.

Compared to untreated (UT) and OM, the CM significantly stimulated (>2.4-fold) oxalate transport by C2 cells (ref 4; incorporated by reference in its entirety). Similar effects were also observed with 6- and 16-h incubations, but no effect was seen at 1 h. CM or OM did not affect the medium pH. In addition, OM or CM had no significant effect on the transepithelial resistance, indicating that the OM or the CM does not affect the paracellular permeability. These results indicate that secreted bioactive factors in Of CM are responsible for the observed stimulatory regulation by modulating the activity of the involved anion exchanger(s) (A1, A2, and/or A6). *Lactobacillus acidophilus* (La) degrades intraluminal oxalate (19), but it is unknown whether La similarly interacts with enterocytes and modulates intestinal oxalate transport as Of (ref. 14; incorporated by reference in its entirety). Therefore, to ensure specificity, experiments similarly evaluated the effect of La CM. It was observed that La CM (1:25 dilution×24 h) had no effect on oxalate transport by C2 cells compared to UT cells and cells treated with the control medium (ref. 4; incorporated by reference in its entirety). These results indicate that Of CM-induced stimulation of oxalate transport is specific and is possibly mediated by one or more of Of-derived secreted bioactive factor(s).

To have an idea about the nature of Of-derived secreted bioactive factor(s), CM was subjected to heat treatment (boiling at 100° C. for 20-30 min). Heat treatment completely abolished the CM-induced stimulation, indicating that the secreted factor(s) are likely to be protein(s) or peptide(s), rather than, for example, small molecules. Pretreatment of the CM with pepsin or trypsin also completely abolished the stimulatory effect, providing further evidence that the secreted factor(s) is/are proteins or peptides. Selective ultrafiltration revealed that the secreted factors have molecular masses (MM) between 10-30 kDa (ref. 4; incorporated by reference in its entirety). Pretreatment with the PKA inhibitor H89 completely blocked the CM-induced stimulation of oxalate transport by C2 cells, indicating that the observed stimulation is mediated by PKA activation. The observed stimulation is also completely blocked by DIDS, indicating that it is due to active anion exchange-mediated transport process. siRNA A6 knockdown greatly reduced the observed stimulation, indicating that a significant component of CM-induced oxalate transport is A6-mediated. The CM significantly increased (>2-fold) the $V_{max}$ (e.g., greater transport capacity) and reduced (>3.4-fold) the $K_m$ (e.g., greater affinity for oxalate) of the involved transporter(s). The CM did not affect A6 mRNA and total/surface protein expression, and in view of the reduced $K_m$ (reflecting greater A6 affinity for oxalate), indicating that the observed stimulation is due to mechanisms including CM-induced enhanced A6 transport activity (e.g., resulting from an increase in the intrinsic activity of the preexisting A6 membrane transporters), although embodiments herein are not limited to any particular mechanism of action and an understanding of the mechanism of action is not necessary to practice such embodiments.

To evaluate the in vivo effects of the CM on overall oxalate homeostasis, CM or OM was given rectally as enemas (100 μl twice daily×21 days) to PH1 mice (a model of PH type 1 due to deficiency in the liver enzyme AGAT and they have significant hyperoxalemia and hyperoxaluria) (ref. 28; incorporated by reference in its entirety). It was confirmed that the PH1 mice have significant hyperoxaluria (>2.7-fold) compared to their controls. The CM significantly reduced urinary oxalate excretion by >32.5%, while the OM had no significant effect (ref. 4; incorporated by reference in its entirety). To determine whether the Of-derived bioactive factor(s) interact(s) with the colonocyte and induce(s) oxalate secretion in vivo, leading to the observed reduction in urinary oxalate excretion in PH1 mice, distal colonic tissues were isolated and mounted in Ussing chambers at the end of the treatment period. While a small net oxalate secretory flux (−4.7±2.4) was observed in distal colonic tissues from OM-treated PH1 mice, a >4.2-fold higher net oxalate secretory flux (−20.0±5.5) was seen in distal colonic tissues from CM-treated PH1 mice (pmol/cm2/h: OM: $J_{MS}$ (absorptive flux)=37.8±5.9, $J_{SM}$ (secretory flux)=42.6±5.5; CM: $J_{MS}$=40.6±3.7, $J_{SM}$=60.6±3.1), which is due to significantly increased (>42%) $J_{SM}$ (4). CM or OM had no significant effect on $J_{MS}$. These results indicate that the Of-derived factors reduce urinary oxalate excretion in PH1 mice through mechanisms including enhanced net distal colonic oxalate secretion, as well as they retain their biological activity in vivo, thus indicating their significant therapeutic value.

An important factor in purifying the bioactive protein(s) is their presence in a high concentration in the CM. Since Of might secrete these factors as a survival strategy when oxalate is limited (ref. 14; incorporated by reference in its entirety), it was tested whether lower growth medium oxalate concentration lead to more secreted factor(s), and therefore, to a CM with higher bioactivity, by reducing oxalate concentration from 37.5 mM to 18.8 & 9.4 mM. The bioactivity of the CM is significantly higher (>2-fold) with CM9.4 compared to CM37.5 (ref. 4; incorporated by reference in its entirety), demonstrating that the secretion of these factors is inducible, which facilitates their characterization. As a first step in characterizing these factors, secreted proteins in Of CM were purified utilizing column chromatography, using a commercially available kit for rapid screening of a suitable column. 1 ml of the CM was loaded onto different columns (e.g. anion and cation exchange columns) and the flow-through fractions were collected and their effects on oxalate influx into C2 cells were evaluated. The fractions from the weak cationic column (WCC) were found to have no stimulatory effect compared with the parent CM, indicating that this is due to sticking of the potential factor(s) to this column. The factor(s) were then eluted from this column using high salt (0.5-1 M NaCl). Following desalting and concentration of the eluted fraction using a desalting/concentrating column, the eluted fraction is found to have an activity similar to the parent CM (pmoles/cm2/min: UT=1.56±0.30; CM=8.47±0.86; Eluted fraction=7.36±0.69). These findings indicate that the purification process has led to enrichment of the factor(s) in the eluted fraction and the WCC was utilized in subsequent purification studies using FPLC.

Figure 4:
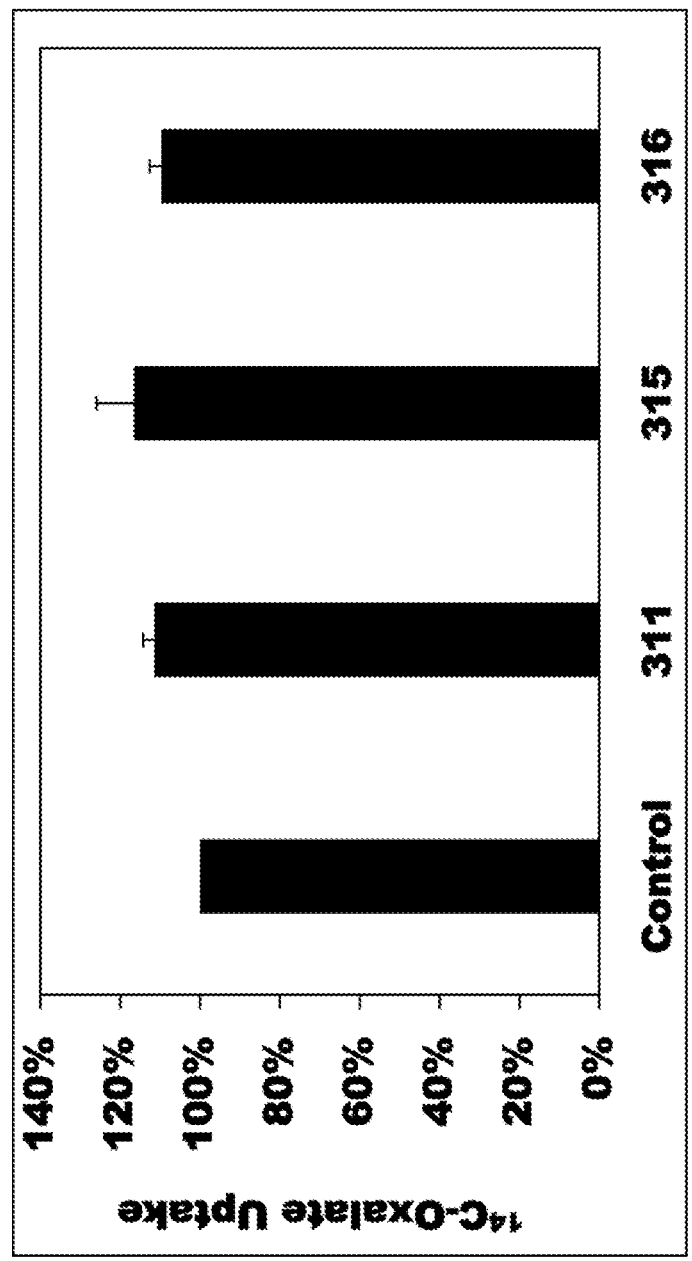
FIG. 4. Non-Sel1 proteins 311, 315, and 316 have no significant effect on $^{14}C$-oxalate influx into Caco2-BBE cells.

The experiments demonstrate that small molecular weight protein(s) and/or peptide(s) in Of CM significantly stimulate(s) oxalate transport (>2.4-fold) by human intestinal Caco2-BBE cells (FIG. 1, FIG. 2, and FIG. 4). Importantly, Of CM also significantly reduced (>32.5%) urinary oxalate excretion in a mouse model of primary hyperoxaluria (PH1), by stimulating (>42%) distal colonic oxalate secretion, reflecting the in vivo retention of biologic activity and the therapeutic value of these factors.

The high specific activity elution fraction was run in SDS-PAGE and then stained by COOMASSIE BLUE. Several bands in the molecular weight range from 10-30 kDa, as well as bands ~52 and 68 kDa were noted. Tandem mass spectrometry was utilized as a primary strategy to identify candidates for the mediators. The gel sections containing the bands were cut and in-gel trypsin proteolysis was performed. Isolated peptides were subjected to LTQ Orbitrap ESI LC-MS/MS analysis, using standard conditions. The data were analyzed by Mascot and X! Tandem database search against the predicted Of proteome, combined with a reverse decoy database to estimate false discovery rate. The results were then validated and visualized using Scaffold. On the basis of 16S rRNA sequence similarities and lipid content, Of strains are divided into two groups: Group I is represented by strain OxB (the strain used in the above experiments) and human strain OxCC13, while Group II is represented by human strain HOxBLS. OXCC13 and HOxBLS genomes were published. Searching against the OXCC13 genome yielded 52 candidates Of protein CM stimulatory factors. A more stringent search (Maxquant: 20 ppm, with additional filtering at 1% FDR) yielded 6 candidate proteins which are the following: transcriptional regulator, LuxR family (ID #C3X886), Raf-like protein (ID #C3XB51), Tryptophan synthase alpha chain (ID #C3XAU0), Sel1 repeat protein (C3X8T9), Uncharacterized protein (ID C3X964), and Uncharacterized protein (ID #C3XCY9). CM from OXCC13 is not commercially available to be cultured. Therefore, the OxB whole genome was sequenced and assembled. The data generated by MassSpect was re-analyzed against the OxB genome and the amino acid sequences for the corresponding proteins identified above by searching the OXCC13 genome were obtained.

Example 2

Several of the identified Of proteins were of interest, especially the Sel1 proteins. Sel1-like repeat (SLR) proteins (e.g. Sel1, Hrd3, Chs4, Nif1, PodJ, ExoR, AlgK, HcpA, Hsp12, EnhC, LpnE, MotX, and MerG) are involved in signal transduction pathways (ref 24; incorporated by reference in its entirety). It was found that Of CM signals through PKA to stimulate oxalate transport by C2 cells. SLR proteins have repeat units and most repeats consist of 5 to 40 amino acids (but some could be much larger) that fold into two to four secondary structural elements. All SLR proteins seem to serve as adaptor proteins for the assembly of membrane-bound macromolecular complexes (ref. 24; incorporated by reference in its entirety). Several bacterial and eukaryotic SLR proteins (e.g. Sel1 & Hrd3) are activated upon cellular stress, which is of interest since Of Sel1 proteins might be activated when oxalate is low in the culture medium given the observation of a CM of higher (>2-fold) bioactivity under this condition. Bacterial LpnE, EnhC, HcpA, ExoR, and AlgK proteins mediate the interactions between bacterial and eukaryotic host cells. The SLR motif establishes a link between signal transduction pathways from eukaryotes and bacteria. Many SLR proteins contain leader sequences and even SLR proteins without leader sequences, such as PodJ for example, are active in the periplasmic space. In addition, other bacterial SLR proteins, such as HcpA, ExoR, EnhC and LpnE seem to be responsible for the adaptation of bacteria to different eukaryotic hosts (ref 24; incorporated by reference in its entirety).

Of has about 44 Sel1 proteins, with many having molecular masses between 10-30 kDa. In addition, several other Sel1 proteins have molecular masses between 32-68 kDa. Most of the Sel1 proteins are predicted to have signal peptides and therefore are secreted proteins. Moreover, Sel1 proteins with molecular masses of 25 (#1361), 33 (#1414), and 68 (#1362) kDa blast in common with another Sel1 protein having a molecular mass of 59 (#1344) kDa. Five Sel1 proteins (#s 1360-1364) resides in an operon, with carbon starvation protein CstA located immediately upstream of this operon. Sel1 proteins #1343, 1344, and 1356 are also located near this operon. Other interesting candidates include diguanylate cyclase, a peptidase, putative outer membrane efflux protein OprC, outer membrane efflux protein OprM, LD-carboxypeptidase, stringent starvation protein B, ribonucleotide reductase, and Hsp20. Although most of the CM stimulatory activity is mediated by factors with masses between 10-30 kDa, the results of selective ultrafiltration using 30 kDa cutoff column indicate that the factors might exist as a multifunctional complex requiring a bacterial product of >30 kDa for optimal functioning. The fact that Sel1 proteins seem to serve as adaptor proteins for the assembly of membrane-bound macromolecular complexes might be of particular interest here. To evaluate whether one or more of these candidate proteins are the Of-derived bioactive factor(s) mediating the CM-induced stimulation of oxalate transport, the proteins (starting with the target Sel1 proteins) were cloned and overexpressed in *E. coli* and the recombinant purified proteins were obtained (Table 2).

Figure 3:
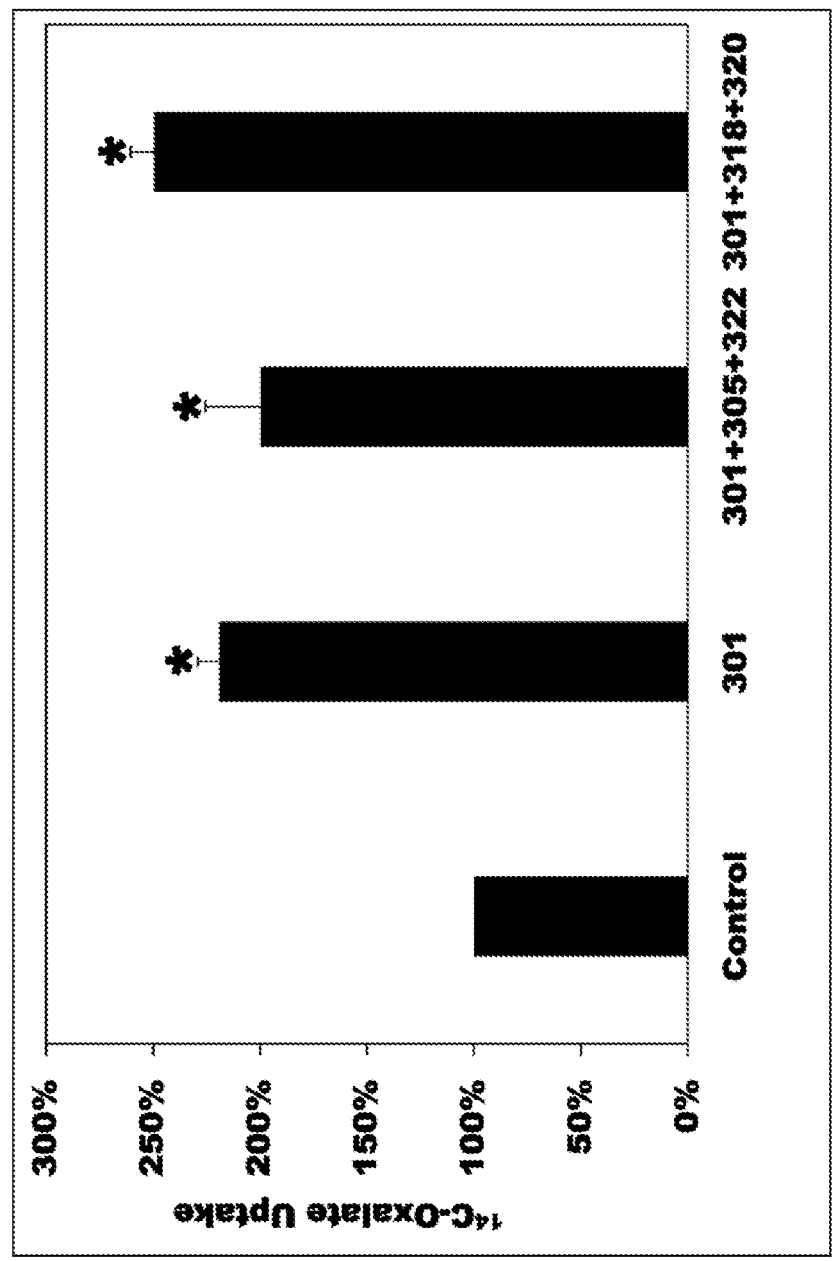
FIG. 3. Combination of 301+318+320 stimulate $^{14}C$-oxalate influx into Caco2-BBE (C2) cells more than 301 alone.
Figure 5:
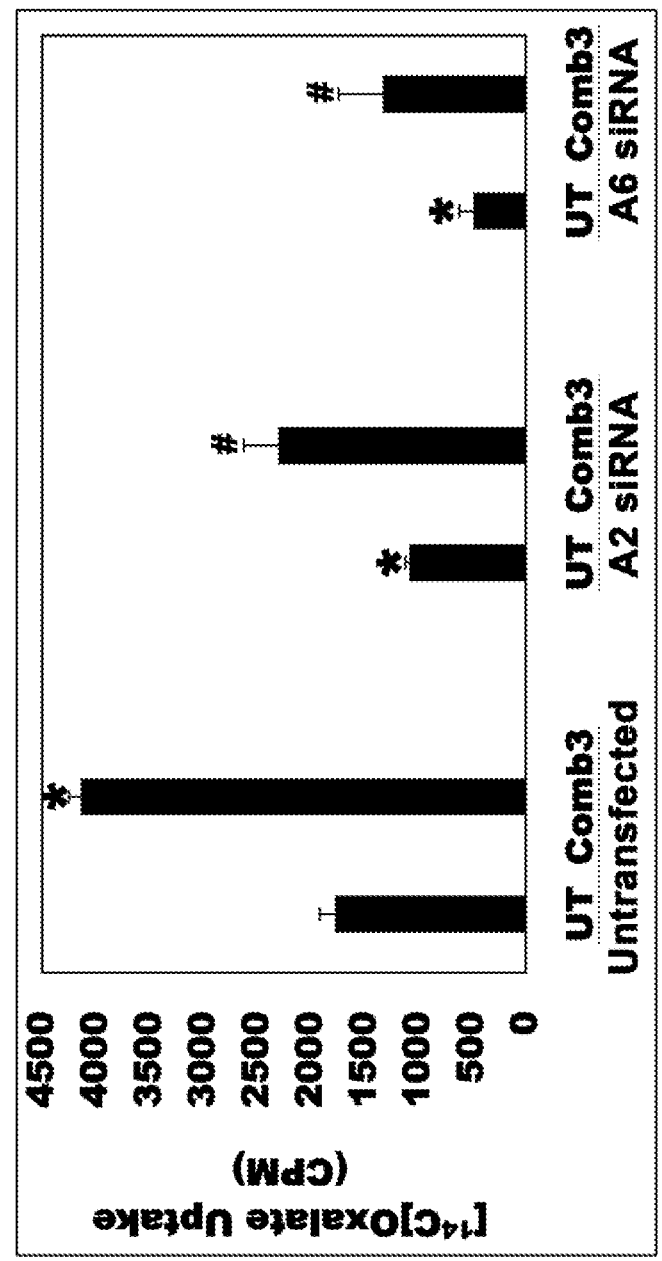
FIG. 5. siRNA knockdown of the oxalate transporters SLC26A6 (A6) and SLC26A2 (A2) greatly reduced the Sel1 (Comb3=301+318+320)-induced stimulation of $^{14}C$-oxalate influx into C2 cells, indicating that Sel1 proteins stimulate oxalate transport by C2 cells through mechanisms including enhanced A6 and A2 transport activities.

The effects of different concentrations (including different incubation periods) of the purified proteins on oxalate transport by C2 cells is similarly tested, as well as examining the effects of different combinations of the purified proteins. Testing the combined effects of the different proteins is important even if one candidate is found to have a significant stimulatory effect, giving the possibility that this might lead to a much higher stimulation (FIG. 3 and FIG. 5).

To evaluate the in vivo effects of the Sel1 proteins, LD-carboxypeptidase, and the peptidase (including any peptidmimetics versions of them or other embodiments), the proteins (individually or in different combinations) are administered (rectally, orally, both oral and rectal, or any other feasible route) to PH1 mice for up to 28 days. The PH1 mice are placed in metabolic cages and urine, plasma, and feces is collected on days 0, 7, 14, 21, and 28. When a factor is found to normalize or significantly reduce serum and urinary oxalate levels in PH1 mice, it is then examined whether the observed changes are due to factor-mediated enhanced net intestinal (small and/or large intestine depending on the route of administration) oxalate secretion. To this end, intestinal tissues (jejunum, ileum, cecum, proximal & distal colon) are isolated and mounted in Ussing chambers at the end of the treatment period found to be associated with the maximum reduction in serum and/or urine oxalate levels. Compared to vehicle-treated PH1 mice, if net basal cecal oxalate flux is converted from absorption to secretion, or significantly higher net basal secretory flux(s) is/re observed in the proximal and/or the distal colon of treated PH1 mice (due to significantly increased secretory flux and/or reduced absorptive flux), then such findings demonstrate that the factor reduces serum and/or urine oxalate levels by enhancing intestinal oxalate secretion. As a result of enhanced intestinal oxalate secretion/excretion, fecal oxalate is higher in the factor-treated mice, which is confirmed. Collectively, such findings provide a molecular basis for therapeutic application of a factor for prevention and/or treatment of hyperoxaluria, hyperoxalemia, and related COKS.

An alternative approach is to use differential proteomics. As described above, lowering culture medium oxalate from 37.5 mM (5 g/L) to 9.4 mM (1 g/L) led to a CM with >2-fold higher bioactivity, while increasing oxalate to 187.5 (25 g/L) led to a CM with reduced activity by ~50-70%. Further lowering of oxalate (0.5, 0.25, 0.1 g/L, as well as oxalate free culture medium) may lead to a CM with much higher bioactivity compared with 9.4 mM. If 0.25 g/L is found to be associated with the highest bioactivity, CMs are then prepared from Of cells grown in the low (will designate CM-low and its corresponding control medium will be OM-low) and high (will designate CM-high and its corresponding control medium will be OM-high) oxalate culture media (6 per condition). Label-free differential proteomics is used to analyze the samples. After excluding the proteins showing up in OM-low & high, the abundance of proteins in CM-low & high are compared. Observing proteins with significantly higher abundance in CM-low, while the same proteins are noted to be low or absent in CM-high, indicates that one or more of these proteins is an Of-derived bioactive factor(s). Promising candidate proteins are then be cloned and overexpressed in *E. coli* and the effects of the recombinant protein(s) are tested as above.

An alternative strategy is to examine the Of transcriptome under low and high oxalate concentrations in the culture medium. To this end, Of cells grown in the low and high oxalate culture media are isolated and RNA for transcriptome analysis is prepared. RNA is extracted from replicate cultures (e.g., 3-5 per condition) grown under the two oxalate concentrations. Ribosomal RNA is subtracted and mRNA is used to generate cDNA libraries for sequencing. Transcript data is mapped to the assembled Of genome sequence using Bowtie (ref. 22; incorporated by reference in its entirety), and data normalization and differential expression analysis is done using the methods implemented in the DESeq2 R package (ref 23; incorporated by reference in its entirety). This approach facilitates the identification of genes (and/or operons) that are differentially regulated under these conditions. If, for example, certain genes are noted to be upregulated under low oxalate, but downregulated under the high oxalate, the protein products of these genes are then overexpressed in *E. coli* and the effects of the recombinant protein(s) are tested.

Example 3

The CM significantly reduced (>32.5%) urinary oxalate excretion in PH1 mice, indicating that the Of-derived factors retain their biological activity in vivo. To test whether the Of-derived factor(s) also decrease urinary oxalate excretion in enteric hyperoxaluria (EH) (e.g. IBD- and obesity-associated hyperoxaluria), the purified factor(s) are similarly given to SAPM1/YitFc (SAM) and ob/ob (ob) mice. SAM is a mouse model with remarkable similarities to human Crohn's disease developed as an ideal model for the IBD-associated hyperoxaluria (>2-fold hyperoxaluria compared to their controls). ob is an obesity model developed as an ideal model for the obesity associated hyperoxaluria (>3.3-fold hyperoxaluria compared to their controls). SAM and ob mice are treated with the purified factors as described above. SAM and ob mice are placed in metabolic cages and urine & feces are collected (including baseline collection). Observing normalization or significantly reduced urinary oxalate levels in factor-treated SAM and/or ob mice compared with vehicle-treated mice indicates that the factor has therapeutic potential not only for PH but also for EH and related COKS. Experiments then examine whether any observed reduction in urinary oxalate excretion in SAM and/or ob mice is due to factor-mediated enhanced net intestinal oxalate secretion.

Experiments are also conducted to evaluate the effects of the CM on the hyperoxaluria observed in the SAM and ob mice. Given the unavailability of any specific therapy that effectively reduces urinary oxalate excretion, the CM provides a therapeutic option under conditions in which it significantly reduces urine oxalate levels in these mouse models. Since Of has been given (as a frozen cell paste or a lyophilized Of formulated in enteric coated capsules) to PH patients (ref. 18; incorporated by reference in its entirety), it is reasonable to give a product of this bacterium to PH patients. Of CM or OM will be similarly (as described above with PH1 mice) given to SAM and ob mice and the results will be similarly interpreted.

Artificial colonization of wild-type mice with the human Of strain HC-1 led to the presence of the bacteria not only in the colon, but unexpectedly also in the small intestine for some time (ref. 15; incorporated by reference in its entirety). This was associated with a significant net oxalate secretion in the distal ileum, cecum, and distal colon, as well as significantly reduced urinary oxalate excretion. In view of these findings, it is possible that oral administration of Of CM (or the purified factor(s)) might promote significant stimulation of net oxalate secretion in both small and large intestines, thereby potentially leading to normalization or greater reduction in plasma and urinary oxalate levels in PH1 mice compared to rectal CM. Therefore, gelatin capsules containing freeze-dried of CM (or the purified factor(s) are prepared for oral administration. To protect the contents of the capsules during passage through the acidic upper gastrointestinal tract, the capsules are coated with EUDRAGIT L 100-55 (ref. 14), which will also protect their contents from protease digestion. Placebo-treated mice will receive Eudragit-coated empty capsules. This approach was used for making encapsulated freeze-dried preparation of Of lysate which was then given orally to hyperoxaluric rats and led to induction of distal colonic oxalate secretion. A 2×2 factorial design is followed with the following 4 groups: placebo-placebo, oral CM, rectal CM, and oral+rectal CM. The PH1, SAM, and ob mice receive the capsules by an intragastric needle twice daily for 5-20 days, and urine, plasma, & feces is collected (including baseline collection), as well as intestinal tissues (jejunum, ileum, cecum, proximal & distal colon) are isolated and mounted in Ussing chambers at the end of the treatment period. The data are analyzed by repeated measures ANOVA with treatment group as the between-subjects factor and time as the within-subjects repeated factor. The treatment group is tested by time interaction to determine whether the change with treatment varies based on treatment received. Observing normalization or a greater reduction in plasma and urinary oxalate levels in PH1 mice with oral CM compared to rectal CM, due to significant stimulation of net oxalate secretion in the small and/or large intestine(s), indicates that the oral route is better. Finding that oral+rectal CM is associated with a much higher reduction in plasma and urinary oxalate levels compared with either oral CM or rectal CM alone, has significant therapeutic implications. Of note is that the CM or OM was given as rectal enemas through special tips that were introduced to ~2 cm from the anus, and the mice were then held from their tails with the heads down and kept in that position for ~one minute.

Example 4

The nucleotide sequences of the proteins in Table 2 from the OxB *oxalobacter* strain were sequenced compared to the human *oxalobacter* strain OXCC13. The OxB, OXC, or other Of-derived nucleotide sequences, and variants thereof, may find use in embodiments described herein. In some embodiments, nucleic acids and/or polypeptides comprising such sequences find use in the embodiments described herein.

Example 5

Figure 6:
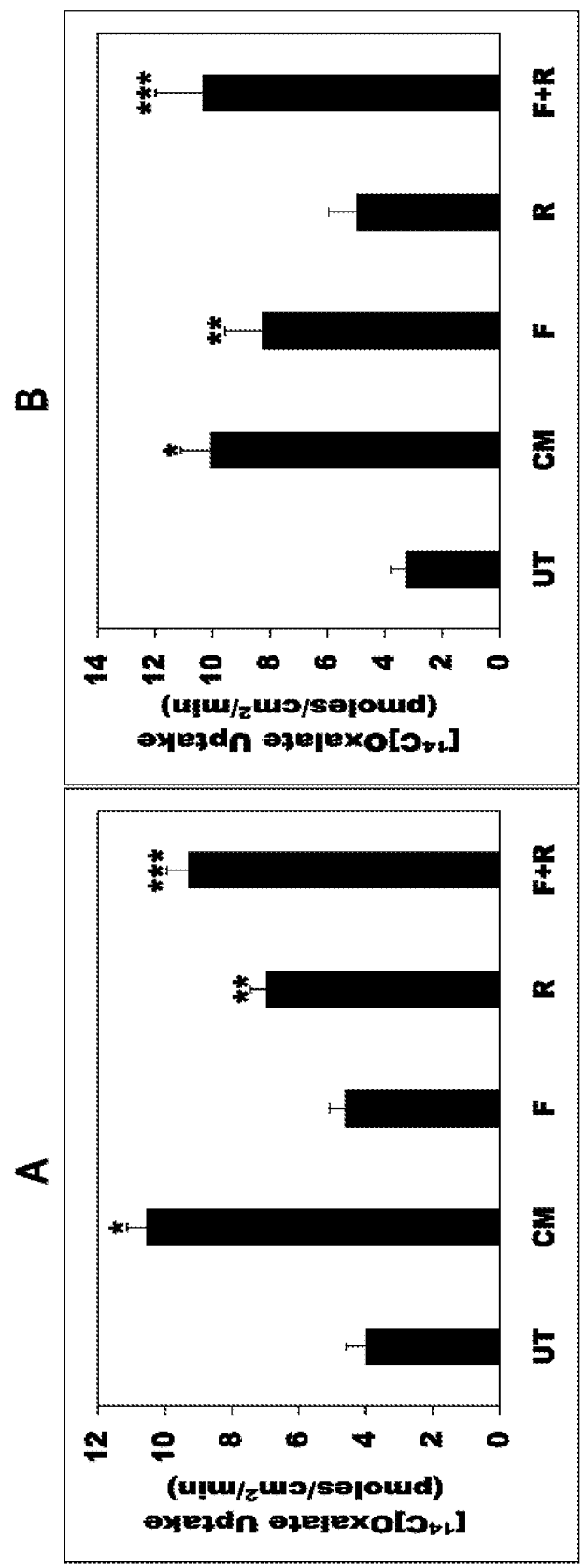
FIG. 6. Effect of selective ultrafiltration using 10 kDa (Panel A) and 30 kDa (Panel B) cutoff spin columns on the CM-induced stimulation of $^{14}C$-oxalate uptake by Caco2-BBE (C2) cells. C2 cells were untreated (UT) or were treated with the conditioned medium (CM), the filtrate (F), the retentate (R), or the combined fractions (F+R). The results indicate that the molecular weights s of the factors are largely between 10-30 kDa. Since F+R have a better stimulatory effect than F, while R has no effect, such data suggest the possibility that these factors might exist as a multifunctional complex requiring a bacterial product of >30 kDa for optimal functioning. These results support testing different combinations of Sel1 and other identified proteins to obtain a level of oxalate transport stimulation similar to that observed with the CM.

Experiments were conducted during development of embodiments herein to determine the molecular weight(s) (MWs) of the secreted factor(s), the conditioned medium (CM) was subjected to selective ultrafiltration using 10- and 30-kDa cutoff spin columns. C2 cells were untreated (UT) or treated with the CM, filtrate (F), retentate (R), or F+R. Using a 10-kDa column, the R and the F+R significantly stimulated oxalate uptake by C2 cells, while the F has no effect (FIG. 6A). Using a 30-kDa column, the F and the F+R significantly stimulated oxalate uptake by C2 cells, while the R has no effect (FIG. 6B). Collectively, these results indicate that the MWs of the factors are largely between 10-30 kDa. Since F+R have a better stimulatory effect than F, while R has no effect, such data suggest the possibility that these factors might exist as a multifunctional complex requiring a bacterial product of >30 kDa for optimal functioning. Therefore, evaluating the effects of different combinations of the Sel1 proteins and the other proteins (305, 308, 309, & 314) is critical to reach to a level of stimulation similar to the CM-induced stimulation (~3-fold) (FIG. 5 and FIG. 6). Sel1 proteins 304, 317, 319, 322, 323, 324, & 325 stimulate oxalate transport by ~1.2-1.6-fold in preliminary studies.

REFERENCES

The following references, some of which are cited above, are herein incorporated by reference in their entireties.
1. Alexander R T, Hemmelgarn B R, Wiebe N, Bello A, Morgan C, Samuel S, Klarenbach S W, Curhan G C, Tonelli M, and for the Alberta Kidney Disease N. Kidney stones and kidney function loss: a cohort study. *Bmj* 345: e5287, 2012.
2. Allison M J, Dawson K A, Mayberry W R, and Foss J G. *Oxalobacter formigenes* gen. nov., sp. nov.: oxalate-degrading anaerobes that inhabit the gastrointestinal tract. *Archives of microbiology* 141: 1-7, 1985.
3. Amin R, Sharma S, Ratakonda S, and Hassan H A. Extracellular Nucleotides Inhibit Oxalate Transport by Human Intestinal Caco2-BBE Cells Through PKC-delta Activation. *American journal of physiology Cell physiology*, 2013.
4. Arvans, D., Jung, Y., Antonopoulos, D., Koval, J., Granja, I., Bashir, M., Karrar, E., Roy-Chowdhury, J., Musch, M., Asplin, J., Chang, E., and Hassan, H. A. *Oxalobacter formigenes*-derived Bioactive Factors Stimulate Oxalate Transport by Intestinal Epithelial Cells. 2017. Journal of the American Society of Nephrology (JASN). 28: 876-887.
5. Borthakur A, Gill R K, Tyagi S, Koutsouris A, Alrefai W A, Hecht G A, Ramaswamy K, and Dudeja P K. The probiotic *Lactobacillus acidophilus* stimulates chloride/hydroxyl exchange activity in human intestinal epithelial cells. *The Journal of nutrition* 138: 1355-1359, 2008.
6. Caudarella R, Rizzoli E, Pironi L, Malavolta N, Martelli G, Poggioli G, Gozzetti G, and Miglioli M. Renal stone formation in patients with inflammatory bowel disease. *Scanning microscopy* 7: 371-379; discussion 379-380, 1993.
7. Coe F L, Evan A, and Worcester E. Kidney stone disease. *The Journal of clinical investigation* 115: 2598-2608, 2005.
8. Daniel S L, Hartman P A, and Allison M J. Microbial degradation of oxalate in the gastrointestinal tracts of rats. *Appl Environ Microbiol* 53: 1793-1797, 1987.
9. Danpure C J and Jennings P R. Peroxisomal alanine: glyoxylate aminotransferase deficiency in primary hyperoxaluria type I. *FEBS letters* 201: 20-24, 1986.
10. Dawson P A, Russell C S, Lee S, McLeay S C, van Dongen J M, Cowley D M, Clarke L A, and Markovich D. Urolithiasis and hepatotoxicity are linked to the anion transporter Sat1 in mice. *The Journal of clinical investigation* 120: 706-712, 2010.
11. Eisner B H, Porten S P, Bechis S K, and Stoller M L. Diabetic kidney stone formers excrete more oxalate and have lower urine pH than nondiabetic stone formers. *The Journal of urology* 183: 2244-2248, 2010.
12. Freel R W, Morozumi M, and Hatch M. Parsing apical oxalate exchange in Caco-2BBe1 monolayers: siRNA knockdown of SLC26A6 reveals the role and properties of PAT-1. *American journal of physiology* 297: G918-929, 2009.
13. Hassan H A, Cheng M, and Aronson P S. Cholinergic signaling inhibits oxalate transport by human intestinal T84 cells. *American journal of physiology Cell physiology* 302: C46-58, 2012.
14. Hatch M, Cornelius J, Allison M, Sidhu H, Peck A, and Freel R W. *Oxalobacter* sp. reduces urinary oxalate excretion by promoting enteric oxalate secretion. *Kidney international* 69: 691-698, 2006.
15. Hatch M and Freel R W. A human strain of *Oxalobacter* (HC-1) promotes enteric oxalate secretion in the small intestine of mice and reduces urinary oxalate excretion. *Urolithiasis*, 2013.
16. Hatch M and Freel R W. Intestinal transport of an obdurate anion: oxalate. *Urological research* 33: 1-16, 2005.
17. Hatch M, Gjymishka A, Salido E C, Allison M J, and Freel R W. Enteric oxalate elimination is induced and oxalate is normalized in a mouse model of primary hyperoxaluria following intestinal colonization with Oxalobacter. *American journal of physiology Gastrointestinal and liver physiology* 300: G461-469, 2011.
18. Hoppe B, Beck B, Gatter N, von Unruh G, Tischer A, Hesse A, Laube N, Kaul P, and Sidhu H. *Oxalobacter formigenes*: a potential tool for the treatment of primary hyperoxaluria type 1. *Kidney international* 70: 1305-1311, 2006.
19. Hoppe B, von Unruh G, Laube N, Hesse A, and Sidhu H. Oxalate degrading bacteria: new treatment option for patients with primary and secondary hyperoxaluria? *Urological research* 33: 372-375, 2005.
20. Jiang Z, Asplin J R, Evan A P, Rajendran V M, Velazquez H, Nottoli T P, Binder H J, and Aronson P S. Calcium oxalate urolithiasis in mice lacking anion transporter Slc26a6. *Nature genetics* 38: 474-478, 2006.
21. Jiang Z, Grichtchenko, I I, Boron W F, and Aronson P S. Specificity of anion exchange mediated by mouse Slc26a6. *The Journal of biological chemistry* 277: 33963-33967, 2002.
22. Langmead B, Trapnell C, Pop M, and Salzberg S L. Ultrafast and memory-efficient alignment of short DNA sequences to the human genome. *Genome biology* 10: R25, 2009.
23. Love M I, Huber W, and Anders S. Moderated estimation of fold change and dispersion for RNA-seq data with DESeq2. *Genome biology* 15: 550, 2014.

24. Mittl P R and Schneider-Brachert W. Sel1-like repeat proteins in signal transduction. *Cellular signalling* 19: 20-31, 2007.
25. Nelson W K, Houghton S G, Milliner D S, Lieske J C, and Sarr M G. Enteric hyperoxaluria, nephrolithiasis, and oxalate nephropathy: potentially serious and unappreciated complications of Roux-en-Y gastric bypass. *Surg Obes Relat Dis* 1: 481-485, 2005.
26. Pardi D S, Tremaine W J, Sandborn W J, and McCarthy J T. Renal and urologic complications of inflammatory bowel disease. *Am J Gastroenterol* 93: 504-514, 1998.
27. Robertson W G and Peacock M. The cause of idiopathic calcium stone disease: hypercalciuria or hyperoxaluria? *Nephron* 26: 105-110, 1980.
28. Salido E C, Li X M, Lu Y, Wang X, Santana A, Roy-Chowdhury N, Torres A, Shapiro L J, and Roy-Chowdhury J. Alanine-glyoxylate aminotransferase-deficient mice, a model for primary hyperoxaluria that responds to adenoviral gene transfer. *Proceedings of the National Academy of Sciences of the United States of America* 103: 18249-18254, 2006.
29. Sidhu H, Schmidt M E, Cornelius J G, Thamilselvan S, Khan S R, Hesse A, and Peck A B. Direct correlation between hyperoxaluria/oxalate stone disease and the absence of the gastrointestinal tract-dwelling bacterium *Oxalobacter formigenes*: possible prevention by gut recolonization or enzyme replacement therapy. *Journal of the American Society of Nephrology: JASN* 10 Suppl 14: S334-340, 1999.
30. Tao Y, Drabik K A, Waypa T S, Musch M W, Alverdy J C, Schneewind O, Chang E B, and Petrof E O. Soluble factors from *Lactobacillus* GG activate MAPKs and induce cytoprotective heat shock proteins in intestinal epithelial cells. *American journal of physiology* 290: C1018-1030, 2006.

The invention claimed is:

1. A method of stimulating oxalate transport in a mammalian subject in need, the method comprising administering to the subject an effective amount of a composition comprising one or more of purified proteins selected from SEQ ID NO: 8, SEQ ID NO: 12, SEQ ID NO: 14, SEQ ID NO: 16, SEQ OID NO: 18, SEQ ID NO: 20 and SEQ ID NO: 24.

2. The method of claim 1, wherein the mammalian subject is a human subject.

3. The method of claim 1, wherein the administering comprises oral administration, rectal administration, and/or injection.

4. The method of claim 1, wherein the composition further comprises one or more of purified proteins selected from SEQ ID NO: 2, SEQ ID NO: 4, SEQ ID NO: 6, SEQ ID NO: 10, SEQ ID NO: 22, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 101 and SEQ ID NO: 102.

* * * * *

```
                           SEQUENCE LISTING

<160> NUMBER OF SEQ ID NOS: 105

<210> SEQ ID NO 1
<211> LENGTH: 1572
<212> TYPE: DNA
<213> ORGANISM: Oxalobacter formigenes

<400> SEQUENCE: 1
atgtcgtccg tcattgctga ttcgcagcag cctgcagttt cagaagaaaa cgcaaataaa      60
attatccttg atgaggaaaa ggcggtcatc caatgtaacg aaagatataa gacggaaaat     120
gatgaaaagg gcgatgaaga aaccgtttca tggtgccgaa aagccgcgaa gtctggtaat     180
gcggaggcac aatatctttt tggcatgctg gtttatgatg gcagaggcgt gcagcaggat     240
aattgtgttg ccatgttatg gtggatgaaa gcagcagagc agaatcatgc caaggcactc     300
gttatgctgg gaaatcttca tcgtaaaggt cagtgcattg ctgagaatta tccgaaagcc     360
attgcctatt ggaagagagc tgctgttcag aataacgtat gggcatatca taatttaggg     420
acagcttatt acgatggtat cggtgtggat aaaaatcctc atgaagctgt tcgctggtgg     480
aagaaggcag ccgaattggg tttcctgaa tctcagaaca atctgggtgc tttatacaat      540
gatgggaatg gtgttgatcg tgattatcag gaggctgttt tctggtacag aaaaagtgcc     600
ctgcagggcg acgaattggg acagtacaat cttggggtgg cttattatta cggcagaggg     660
ataaaaaaag attttctga agcagtgtcg tggtacaaaa aatcagcaga acaagactat      720
gcacaagcac agcataatct tggtgttacg tattacgaag gtgagggaat aaaaaaagat     780
tacgccaagg ctgtgtactg gtggaaaaag gcagcagaac aggggattcc ccaatctcag     840
tataaccttg gcattgcata tgaagaaggc tggggcgctg aaaaaaaatcc ggagaatgct    900 gttttttggt acagaaaagc ggctgaacag ggacatgctg atgctcaaaa cagacttggc    960
atcgcttaca ggtatggaac cggagtcagg aaaaatcccg cattgtctgt caaatggctg   1020
gaaaagcgca caaagcaggg gcttgcaaga gcacagttca atttggggaa aaccttctat   1080
atcggagcag gcattaacaa gaatacagac aaagcggttt actggttcat aaaagctgcc   1140
aatcagggtt tcacagaagc acaggcttat attggtatga tttatttaa aggtaaatat     1200 gtcgccaaga acgaaaaaaa aggtttttac tggttaaaaa aagcagcaga aaaagacagt   1260
gctaaagcac aagcatttct tggcgcttta tacattgcag gaaatgaagt gaagccaaat   1320
ataaaggaag gcgttgcctt gacaaaaaaa gcggcattac agggtaatta cgaggcacaa   1380
```

```
accctgctcg gttttgcta cgagaatggc ttggaagtaa aaaaagacct gattgccgca    1440
tatgcgcttt acttgtcggc gtcacctcat ttcgattttg cagaaaaggc gcgtcttgat    1500
cttgaacgga aattaagcga acaggaaata gcaaaggcaa tatccgttaa tacagcaaaa    1560
ttgtttgagt ga                                                        1572
```

<210> SEQ ID NO 2
<211> LENGTH: 523
<212> TYPE: PRT
<213> ORGANISM: Oxalobacter formigenes

<400> SEQUENCE: 2

```
Met Ser Ser Val Ile Ala Asp Ser Gln Gln Pro Ala Val Ser Glu Glu
1               5                   10                  15

Asn Ala Asn Lys Ile Ile Leu Asp Glu Glu Lys Ala Val Ile Gln Cys
            20                  25                  30

Asn Glu Arg Tyr Lys Thr Glu Asn Asp Glu Lys Gly Asp Glu Glu Thr
        35                  40                  45

Val Ser Trp Cys Arg Lys Ala Ala Lys Ser Gly Asn Ala Glu Ala Gln
    50                  55                  60

Tyr Leu Phe Gly Met Leu Val Tyr Asp Gly Arg Gly Val Gln Gln Asp
65                  70                  75                  80

Asn Cys Val Ala Met Leu Trp Trp Met Lys Ala Ala Glu Gln Asn His
            85                  90                  95

Ala Lys Ala Leu Val Met Leu Gly Asn Leu His Arg Lys Gly Gln Cys
            100                 105                 110

Ile Ala Glu Asn Tyr Pro Lys Ala Ile Ala Tyr Trp Lys Arg Ala Ala
        115                 120                 125

Val Gln Asn Asn Val Trp Ala Tyr His Asn Leu Gly Thr Ala Tyr Tyr
    130                 135                 140

Asp Gly Ile Gly Val Asp Lys Asn Pro His Glu Ala Val Arg Trp Trp
145                 150                 155                 160

Lys Lys Ala Ala Glu Leu Gly Phe Pro Glu Ser Gln Asn Asn Leu Gly
            165                 170                 175

Ala Leu Tyr Asn Asp Gly Asn Gly Val Asp Arg Asp Tyr Gln Glu Ala
        180                 185                 190

Val Phe Trp Tyr Arg Lys Ser Ala Leu Gln Gly Asp Glu Leu Gly Gln
    195                 200                 205

Tyr Asn Leu Gly Val Ala Tyr Tyr Gly Arg Gly Ile Lys Lys Asp
210                 215                 220

Phe Ser Glu Ala Val Ser Trp Tyr Lys Lys Ser Ala Glu Gln Asp Tyr
225                 230                 235                 240

Ala Gln Ala Gln His Asn Leu Gly Val Thr Tyr Tyr Glu Gly Glu Gly
            245                 250                 255

Ile Lys Lys Asp Tyr Ala Lys Ala Val Tyr Trp Trp Lys Lys Ala Ala
            260                 265                 270

Glu Gln Gly Ile Pro Gln Ser Gln Tyr Asn Leu Gly Ile Ala Tyr Glu
        275                 280                 285

Glu Gly Trp Gly Ala Glu Lys Asn Pro Glu Asn Ala Val Phe Trp Tyr
    290                 295                 300

Arg Lys Ala Ala Glu Gln Gly His Ala Asp Ala Gln Asn Arg Leu Gly
305                 310                 315                 320

Ile Ala Tyr Arg Tyr Gly Thr Gly Val Arg Lys Asn Pro Ala Leu Ser
            325                 330                 335
```

-continued

```
Val Lys Trp Leu Glu Lys Ala Ala Lys Gln Gly Leu Ala Arg Ala Gln
            340                 345                 350

Phe Asn Leu Gly Lys Thr Phe Tyr Ile Gly Ala Gly Ile Asn Lys Asn
        355                 360                 365

Thr Asp Lys Ala Val Tyr Trp Phe Ile Lys Ala Ala Asn Gln Gly Phe
370                 375                 380

Thr Glu Ala Gln Ala Tyr Ile Gly Met Ile Tyr Phe Lys Gly Lys Tyr
385                 390                 395                 400

Val Ala Lys Asn Glu Lys Lys Gly Phe Tyr Trp Leu Lys Lys Ala Ala
                405                 410                 415

Glu Lys Asp Ser Ala Lys Ala Gln Ala Phe Leu Gly Ala Leu Tyr Ile
            420                 425                 430

Ala Gly Asn Glu Val Lys Pro Asn Ile Lys Glu Gly Val Ala Leu Thr
        435                 440                 445

Lys Lys Ala Ala Leu Gln Gly Asn Tyr Glu Ala Gln Thr Leu Leu Gly
    450                 455                 460

Phe Cys Tyr Glu Asn Gly Leu Glu Val Lys Lys Asp Leu Ile Ala Ala
465                 470                 475                 480

Tyr Ala Leu Tyr Leu Ser Ala Ser Pro His Phe Asp Phe Ala Glu Lys
                485                 490                 495

Ala Arg Leu Asp Leu Glu Arg Lys Leu Ser Glu Gln Glu Ile Ala Lys
            500                 505                 510

Ala Ile Ser Val Asn Thr Ala Lys Leu Phe Glu
        515                 520

<210> SEQ ID NO 3
<211> LENGTH: 687
<212> TYPE: DNA
<213> ORGANISM: Oxalobacter formigenes

<400> SEQUENCE: 3
atgaaaaatc gtttcgcgaa tgttgtcgat gctgtgatgc tggccttctt ggtttgcggg      60
ttttttgtgc ctgtgatggc tgtcgatacc ggttccgttt ccttttcgga tgagcgcaaa     120
aggcgcgatg cacaggaaga gaccatccgt attcaggaat cggttcaatt gctggacatg     180
gcggccagag aggggagcc gcaggccatg gtgttgctgg catgatgag cgatgtcggt     240 tttccggtaa agcgcgatct ggatcgtgcg attggctggt acgtcaaggc ggcggacaaa     300
cagtacggga aggcatggtt gccactggcg tttgcgtatg cggagatggg taacgatgtg     360
caggcggggt tctggtttga aaaagcggcc ggattgtatc gggaaacgaa tgcggatgat     420
gttctggtga tggttttcgg ggccgggtat ctggcggact atatcgggaa agaccagttt     480
gcacaaaggc aggaaatcaa caggaaacgc ctgatgtggc ttgaagggct tgccgcgtcg     540
ggtgatccgg tagcctgttc gatgatggcg acggtttatc gcgaggggct cggggtgaaa     600
aaggatgtca gacgcggcga tctctggtgc aaaaaggcag tgacgacaaa tcgggaaggg     660
atggtcgtgg aacggttctg ttattag                                          687

<210> SEQ ID NO 4
<211> LENGTH: 228
<212> TYPE: PRT
<213> ORGANISM: Oxalobacter formigenes

<400> SEQUENCE: 4

Met Lys Asn Arg Phe Ala Asn Val Val Asp Ala Val Met Leu Ala Phe
1               5                   10                  15
```

```
Leu Val Cys Gly Phe Phe Val Pro Val Met Ala Val Asp Thr Gly Ser
             20                  25                  30
Val Ser Phe Ser Asp Glu Arg Lys Arg Arg Asp Ala Gln Glu Glu Thr
         35                  40                  45
Ile Arg Ile Gln Glu Ser Val Gln Leu Leu Asp Met Ala Ala Arg Glu
 50                  55                  60
Gly Glu Pro Gln Ala Met Val Leu Leu Gly Met Met Ser Asp Val Gly
 65                  70                  75                  80
Phe Pro Val Lys Arg Asp Leu Asp Arg Ala Ile Gly Trp Tyr Val Lys
                 85                  90                  95
Ala Ala Asp Lys Gln Tyr Gly Lys Ala Trp Leu Pro Leu Ala Phe Ala
            100                 105                 110
Tyr Ala Glu Met Gly Asn Asp Val Gln Ala Gly Phe Trp Phe Glu Lys
        115                 120                 125
Ala Ala Gly Leu Tyr Arg Glu Thr Asn Ala Asp Asp Val Leu Val Met
    130                 135                 140
Val Phe Gly Ala Gly Tyr Leu Asp Tyr Ile Gly Lys Asp Gln Phe
145                 150                 155                 160
Ala Gln Arg Gln Glu Ile Asn Arg Lys Arg Leu Met Trp Leu Glu Gly
                165                 170                 175
Leu Ala Ala Ser Gly Asp Pro Val Ala Cys Ser Met Met Ala Thr Val
            180                 185                 190
Tyr Arg Glu Gly Leu Gly Val Lys Lys Asp Val Arg Arg Gly Asp Leu
        195                 200                 205
Trp Cys Lys Lys Ala Val Thr Thr Asn Arg Gly Met Val Val Glu
    210                 215                 220
Arg Phe Cys Tyr
225

<210> SEQ ID NO 5
<211> LENGTH: 1920
<212> TYPE: DNA
<213> ORGANISM: Oxalobacter formigenes

<400> SEQUENCE: 5
atgaagtcag tttcgcatat gggttttat cgtttcaaaa gttttgtttt ttcagttgtc        60 gttttgcgg cagggtgtgc atgggtaccg tctgtgtcgt ttgccgggca aaaggatgat       120
tgcgcctctg tcgggtgttc cgatacgacg gtacaaaagg acggggatct ggaaaaaatc       180
aggcaaaagg cgcagcaggg cgatgcaaat gcgcagatgg cactgggttt gcgttacctg       240
atggggaacg gccttgccgc agatgaggtt ctcgcgcagg aatggttttt gaagtcggca       300
cagcaaaata tgtggtggcg caggtggcg ctggcgacga tgctggcttt cgagagtgac       360
aggcaggatc tgcccgcggc ggcgatgtgg ttttcaaagg cggctgatgc cggaaacgtt       420
caggcgatgt cggagctggt acgtctttac gagacgggca gtggtgtgac acgcgatatg       480
gcgaaagccg aagaatggcg agtccgcgca aaaatgcgca gtgatgccgt caagctggag       540
cgggtgtgga aaatcgctct ggccgataag gcgcggtgga tgaggaaaac gtcacgaccg       600
gtggagcttg ccgctcagga tggcgttgcc acaacagcgg caaggattga tgtcgttgcg       660
ttgaagaagg cggctgaaaa cggtgacgat catgcccaaa ccttgcttgg tgctttgctg       720
gccactggcg acggggtgaa aaaggatgag aaagccgcga tcggctggtt tgaaaaagcg       780
gcggattcgg gcaatactca ggcgcaggct gttctggggg aactttatgg attgggctgg       840
ggtggcttga agaaggacga ggcgaaggcg gccaaatgga tggagaaggc ggcgctgggc       900
```

-continued

```
ggtctggttg ctgcaaaggc ggcgtggggc tcgatgctct cgcaaggtaa agggtggaa      960
aaggacccga aaaaggtct tgaatggttt gttcaggcgg ccaggacgg tgatggacgt     1020
acccgtctgt tgatggggat gatgttgatc catcagaacc gggatgcggc cgcacaatgg    1080
ttttatggtg cggctgaggt tggcgatgaa gaggtgcttt ccgctttggg aacgttttac    1140
ggctggggaa acggcccggt gctggatgaa agcgagaagc tttccgaggt acgccgttat    1200
gcccagcggg acgagtccga ggcgcagcag atgatgggtt tctgtatgg cgaaggctgg    1260
ggtgcaaagc gtgatcctgt aaaggcggaa tactggtttg acaaggcagc tgccagcggc    1320
gatgtggaag tgtggttgcc gcttgggctg ttgtatgccg aaacggggcg tgacgatatg    1380
gcagcggccg cttttgccaa ggcggtggct tcgggcggtt tcgggctggc caatgacggg    1440
gagttgcttc agctgatttt cgtcgattcg gagaagatgc cggatgtggg gaatgccctg    1500
aaacgtccgg cttcggcaaa aaaaacggct tccggtgcca agagccgaa tggggaaaa    1560
aaggctggcg taaacgacaa ggacgggtt gccagtgatg aacggcttgt ccgcgtggcg    1620
aagaaacggg cttttgttct ggccgaagcg aaaaagggca atccggctgc gcagttgatg    1680
atggcccgta ttctgaaaga aggttggggg gtgaagaagg atgaggaggc agcagcgtct    1740
ttgcgtgctg acggtatcag ggggatgtgt gctgccctga aggacaaggc ggaggaagag    1800
cctttatgtt cgaatgaagg ggacggtgga acggtggcg ttttgccgga tgccgcttca    1860
gtcgacaagg cggatgtgaa tgattcgacg gtgtttaagg cgagacagga gatgaactga    1920
```

<210> SEQ ID NO 6
<211> LENGTH: 639
<212> TYPE: PRT
<213> ORGANISM: Oxalobacter formigenes

<400> SEQUENCE: 6

```
Met Lys Ser Val Ser His Met Gly Phe Tyr Arg Phe Lys Ser Phe Val
  1               5                  10                  15

Phe Ser Val Val Val Phe Ala Ala Gly Cys Ala Trp Val Pro Ser Val
                 20                  25                  30

Ser Phe Ala Gly Gln Lys Asp Asp Cys Ala Ser Val Gly Cys Ser Asp
             35                  40                  45

Thr Thr Val Gln Lys Asp Gly Asp Leu Glu Lys Ile Arg Gln Lys Ala
         50                  55                  60

Gln Gln Gly Asp Ala Asn Ala Gln Met Ala Leu Gly Leu Arg Tyr Leu
 65                  70                  75                  80

Met Gly Asn Gly Leu Ala Ala Asp Glu Val Leu Ala Gln Glu Trp Phe
                 85                  90                  95

Leu Lys Ser Ala Gln Gln Asn Asn Val Val Ala Gln Val Ala Leu Ala
                100                 105                 110

Thr Met Leu Ala Phe Glu Ser Asp Arg Gln Asp Leu Pro Ala Ala Ala
            115                 120                 125

Met Trp Phe Ser Lys Ala Ala Asp Ala Gly Asn Val Gln Ala Met Ser
        130                 135                 140

Glu Leu Val Arg Leu Tyr Glu Thr Gly Ser Gly Val Thr Arg Asp Met
145                 150                 155                 160

Ala Lys Ala Glu Glu Trp Arg Val Arg Ala Lys Met Arg Ser Asp Ala
                165                 170                 175

Val Lys Leu Glu Arg Val Trp Lys Ile Ala Leu Ala Asp Lys Ala Arg
            180                 185                 190
```

-continued

```
Trp Met Arg Lys Thr Ser Arg Pro Val Glu Leu Ala Ala Gln Asp Gly
            195                 200                 205

Val Ala Thr Thr Ala Ala Arg Ile Asp Val Val Ala Leu Lys Lys Ala
    210                 215                 220

Ala Glu Asn Gly Asp Asp His Ala Gln Thr Leu Leu Gly Ala Leu Leu
225                 230                 235                 240

Ala Thr Gly Asp Gly Val Lys Lys Asp Glu Lys Ala Ala Ile Gly Trp
                245                 250                 255

Phe Glu Lys Ala Ala Asp Ser Gly Asn Thr Gln Ala Gln Ala Val Leu
                260                 265                 270

Gly Glu Leu Tyr Gly Leu Gly Trp Gly Gly Leu Lys Lys Asp Glu Ala
            275                 280                 285

Lys Ala Ala Lys Trp Met Glu Lys Ala Ala Leu Gly Gly Leu Val Ala
        290                 295                 300

Ala Lys Ala Ala Trp Gly Ser Met Leu Ser Gln Gly Lys Gly Val Glu
305                 310                 315                 320

Lys Asp Pro Lys Lys Gly Leu Glu Trp Phe Val Gln Ala Gly Gln Asp
                325                 330                 335

Gly Asp Gly Arg Thr Arg Leu Leu Met Gly Met Met Leu Ile His Gln
            340                 345                 350

Asn Arg Asp Ala Ala Ala Gln Trp Phe Tyr Gly Ala Ala Glu Val Gly
        355                 360                 365

Asp Glu Glu Val Leu Ser Ala Leu Gly Thr Phe Tyr Gly Trp Gly Asn
    370                 375                 380

Gly Pro Val Leu Asp Glu Ser Glu Lys Leu Ser Glu Val Arg Arg Tyr
385                 390                 395                 400

Ala Gln Arg Asp Glu Ser Glu Ala Gln Gln Met Met Gly Phe Leu Tyr
                405                 410                 415

Gly Glu Gly Trp Gly Ala Lys Arg Asp Pro Val Lys Ala Glu Tyr Trp
            420                 425                 430

Phe Asp Lys Ala Ala Ser Gly Asp Val Glu Val Trp Leu Pro Leu
        435                 440                 445

Gly Leu Leu Tyr Ala Glu Thr Gly Arg Asp Asp Met Ala Ala Ala Ala
    450                 455                 460

Phe Ala Lys Ala Val Ala Ser Gly Gly Phe Gly Leu Ala Asn Asp Gly
465                 470                 475                 480

Glu Leu Leu Gln Leu Ile Phe Val Asp Ser Glu Lys Met Pro Asp Val
                485                 490                 495

Gly Asn Ala Leu Lys Arg Pro Ala Ser Ala Lys Lys Thr Ala Ser Gly
            500                 505                 510

Ala Lys Glu Pro Asn Gly Gly Lys Lys Ala Gly Val Asn Asp Lys Asp
        515                 520                 525

Gly Val Ala Ser Asp Glu Arg Leu Val Arg Val Ala Lys Lys Arg Ala
    530                 535                 540

Phe Val Leu Ala Glu Ala Lys Lys Gly Asn Pro Ala Ala Gln Leu Met
545                 550                 555                 560

Met Ala Arg Ile Leu Lys Glu Gly Trp Gly Val Lys Lys Asp Glu Glu
                565                 570                 575

Ala Ala Ala Ser Leu Arg Ala Asp Gly Ile Arg Gly Met Cys Ala Ala
            580                 585                 590

Leu Lys Asp Lys Ala Glu Glu Glu Pro Leu Cys Ser Asn Glu Gly Asp
        595                 600                 605

Gly Gly Asn Gly Gly Val Leu Pro Asp Ala Ala Ser Val Asp Lys Ala
```

```
                610               615               620
Asp Val Asn Asp Ser Thr Val Phe Lys Ala Arg Gln Glu Met Asn
625                 630               635

<210> SEQ ID NO 7
<211> LENGTH: 456
<212> TYPE: DNA
<213> ORGANISM: Oxalobacter formigenes

<400> SEQUENCE: 7
atggctttgg cggatggggc ggctgctccg gtggcagtga cgtcttatgc gcagcagccg    60
ttgaagctgg tgcaggaaaa ggcttctgac ggggatgggt ctgccgaact gaactgggt   120 ttgcggtatg ttttcggctc tgacggggtc aaaaatgtgc cgctcggggt tcctggatc   180 aataaggcgg ctctaaaggg tattccgcag gcggagcatg agatgggtc gctgtatctg   240 atggggattg gcgttgccca agcaatgtg atggctgtgg cctggtacag gaaggcggca   300
attcagggtt acgccccgtc gcaaacggcg atggggtatg cgtatgaaga ggggccgggg   360
gtgccacagg atgcggatct ggcccgttac tggtttgaca aggcggcggc acagggaaat   420
ggtattgccg tggaaagcct tgaaggaggg atgtag                            456

<210> SEQ ID NO 8
<211> LENGTH: 151
<212> TYPE: PRT
<213> ORGANISM: Oxalobacter formigenes

<400> SEQUENCE: 8

Met Ala Leu Ala Asp Gly Ala Ala Ala Pro Val Ala Val Thr Ser Tyr
1               5                  10                  15

Ala Gln Gln Pro Leu Lys Leu Val Gln Glu Lys Ala Ser Asp Gly Asp
                20                  25                  30

Gly Ser Ala Glu Leu Glu Leu Gly Leu Arg Tyr Val Phe Gly Ser Asp
            35                  40                  45

Gly Val Lys Asn Val Pro Leu Gly Val Ser Trp Ile Asn Lys Ala Ala
        50                  55                  60

Leu Lys Gly Ile Pro Gln Ala Glu His Glu Met Gly Ser Leu Tyr Leu
65                  70                  75                  80

Met Gly Ile Gly Val Ala Gln Ser Asn Val Met Ala Val Ala Trp Tyr
                85                  90                  95

Arg Lys Ala Ala Ile Gln Gly Tyr Ala Pro Ser Gln Thr Ala Met Gly
                100                 105                 110

Tyr Ala Tyr Glu Glu Gly Ala Gly Val Pro Gln Asp Ala Asp Leu Ala
            115                 120                 125

Arg Tyr Trp Phe Asp Lys Ala Ala Gln Gly Asn Gly Ile Ala Val
        130                 135                 140

Glu Ser Leu Glu Gly Gly Met
145                 150

<210> SEQ ID NO 9
<211> LENGTH: 1470
<212> TYPE: DNA
<213> ORGANISM: Oxalobacter formigenes

<400> SEQUENCE: 9
atgaaaagac gggttttgta tggtgtgctg tttgcggtgc tggcggggtg ttctgccggt    60
gcgttggcgt ccgtgtccgg cttgtcggat gggctggcgc agcttgaacg gaggcagttc   120
```

```
gaatcggctt atgcgacgct catgccggag gcggagaagg ggaatccccg tgcggcgctg      180
gaggtgggga agctgctgtt gacggggcgc ggggtggcaa aggatgaagc ggcggcggtg      240
aagtggcttc tggtggcggc ggatagtggc aaccgggatg cgcagtatat gctgggggcg      300
atgtcggtgg aggggatcgg tctgccgaag gattctcagg tggcgttgac ctggctgtcg      360
aaggcggcgg cgcaggggga tgcgcgtgcg aagacggctt tggggattct gatgcagtcc      420
gccgggccgg gatcgcagca tacggaacag gcagcccggt ggttcgagag gcggcggcg       480 tcagggggaac cggaggcgca acggcgctgg gcgctgatgc tggcgtctgg ccgggggggtg    540 gccaaaaatg agggtgaggc actgaaatgg tttaagaagg cggctgtcgc ggggggatgtg    600 gaagcgcagc gcaatctggg gattatgctc tcgacggaa  aggggggtgac gggcggcaag    660 ccggattttg cggaagcggc acgctggtac ggcctggcag cgaagaaggg ggatgcgaag    720
gcgcagtatg ggttgggcat tttgtatgcg aagggggcagg gggtggcgcc cgatcaggaa    780
aaggcgctga ttctgtatcg catggcggcg actcaggggc tggcgacggc ggagtatgcc     840
gtcgggctgg cgtatgcgta tggacggggg acggcacaaa atgatgtgaa ggcggccgac     900
tggttcgagg cggcgcgca gcaggggtg gtgcgtgcgc aatataatct cgctctgatg       960
ctggaggcgg tcgcggtcg gcctgtggat acggtggcgg cgagcaagtg gttttttgatg    1020 gcggcggaga agggcttgcg ggaggcacaa tacaatatgg ggtatcacta tgccgagggg    1080
aaaggggtgc cacgcgatca gggcaaggcg gtgttctggt atgaaaaggc ggcggctgcc    1140
ggggatgtga aggcccagta caatctgggg atgctgtatc tgaacggggt taatggcaag    1200
gcggatgacg aaaaggcggc ttttttctac cggatggcgg ccggggcggg atatggcccg    1260
gcgatgtacc ggctggcggt gttgtatgag gaaggccgtg gggtaaagca gagttatcag    1320
ctggcagggg aatggtatga gcgggcggat ctggccgcga agtgaagat tgacgaggcg     1380 atgaaaaaga atccgcatcc gtttgtgcaa cggactctgc aggtgccgga tgatttgaat    1440
caatcttcag ataaattggc gggacattag                                      1470
```

<210> SEQ ID NO 10
<211> LENGTH: 489
<212> TYPE: PRT
<213> ORGANISM: Oxalobacter formigenes

<400> SEQUENCE: 10

```
Met Lys Arg Arg Val Leu Tyr Gly Val Leu Phe Ala Val Leu Ala Gly
1               5                   10                  15

Cys Ser Ala Gly Ala Leu Ala Ser Val Ser Gly Leu Ser Asp Gly Leu
            20                  25                  30

Ala Gln Leu Glu Arg Arg Gln Phe Glu Ser Ala Tyr Ala Thr Leu Met
        35                  40                  45

Pro Glu Ala Glu Lys Gly Asn Pro Arg Ala Ala Leu Glu Val Gly Lys
    50                  55                  60

Leu Leu Leu Thr Gly Arg Gly Val Ala Lys Asp Glu Ala Ala Val
65                  70                  75                  80

Lys Trp Leu Leu Val Ala Ala Asp Ser Gly Asn Arg Asp Ala Gln Tyr
                85                  90                  95

Met Leu Gly Ala Met Ser Val Glu Gly Ile Gly Leu Pro Lys Asp Ser
            100                 105                 110

Gln Val Ala Leu Thr Trp Leu Ser Lys Ala Ala Gln Gly Asp Ala
        115                 120                 125

Arg Ala Lys Thr Ala Leu Gly Ile Leu Met Gln Ser Ala Gly Pro Gly
```

```
                    130                 135                 140
Ser Gln His Thr Glu Gln Ala Ala Arg Trp Phe Glu Arg Ala Ala
145                 150                 155                 160

Ser Gly Glu Pro Glu Ala Gln Arg Arg Trp Ala Leu Met Leu Ala Ser
                165                 170                 175

Gly Arg Gly Val Ala Lys Asn Glu Gly Ala Leu Lys Trp Phe Lys
                180                 185                 190

Lys Ala Ala Val Ala Gly Asp Val Glu Ala Gln Arg Asn Leu Gly Ile
                195                 200                 205

Met Leu Ser Thr Gly Lys Gly Val Thr Gly Lys Pro Asp Phe Ala
            210                 215                 220

Glu Ala Ala Arg Trp Tyr Gly Leu Ala Ala Lys Lys Gly Asp Ala Lys
225                 230                 235                 240

Ala Gln Tyr Gly Leu Gly Ile Leu Tyr Ala Lys Gly Gln Gly Val Ala
                245                 250                 255

Pro Asp Gln Glu Lys Ala Leu Ile Leu Tyr Arg Met Ala Ala Thr Gln
                260                 265                 270

Gly Leu Ala Thr Ala Glu Tyr Ala Val Gly Leu Ala Tyr Ala Tyr Gly
            275                 280                 285

Arg Gly Thr Ala Gln Asn Asp Val Lys Ala Ala Asp Trp Phe Glu Ala
290                 295                 300

Ala Ala Gln Gln Gly Val Val Arg Ala Gln Tyr Asn Leu Ala Leu Met
305                 310                 315                 320

Leu Glu Ala Gly Arg Gly Arg Pro Val Asp Thr Val Ala Ala Ser Lys
                325                 330                 335

Trp Phe Leu Met Ala Ala Glu Lys Gly Leu Arg Glu Ala Gln Tyr Asn
            340                 345                 350

Met Gly Tyr His Tyr Ala Glu Gly Lys Gly Val Pro Arg Asp Gln Gly
                355                 360                 365

Lys Ala Val Phe Trp Tyr Glu Lys Ala Ala Ala Gly Asp Val Lys
            370                 375                 380

Ala Gln Tyr Asn Leu Gly Met Leu Tyr Leu Asn Gly Val Asn Gly Lys
385                 390                 395                 400

Ala Asp Asp Glu Lys Ala Ala Phe Phe Tyr Arg Met Ala Ala Gly Ala
                405                 410                 415

Gly Tyr Gly Pro Ala Met Tyr Arg Leu Ala Val Leu Tyr Glu Glu Gly
            420                 425                 430

Arg Gly Val Lys Gln Ser Tyr Gln Leu Ala Gly Glu Trp Tyr Glu Arg
            435                 440                 445

Ala Asp Leu Ala Ala Lys Val Lys Ile Asp Glu Ala Met Lys Lys Asn
450                 455                 460

Pro His Pro Phe Val Gln Arg Thr Leu Gln Val Pro Asp Asp Leu Asn
465                 470                 475                 480

Gln Ser Ser Asp Lys Leu Ala Gly His
                485

<210> SEQ ID NO 11
<211> LENGTH: 1206
<212> TYPE: DNA
<213> ORGANISM: Oxalobacter formigenes

<400> SEQUENCE: 11
atgaaaaaag gggttgcgtt cgcgctggtg gctcttggga gcatactggt ttgtacggcc    60
ttggccggaa gcgaaagaa actggacgcc ttgctggcga tgccggtgaa agagacaaag   120
```

```
gtttttgtcg aatcgaatga agagccgttg tttgtgatgt tgaaaagctc gttgtccgaa    180
gagacggatg aaactgtcgg gaagccggtt gtttcggaaa agacggcaga gccgggacaa    240
gacaatgacg gtgaaacagg gggagcctgg atgcagcagc tgcggcatca ggcggatcag    300
ggggatgcga atccgctttt ctggctgggc cggttcacgg ttgaggacag ccgggacggg    360
aaaacgattg acgagggcat ccgtctgatc cggcgttctg ccgaaggggg attcgtgcgg    420
gcacaattgt atctcggcac gctgtatgcc aatgggactc atgtgaaggc tgacccgcac    480
gaggcggaaa aatggctttc cagggccgca gggcaaggtt ctccgatggt tcagctttat    540
ctcggcctga tgtatggtca tggcaagggg gttccccgtg acttgaacaa gtcgcttttc    600
tgggtggaaa aggcggcgga caggggcttg ccgcatgcgc agctggcgcg tgggcttttt    660
gcgtcgtttt cccattatta tccccgggat gatgaaaagg ccgtgctgta tctgacgaaa    720
gcggcaaagc aggggatgcc gatggcccag ttttatctgg cgctgatgta tcagcgtggc    780
cggggtgtcg aacagagtaa cgagcaggcc ttgcactgga atatgctggc ggcggaacag    840
ggctatccgg atgccgagta tgcgatgtcg cggatggcgg aactcggtat cggggtgacg    900
gccgataagg catggagcat gatgtggctg atcgtgccg cccatcacgg atgccgctg     960
gcgcaatatt tgatgggcat ggcctatctg aaggaaaat cggtcccgca ggacttgcct    1020
gttgcggcgg catggtttta caaggcggcg atgcagggaa atgccgatgc ccagttgcga    1080
ctcggttata tgtatgccag gggaatcggt gttcctgtgg acaagccgaa ggcggttgcc    1140
tggcttgaaa aggccgcttc ggctggcaat acggtggccg ggcagtggct gaaacaactg    1200
gattga                                                              1206
```

<210> SEQ ID NO 12
<211> LENGTH: 401
<212> TYPE: PRT
<213> ORGANISM: Oxalobacter formigenes

<400> SEQUENCE: 12

```
Met Lys Lys Gly Val Ala Phe Ala Leu Val Ala Leu Gly Ser Ile Leu
1               5                   10                  15

Val Cys Thr Ala Leu Ala Gly Ser Glu Lys Lys Leu Asp Ala Leu Leu
            20                  25                  30

Ala Met Pro Val Lys Glu Thr Lys Val Phe Val Glu Ser Asn Glu Glu
        35                  40                  45

Pro Leu Phe Val Met Leu Lys Ser Ser Leu Ser Glu Glu Thr Asp Glu
    50                  55                  60

Thr Val Gly Lys Pro Val Val Ser Glu Lys Thr Ala Glu Pro Gly Gln
65                  70                  75                  80

Asp Asn Asp Gly Glu Thr Gly Gly Ala Trp Met Gln Gln Leu Arg His
                85                  90                  95

Gln Ala Asp Gln Gly Asp Ala Lys Ser Ala Phe Trp Leu Gly Arg Phe
            100                 105                 110

Thr Val Glu Asp Ser Arg Asp Gly Lys Thr Ile Asp Glu Gly Ile Arg
        115                 120                 125

Leu Ile Arg Arg Ser Ala Glu Gly Gly Phe Val Arg Ala Gln Leu Tyr
    130                 135                 140

Leu Gly Thr Leu Tyr Ala Asn Gly Thr His Val Lys Ala Asp Pro His
145                 150                 155                 160

Glu Ala Glu Lys Trp Leu Ser Arg Ala Ala Gly Gln Gly Ser Pro Met
                165                 170                 175
```

Val Gln Leu Tyr Leu Gly Leu Met Tyr Gly His Gly Lys Gly Val Pro
                180                 185                 190

Arg Asp Leu Asn Lys Ser Leu Phe Trp Val Glu Lys Ala Ala Asp Arg
                195                 200                 205

Gly Leu Pro His Ala Gln Leu Ala Arg Gly Leu Phe Ala Ser Phe Ser
    210                 215                 220

His Tyr Tyr Pro Arg Asp Asp Glu Lys Ala Val Leu Tyr Leu Thr Lys
225                 230                 235                 240

Ala Ala Lys Gln Gly Met Pro Met Ala Gln Phe Tyr Leu Ala Leu Met
                245                 250                 255

Tyr Gln Arg Gly Arg Gly Val Glu Gln Ser Asn Glu Gln Ala Leu His
                260                 265                 270

Trp Asn Met Leu Ala Ala Glu Gln Gly Tyr Pro Asp Ala Glu Tyr Ala
                275                 280                 285

Met Ser Arg Met Ala Glu Leu Gly Ile Gly Val Thr Ala Asp Lys Ala
                290                 295                 300

Trp Ser Met Met Trp Leu Asp Arg Ala Ala His His Gly Met Pro Leu
305                 310                 315                 320

Ala Gln Tyr Leu Met Gly Met Ala Tyr Leu Glu Gly Lys Ser Val Pro
                325                 330                 335

Gln Asp Leu Pro Val Ala Ala Ala Trp Phe Tyr Lys Ala Ala Met Gln
                340                 345                 350

Gly Asn Ala Asp Ala Gln Leu Arg Leu Gly Tyr Met Tyr Ala Arg Gly
                355                 360                 365

Ile Gly Val Pro Val Asp Lys Pro Lys Ala Val Ala Trp Leu Glu Lys
                370                 375                 380

Ala Ala Ser Ala Gly Asn Thr Val Ala Gly Gln Trp Leu Lys Gln Leu
385                 390                 395                 400

Asp

<210> SEQ ID NO 13
<211> LENGTH: 900
<212> TYPE: DNA
<213> ORGANISM: Oxalobacter formigenes

<400> SEQUENCE: 13

```
atgaagaaaa ccatctatca attcgcactt attttatta ccttaagttt tttaacggcg      60
tgtacaggca atattgattc ggaaagcgaa aataaaggta ttcaacatta taaaaatggg     120
gaatatcaaa aagcaattcc cttattggag aaagctgaag atggcggcag ttccagtgcc     180
gcattctatc ttggagaaat atttcgtaaa ggtgaaggcg ttaatcaaga ttttgggaga     240
tcatgtacgc attatataaa atcagcaaaa ggtggtaata acaatgccta tttactggcc     300
ggttcgtgtt tcgtaatggg aaaaggtgtg aagcaggatt ttgcagaagc attgaaatgg     360
tttaaaaaag cgtccgatga agtgaaaaa actgatttga ctgaatctga caagaaatat     420
ttaacgcgat cattggccac aatgtactat tccggaaaag gaaccctgca agacttcagc     480
gaagccgcaa gtgggcgga aaagcggct gaactgggtg atgcgaattc acaggcggtt      540
atggcgttcc tgctttatac ggggcagggc gttctggctg acaggaaggc tgcccggata     600
tgggcgcaaa atcagcgga tcagggaaac gatctggggg aagtcctgat gggtgtattc     660
aatcaatatg ctgattcccc ggacatgaaa gcggcctttg actggtatga gaaatcggca     720
aaacagggca acccggccgc gcagtatcaa ttgggaacgt tttatgaaga aggcattatt     780
```

```
gttcctgaag acattgaaaa agcccacgct tgttataaac aggcggccga tagcaaaaag      840
tcggatactc tggtcaaggc tctgatggat ttcgaggcgc gacagaaaaa acagaaatga      900
```

<210> SEQ ID NO 14
<211> LENGTH: 299
<212> TYPE: PRT
<213> ORGANISM: Oxalobacter formigenes

<400> SEQUENCE: 14

```
Met Lys Lys Thr Ile Tyr Gln Phe Ala Leu Ile Phe Ile Thr Leu Ser
1               5                   10                  15

Phe Leu Thr Ala Cys Thr Gly Asn Ile Asp Ser Glu Ser Glu Asn Lys
            20                  25                  30

Gly Ile Gln His Tyr Lys Asn Gly Glu Tyr Gln Lys Ala Ile Pro Leu
        35                  40                  45

Leu Glu Lys Ala Glu Asp Gly Ser Ser Ser Ala Ala Phe Tyr Leu
    50                  55                  60

Gly Glu Ile Phe Arg Lys Gly Glu Gly Val Asn Gln Asp Phe Gly Arg
65                  70                  75                  80

Ser Cys Thr His Tyr Ile Lys Ser Ala Lys Gly Gly Asn Asn Asn Ala
                85                  90                  95

Tyr Leu Leu Ala Gly Ser Cys Phe Val Met Gly Lys Gly Val Lys Gln
            100                 105                 110

Asp Phe Ala Glu Ala Leu Lys Trp Phe Lys Ala Ser Asp Glu Ser
        115                 120                 125

Glu Lys Thr Asp Leu Thr Glu Ser Asp Lys Lys Tyr Leu Thr Arg Ser
130                 135                 140

Leu Ala Thr Met Tyr Tyr Ser Gly Lys Gly Thr Leu Gln Asp Phe Ser
145                 150                 155                 160

Glu Ala Ala Lys Trp Ala Glu Lys Ala Ala Glu Leu Gly Asp Ala Asn
                165                 170                 175

Ser Gln Ala Val Met Ala Phe Leu Leu Tyr Thr Gly Gln Gly Val Leu
            180                 185                 190

Ala Asp Arg Lys Ala Ala Arg Ile Trp Ala Gln Lys Ser Ala Asp Gln
        195                 200                 205

Gly Asn Asp Leu Gly Glu Val Leu Met Gly Val Phe Asn Gln Tyr Ala
    210                 215                 220

Asp Ser Pro Asp Met Lys Ala Ala Phe Asp Trp Tyr Glu Lys Ser Ala
225                 230                 235                 240

Lys Gln Gly Asn Pro Ala Ala Gln Tyr Gln Leu Gly Thr Phe Tyr Glu
                245                 250                 255

Glu Gly Ile Ile Val Pro Glu Asp Ile Glu Lys Ala His Ala Cys Tyr
            260                 265                 270

Lys Gln Ala Ala Asp Ser Lys Lys Ser Asp Thr Leu Val Lys Ala Leu
        275                 280                 285

Met Asp Phe Glu Ala Arg Gln Lys Lys Gln Lys
    290                 295
```

<210> SEQ ID NO 15
<211> LENGTH: 918
<212> TYPE: DNA
<213> ORGANISM: Oxalobacter formigenes

<400> SEQUENCE: 15

```
atgtcaaaac agggtgacag gagaaggaca gggatgaaga tgtcgggttt cagatttgcg      60
```

-continued

```
ttgggggtgt cggtatgtct gttgacggta tgggttccag cgacgtctat ggcaggaaac      120
gtgtcggcgt cggcatatca gatgtctcaa ggcgaagacg aagcatggac gttttatcgt      180
accggacagt acgggaaggc actggccgct ttcaggggggc tggagacgaa aggggatgtt     240
gccgccttgt atggactggg tgtgatggcg acgaatggtc tcggtatgcc cgtaatgat       300 gaaaaggcgc tggtatggtt tagggaaggg gcggcaaaag gctcgcgtga ggcgcaattc      360
gggctggggg cgatgtacga tttgagtcgc ggtgtccggc aggatatgac gctggcgatc      420
gactggtatg aaaagtcggc gagagcggga tatgcgccgg ctctgacgcg gctgggcagg      480
atgaatttgc tggggagggg gatgtcccgc aattatggga aggcgttccg gttttttcaaa    540 cagtcggcac agcgtgggga tagggacggt gagttttatt tcgggatgat gtttatccgt     600
ggctggggga cgaagcggga tgtggaagag gcggctggct ggatcagaaa ggcggcggag     660
aagggacagc cggaagcgat gcgggtgatg tcgaccttgt atgagggtgg ttatggcgtt     720
gcccaaagtg agaaagatgc gctcgtctgg ctgaaaaaga gcgttgatgc gggcgacagg     780
gaagcgatga ggcggctggc agcggtgtat gaaaacggca cgttcggtgt gacgccggac     840
aaggagaagg cccgtttgct gaaaaagaag gcagccgagg tgaaaaaggc tgttttttccg    900 gattatgccg tgatgtag                                                   918
```

<210> SEQ ID NO 16
<211> LENGTH: 305
<212> TYPE: PRT
<213> ORGANISM: Oxalobacter formigenes

<400> SEQUENCE: 16

```
Met Ser Lys Gln Gly Asp Arg Arg Thr Gly Met Lys Met Ser Gly
1               5                   10                  15

Phe Arg Phe Ala Leu Gly Val Ser Val Cys Leu Leu Thr Val Trp Val
                20                  25                  30

Pro Ala Thr Ser Met Ala Gly Asn Val Ser Ala Ser Ala Tyr Gln Met
            35                  40                  45

Ser Gln Gly Glu Asp Glu Ala Trp Thr Phe Tyr Arg Thr Gly Gln Tyr
        50                  55                  60

Gly Lys Ala Leu Ala Ala Phe Arg Gly Leu Glu Thr Lys Gly Asp Val
65                  70                  75                  80

Ala Ala Leu Tyr Gly Leu Gly Val Met Ala Thr Asn Gly Leu Gly Met
                85                  90                  95

Pro Arg Asn Asp Glu Lys Ala Leu Val Trp Phe Arg Glu Gly Ala Ala
            100                 105                 110

Lys Gly Ser Arg Glu Ala Gln Phe Gly Leu Gly Ala Met Tyr Asp Leu
        115                 120                 125

Ser Arg Gly Val Arg Gln Asp Met Thr Leu Ala Ile Asp Trp Tyr Glu
    130                 135                 140

Lys Ser Ala Arg Ala Gly Tyr Ala Pro Ala Leu Thr Arg Leu Gly Arg
145                 150                 155                 160

Met Asn Leu Leu Gly Arg Gly Met Ser Arg Asn Tyr Gly Lys Ala Phe
                165                 170                 175

Arg Phe Phe Lys Gln Ser Ala Gln Arg Gly Asp Arg Asp Gly Glu Phe
            180                 185                 190

Tyr Phe Gly Met Met Phe Ile Arg Gly Trp Gly Thr Lys Arg Asp Val
        195                 200                 205

Glu Glu Ala Ala Gly Trp Ile Arg Lys Ala Ala Glu Lys Gly Gln Pro
    210                 215                 220
```

```
Glu Ala Met Arg Val Met Ser Thr Leu Tyr Glu Gly Gly Tyr Gly Val
225                 230                 235                 240

Ala Gln Ser Glu Lys Asp Ala Leu Val Trp Leu Glu Lys Ser Val Asp
            245                 250                 255

Ala Gly Asp Arg Glu Ala Met Arg Arg Leu Ala Ala Val Tyr Glu Asn
        260                 265                 270

Gly Thr Phe Gly Val Thr Pro Asp Lys Glu Lys Ala Arg Leu Leu Lys
        275                 280                 285

Lys Lys Ala Ala Glu Val Lys Lys Ala Val Phe Pro Asp Tyr Ala Val
        290                 295                 300

Met
305

<210> SEQ ID NO 17
<211> LENGTH: 819
<212> TYPE: DNA
<213> ORGANISM: Oxalobacter formigenes

<400> SEQUENCE: 17
atgatgaaaa ccatcctcaa agccctcttc ttcgcattca ttctgattgg ttccactctg      60
gcgttcgccg acaatgttga agaaggcaac catctctata tgctggaaaa atatcaggaa     120
gccctgacct ttttcatgaa accggatgcg gtcaataacc cagccaccat gaaccggatc     180
gggtatatgt acgacgaagg tcagggagtc aaaaaagatc caaagaagc cttcaagtgg      240 tacaaaaaag cagctgatgc caatttacca gttgcccagt ttaatctggg gcttatgtat     300
caacatggca ccggcgtctc aaaagatatc aatgaatcca ttaaatggtt tcgtaaagca     360
gcagaacaaa atgatcccga cgctgaaatg aaaatgggct atttgaccgc aacaggaaca     420
ggggtcaaaa aagattatca agaagctata caatggtatc aacgcgctgc tgaacatggc     480
gatagtgcag cttatgcaca aattggactt ttctatactc tgggcaatgg tgtcaaaaaa     540
gacgtcaacc gtgctgtcca gtattacatt atgggcgctc aaaagggtga tgccagagca     600
caggcctttt tgggaaaagc atatgccttg gcagaggta tccaaccgga tagtgaaaaa      660
gccctctact ggtacaaaac agccgccaga acggcaacg tcaacgccat gaaagaactg      720
ggttccatct atgcaaaagg ccgtctcggt gtcaagccag accagcagga agcacaacga     780
tggaacgaca tggccagaaa agctgaacag aaaaattaa                             819

<210> SEQ ID NO 18
<211> LENGTH: 272
<212> TYPE: PRT
<213> ORGANISM: Oxalobacter formigenes

<400> SEQUENCE: 18

Met Met Lys Thr Ile Leu Lys Ala Leu Phe Phe Ala Phe Ile Leu Ile
1               5                   10                  15

Gly Ser Thr Leu Ala Phe Ala Asp Asn Val Glu Glu Gly Asn His Leu
            20                  25                  30

Tyr Asn Ala Gly Lys Tyr Gln Glu Ala Leu Thr Phe Phe Met Lys Pro
        35                  40                  45

Asp Ala Val Asn Asn Pro Ala Thr Met Asn Arg Ile Gly Tyr Met Tyr
    50                  55                  60

Asp Glu Gly Gln Gly Val Lys Lys Asp Pro Lys Glu Ala Phe Lys Trp
65                  70                  75                  80

Tyr Lys Lys Ala Ala Asp Ala Asn Leu Pro Val Ala Gln Phe Asn Leu
```

```
                85                  90                  95
Gly Leu Met Tyr Gln His Gly Thr Gly Val Ser Lys Asp Ile Asn Glu
                100                 105                 110

Ser Ile Lys Trp Phe Arg Lys Ala Ala Glu Gln Asn Asp Pro Asp Ala
            115                 120                 125

Glu Met Lys Met Gly Tyr Leu Thr Ala Thr Gly Thr Gly Val Lys Lys
        130                 135                 140

Asp Tyr Gln Glu Ala Ile Gln Trp Tyr Gln Arg Ala Ala Glu His Gly
145                 150                 155                 160

Asp Ser Ala Ala Tyr Ala Gln Ile Gly Leu Phe Tyr Thr Leu Gly Asn
                165                 170                 175

Gly Val Lys Lys Asp Val Asn Arg Ala Val Gln Tyr Tyr Ile Met Gly
            180                 185                 190

Ala Gln Lys Gly Asp Ala Arg Ala Gln Ala Phe Leu Gly Lys Ala Tyr
        195                 200                 205

Ala Leu Gly Arg Gly Ile Gln Pro Asp Ser Glu Lys Ala Leu Tyr Trp
210                 215                 220

Tyr Lys Thr Ala Ala Arg Asn Gly Asn Val Asn Ala Met Lys Glu Leu
225                 230                 235                 240

Gly Ser Ile Tyr Ala Lys Gly Arg Leu Gly Val Lys Pro Asp Gln Gln
                245                 250                 255

Glu Ala Gln Arg Trp Asn Asp Met Ala Arg Lys Ala Glu Gln Lys Asn
            260                 265                 270

<210> SEQ ID NO 19
<211> LENGTH: 816
<212> TYPE: DNA
<213> ORGANISM: Oxalobacter formigenes

<400> SEQUENCE: 19
atgaaaattt cttacaagct atttctttct ttcattttaa tgctgtgttc ttccgctgtt      60
tttgctgaca atgctcttac agggatcgag ttatacaaag caaaaaaata tgaacaggcc     120
atgacccacc tcatgacgcc tgatgcccag aaaaacccctg cagcacaaaa tcttattgga     180
tatctctatg ataagggctt aggtgtagaa aaaaacgctg aaatagccaa tcaatggtat     240
cttaaagcag ctgaacaggg atttgccaaa gctcaattca accttggact ctcttatgaa     300 agggtactg gcatttcaaa aaatatggtt gaagctgtca atggtatcg caaagcagct     360 gaacaaaatc acgccaaagc tgaaatgaaa atggggtatc tcacagtaga aggtatcggt     420
actcaaaaga attacaaaga agccttgcaa tggtatcggc gcgcagcaga acatggtgat     480
aatagggctt atgcagacat tggcctcttc tatgatcagg aaacggtgt caaaaaagac     540 cccaaccggg ctgtccagta ttacatcatg ggtgcagaaa agggcgatgg cgaagcacag     600 cttttttctcg cggattgcta cgcgaaagca agcgggattc cttatgatgc cgatcgcgcc     660
ttgtattggt acaaggaatc cgccaaaaac ggaaatatca ctgcgatgaa ggtgttgtcc     720
ggcatttaca acttggcca ttgggtata gagaagaatc cggaaaaatc ccgacactgg     780
cttgagatgg ccaaacaaaa agaagctcag ccatga                              816

<210> SEQ ID NO 20
<211> LENGTH: 271
<212> TYPE: PRT
<213> ORGANISM: Oxalobacter formigenes

<400> SEQUENCE: 20
```

Met Lys Ile Ser Tyr Lys Leu Phe Leu Ser Phe Ile Leu Met Leu Cys
1               5                   10                  15

Ser Ser Ala Val Phe Ala Asp Asn Ala Leu Thr Gly Ile Glu Leu Tyr
            20                  25                  30

Lys Ala Lys Tyr Glu Gln Ala Met Thr His Leu Met Thr Pro Asp
        35                  40                  45

Ala Gln Lys Asn Pro Ala Ala Gln Asn Leu Ile Gly Tyr Leu Tyr Asp
    50                  55                  60

Lys Gly Leu Gly Val Glu Lys Asn Ala Glu Ile Ala Asn Gln Trp Tyr
65                  70                  75                  80

Leu Lys Ala Ala Glu Gln Gly Phe Ala Lys Ala Gln Phe Asn Leu Gly
                85                  90                  95

Leu Ser Tyr Glu Lys Gly Thr Gly Ile Ser Lys Asn Met Val Glu Ala
            100                 105                 110

Val Lys Trp Tyr Arg Lys Ala Ala Glu Gln Asn His Ala Lys Ala Glu
        115                 120                 125

Met Lys Met Gly Tyr Leu Thr Val Glu Gly Ile Gly Thr Gln Lys Asn
    130                 135                 140

Tyr Lys Glu Ala Leu Gln Trp Tyr Arg Arg Ala Ala Glu His Gly Asp
145                 150                 155                 160

Asn Arg Ala Tyr Ala Asp Ile Gly Leu Phe Tyr Asp Gln Gly Asn Gly
                165                 170                 175

Val Lys Lys Asp Pro Asn Arg Ala Val Gln Tyr Tyr Ile Met Gly Ala
            180                 185                 190

Glu Lys Gly Asp Gly Glu Ala Gln Leu Phe Leu Ala Asp Cys Tyr Ala
        195                 200                 205

Lys Ala Ser Gly Ile Pro Tyr Asp Ala Asp Arg Ala Leu Tyr Trp Tyr
    210                 215                 220

Lys Glu Ser Ala Lys Asn Gly Asn Ile Thr Ala Met Lys Val Leu Ser
225                 230                 235                 240

Gly Ile Tyr Lys Leu Gly Gln Leu Gly Ile Glu Lys Asn Pro Glu Lys
                245                 250                 255

Ser Arg His Trp Leu Glu Met Ala Lys Gln Lys Glu Ala Gln Pro
            260                 265                 270

<210> SEQ ID NO 21
<211> LENGTH: 1614
<212> TYPE: DNA
<213> ORGANISM: Oxalobacter formigenes

<400> SEQUENCE: 21
atgtctgaaa caatgttggc tgttctggga tttcctgatc tggatgagct tttgccgatg      60
gcacggctgt ttctggtgtc ttctttgctg gccgggtgtt gtgtgggtc gatgagcttg      120 tttaggggcg gtttctttc gggcagaggt gcccagggga acgtcgtcat gccgagggat      180
aaaatggatt ggaatttggg tcgtgttcgt caggggacgc tggctgtggt cggttgcctg      240
tttctggcga atgccgcgtg ggcgaacgat tattccgacg gcatgcagtt ctatcaggac      300
aaggattacg agaaagcttt ttcttctttc cagaaggcgg ccgacaaggg caatgcggcg      360
gcgcaatccg cactggctgc cctgtactat aacggggaag ggtggagga agatgaggcc      420 gctgctgcgt gtggtattc gcgcgctgcc gaacatggcc gaacggatgc gcagtttgcg      480
cttggcgaga tgttcgaagc cggcgaaggg gtcaaacgcg attataaaaa agcggctttc      540
tggtataaaa aggcggcgga caagggccat ttgatggctg ccacgaagct gggcatcctc      600

-continued

```
tatatggaag gtcgcggagt caagcaagat gacgcgaaag cggctgcatt gctttctcat    660
gccgccaaac ggggcattgc gttggcgcag tcgaatctcg gtgttttgta tgcgagcggg    720
cgcggggttg aatccagtcc gaaacgggcg ctggagtggt acaagaaggc ggctgttcag    780
ggaaattcac aagcccagtt ttcgctcggc aatatgtatg aggacggctc tggtgttgaa    840
aagaatctgg cggtagcggc cgcctggtat cagaagtcgg ccgaacaggg gaatgccgag    900
gcccagaata atctgggacg cctttatatg gaaggcggcg agtttgaggg gcgtgaagac    960
gaagcgttta tgtggttctc ccgtgcggcc gatcaggggt atgccgaggc gcaaacgaat   1020
ctgggtgtct tgtattccta tgggcttggt gtggacaagg atttgtccaa ggcgttttac   1080
tggtatcagc aggcggctga aaaggggcag gctgaagggg ctttttttcct ggctgaggcg   1140
tattacaagg gggaaggtgt tcaccggac gacaaacagg cggttttctg gtatcagaaa   1200
gcggcgaagc tgggtgtccc agaaagtcag gacaggcttg ggttgatgct gacgaacggg   1260
gtcggcgtca acaggatta caagcaggca tatagctggt tcaggaaggc ggcccgtcag   1320
gggtatgccg aatcccagaa caatctgggg gtcttgtatg cccgtggact cggggtcgaa   1380
aaggattaca acaggccgt ggcctggtat cgcaaggcgg tgatgcagaa tctgcctcag   1440
gcgcagttca atctgggaac gatgtatttg caggggcatg tgtcaaaca ggatgtcaaa   1500
caggccagac actggtttac gaaggcggca gcgcaggggt tgccggaagc gcagagaagt   1560
ctggacagga tgccgaaaaa cgggcagacc atcaatacgg atctctcgac ctga         1614
```

<210> SEQ ID NO 22
<211> LENGTH: 1074
<212> TYPE: PRT
<213> ORGANISM: Oxalobacter formigenes

<400> SEQUENCE: 22

```
Met Ser Glu Thr Met Leu Ala Val Leu Gly Phe Pro Asp Leu Asp Glu
1               5                   10                  15

Leu Leu Pro Met Ala Arg Leu Phe Leu Val Ser Ser Leu Leu Ala Gly
            20                  25                  30

Cys Cys Val Gly Ser Met Ser Leu Phe Arg Gly Gly Phe Phe Ser Gly
        35                  40                  45

Arg Gly Ala Gln Gly Asn Val Val Met Pro Arg Asp Lys Met Asp Trp
    50                  55                  60

Asn Leu Gly Arg Val Arg Gln Gly Thr Leu Ala Val Val Gly Cys Leu
65                  70                  75                  80

Phe Leu Ala Asn Ala Ala Trp Ala Asn Asp Tyr Ser Asp Gly Met Gln
                85                  90                  95

Phe Tyr Gln Asp Lys Asp Tyr Glu Lys Ala Phe Ser Ser Phe Gln Lys
            100                 105                 110

Ala Ala Asp Lys Gly Asn Ala Ala Ala Gln Ser Ala Leu Ala Ala Leu
        115                 120                 125

Tyr Tyr Asn Gly Glu Gly Val Glu Glu Asp Ala Ala Ala Ala Leu
    130                 135                 140

Trp Tyr Ser Arg Ala Ala Glu His Gly Arg Thr Asp Ala Gln Phe Ala
145                 150                 155                 160

Leu Gly Glu Met Phe Glu Ala Gly Glu Gly Val Lys Arg Asp Tyr Lys
                165                 170                 175

Lys Ala Ala Phe Trp Tyr Lys Lys Ala Ala Asp Lys Gly His Leu Met
            180                 185                 190

Ala Ala Thr Lys Leu Gly Ile Leu Tyr Met Glu Gly Arg Gly Val Lys
```

```
            195                 200                 205
Gln Asp Asp Ala Lys Ala Ala Leu Leu Ser His Ala Ala Lys Arg
210                 215                 220

Gly Ile Ala Leu Ala Gln Ser Asn Leu Gly Val Leu Tyr Ala Ser Gly
225                 230                 235                 240

Arg Gly Val Glu Ser Ser Pro Lys Arg Ala Leu Glu Trp Tyr Lys Lys
                245                 250                 255

Ala Ala Val Gln Gly Asn Ser Gln Ala Gln Phe Ser Leu Gly Asn Met
                260                 265                 270

Tyr Glu Asp Gly Ser Gly Val Glu Lys Asn Leu Ala Val Ala Ala Ala
                275                 280                 285

Trp Tyr Gln Lys Ser Ala Glu Gln Gly Asn Ala Glu Ala Gln Asn Asn
290                 295                 300

Leu Gly Arg Leu Tyr Met Glu Gly Gly Glu Phe Glu Gly Arg Glu Asp
305                 310                 315                 320

Glu Ala Phe Met Trp Phe Ser Arg Ala Ala Asp Gln Gly Tyr Ala Glu
                325                 330                 335

Ala Gln Thr Asn Leu Gly Val Leu Tyr Ser Tyr Gly Leu Gly Val Asp
                340                 345                 350

Lys Asp Leu Ser Lys Ala Phe Tyr Trp Tyr Gln Gln Ala Ala Glu Lys
                355                 360                 365

Gly Gln Ala Glu Gly Ala Phe Phe Leu Ala Glu Ala Tyr Tyr Lys Gly
370                 375                 380

Glu Gly Val His Arg Asp Asp Lys Gln Ala Val Phe Trp Tyr Gln Lys
385                 390                 395                 400

Ala Ala Lys Leu Gly Val Pro Glu Ser Gln Asp Arg Leu Gly Leu Met
                405                 410                 415

Leu Thr Asn Gly Val Gly Val Lys Gln Asp Tyr Lys Gln Ala Tyr Ser
                420                 425                 430

Trp Phe Arg Lys Ala Ala Arg Gln Gly Tyr Ala Glu Ser Gln Asn Asn
                435                 440                 445

Leu Gly Val Leu Tyr Ala Arg Gly Leu Gly Val Glu Lys Asp Tyr Lys
                450                 455                 460

Gln Ala Val Ala Trp Tyr Arg Lys Ala Val Met Gln Asn Leu Pro Gln
465                 470                 475                 480

Ala Gln Phe Asn Leu Gly Thr Met Tyr Leu Gln Gly His Gly Val Lys
                485                 490                 495

Gln Asp Val Lys Gln Ala Arg His Trp Phe Thr Lys Ala Ala Ala Gln
                500                 505                 510

Gly Leu Pro Glu Ala Gln Arg Ser Leu Asp Arg Met Pro Lys Asn Gly
                515                 520                 525

Gln Thr Ile Asn Thr Asp Leu Ser Thr Met Ser Glu Thr Met Leu Ala
                530                 535                 540

Val Leu Gly Phe Pro Asp Leu Asp Glu Leu Leu Pro Met Ala Arg Leu
545                 550                 555                 560

Phe Leu Val Ser Ser Leu Leu Ala Gly Cys Cys Val Gly Ser Met Ser
                565                 570                 575

Leu Phe Arg Gly Gly Phe Phe Ser Gly Arg Gly Ala Gln Gly Asn Val
                580                 585                 590

Val Met Pro Arg Asp Lys Met Asp Trp Asn Leu Gly Arg Val Arg Gln
                595                 600                 605

Gly Thr Leu Ala Val Val Gly Cys Leu Phe Leu Ala Asn Ala Ala Trp
610                 615                 620
```

```
Ala Asn Asp Tyr Ser Asp Gly Met Gln Phe Tyr Gln Asp Lys Asp Tyr
625                 630                 635                 640

Glu Lys Ala Phe Ser Ser Phe Gln Lys Ala Ala Asp Lys Gly Asn Ala
            645                 650                 655

Ala Ala Gln Ser Ala Leu Ala Ala Leu Tyr Tyr Asn Gly Glu Gly Val
                660                 665                 670

Glu Glu Asp Glu Ala Ala Ala Leu Trp Tyr Ser Arg Ala Ala Glu
            675                 680                 685

His Gly Arg Thr Asp Ala Gln Phe Ala Leu Gly Glu Met Phe Glu Ala
            690                 695                 700

Gly Glu Gly Val Lys Arg Asp Tyr Lys Lys Ala Ala Phe Trp Tyr Lys
705                 710                 715                 720

Lys Ala Ala Asp Lys Gly His Leu Met Ala Ala Thr Lys Leu Gly Ile
                725                 730                 735

Leu Tyr Met Glu Gly Arg Gly Val Lys Gln Asp Asp Ala Lys Ala Ala
                740                 745                 750

Ala Leu Leu Ser His Ala Ala Lys Arg Gly Ile Ala Leu Ala Gln Ser
            755                 760                 765

Asn Leu Gly Val Leu Tyr Ala Ser Gly Arg Gly Val Glu Ser Ser Pro
770                 775                 780

Lys Arg Ala Leu Glu Trp Tyr Lys Lys Ala Ala Val Gln Gly Asn Ser
785                 790                 795                 800

Gln Ala Gln Phe Ser Leu Gly Asn Met Tyr Glu Asp Gly Ser Gly Val
                805                 810                 815

Glu Lys Asn Leu Ala Val Ala Ala Ala Trp Tyr Gln Lys Ser Ala Glu
            820                 825                 830

Gln Gly Asn Ala Glu Ala Gln Asn Asn Leu Gly Arg Leu Tyr Met Glu
            835                 840                 845

Gly Gly Glu Phe Glu Gly Arg Glu Asp Glu Ala Phe Met Trp Phe Ser
850                 855                 860

Arg Ala Ala Asp Gln Gly Tyr Ala Glu Ala Gln Thr Asn Leu Gly Val
865                 870                 875                 880

Leu Tyr Ser Tyr Gly Leu Gly Val Asp Lys Asp Leu Ser Lys Ala Phe
                885                 890                 895

Tyr Trp Tyr Gln Gln Ala Ala Glu Lys Gly Gln Ala Glu Gly Ala Phe
                900                 905                 910

Phe Leu Ala Glu Ala Tyr Tyr Lys Gly Glu Gly Val His Arg Asp Asp
            915                 920                 925

Lys Gln Ala Val Phe Trp Tyr Gln Lys Ala Ala Lys Leu Gly Val Pro
            930                 935                 940

Glu Ser Gln Asp Arg Leu Gly Leu Met Leu Thr Asn Gly Val Gly Val
945                 950                 955                 960

Lys Gln Asp Tyr Lys Gln Ala Tyr Ser Trp Phe Arg Lys Ala Ala Arg
            965                 970                 975

Gln Gly Tyr Ala Glu Ser Gln Asn Asn Leu Gly Val Leu Tyr Ala Arg
            980                 985                 990

Gly Leu Gly Val Glu Lys Asp Tyr Lys Gln Ala Val Ala Trp Tyr Arg
            995                 1000                1005

Lys Ala Val Met Gln Asn Leu Pro Gln Ala Gln Phe Asn Leu Gly
            1010                1015                1020

Thr Met Tyr Leu Gln Gly His Gly Val Leu Gln Asp Val Lys Gln
            1025                1030                1035
```

Ala Arg His Trp Phe Thr Lys Ala Ala Ala Gln Gly Leu Pro Glu
1040                 1045                1050

Ala Gln Arg Ser Leu Asp Arg Met Pro Lys Asn Gly Gln Thr Ile
    1055                1060                1065

Asn Thr Asp Leu Ser Thr
    1070

<210> SEQ ID NO 23
<211> LENGTH: 588
<212> TYPE: DNA
<213> ORGANISM: Oxalobacter formigenes

<400> SEQUENCE: 23

```
atggttcata caggtttttc cgggcagtcc cgtccgtttt ccggatggat ggggactttt      60
ctgtttctgg tgttttgcca gctggcattg gctgccggtg cgatggcggc ggacccggaa     120
aagaaagcgg tggcttcaaa cgggcagctt tcgaaaaatg tggcatccgg ggatgaggat     180
gtgttgcgcg atctgatgga tttgaagagc aatgcggatt cgggtgatgt gtccgcccag     240
tttgagttga ccgccgttac ttgaacggg gatggccttg agcagaacga tgatgaggca     300
atccgctggc tccgtatggc ggcggaaggt ggtttgccga gggcgcaggc gggtctgggc     360
tggatgtatg cggcgggcag gggggtgaat aaggatgaga cgctgtcttt ttcctggtat     420
gaacgggcgg cggttgccgg ttttcctgtg cgcagtata tgctgggccg ttattatgaa      480
aagggtatcg gcgtcgccaa agaccgtgtg ctggctaaag agtggtatga aaaggcggca     540
gcgcagggta atgagaaagc gaagaagcgg ttgcaggact ggaaatga                  588
```

<210> SEQ ID NO 24
<211> LENGTH: 195
<212> TYPE: PRT
<213> ORGANISM: Oxalobacter formigenes

<400> SEQUENCE: 24

Met Val His Thr Gly Phe Ser Gly Gln Ser Arg Pro Phe Ser Gly Trp
1               5                   10                  15

Met Gly Thr Phe Leu Phe Leu Val Phe Cys Gln Leu Ala Leu Ala Ala
            20                  25                  30

Gly Ala Met Ala Ala Asp Pro Glu Lys Lys Ala Val Ala Ser Asn Gly
        35                  40                  45

Gln Leu Ser Lys Asn Val Ala Ser Gly Asp Glu Asp Val Leu Arg Asp
    50                  55                  60

Leu Met Asp Leu Lys Ser Asn Ala Asp Ser Gly Asp Val Ser Ala Gln
65                  70                  75                  80

Phe Glu Leu Ser Arg Arg Tyr Leu Asn Gly Asp Gly Leu Glu Gln Asn
                85                  90                  95

Asp Asp Glu Ala Ile Arg Trp Leu Arg Met Ala Ala Glu Gly Gly Leu
            100                 105                 110

Pro Arg Ala Gln Ala Gly Leu Gly Trp Met Tyr Ala Ala Gly Arg Gly
        115                 120                 125

Val Asn Lys Asp Glu Thr Leu Ser Phe Ser Trp Tyr Glu Arg Ala Ala
    130                 135                 140

Val Ala Gly Phe Pro Val Ala Gln Tyr Met Leu Gly Arg Tyr Tyr Glu
145                 150                 155                 160

Lys Gly Ile Gly Val Ala Lys Asp Arg Val Leu Ala Lys Glu Trp Tyr
                165                 170                 175

Glu Lys Ala Ala Ala Gln Gly Asn Glu Lys Ala Lys Lys Arg Leu Gln

Asp Trp Lys
    195

<210> SEQ ID NO 25
<211> LENGTH: 1200
<212> TYPE: DNA
<213> ORGANISM: Oxalobacter formigenes

<400> SEQUENCE: 25

| | | | | | |
|---|---|---|---|---|---|
| atgcgtagaa | aactgttctt | cttcatttgt | ttattttgtt | ctattacagc | ttcagtctct | 60 |
| tttgctgaaa | cgaaaatcaa | tgaatcgttt | ccggaaattg | aacggtcggg | ggaagaggca | 120 |
| aagagagaaa | cggctatcaa | gctctataat | ctgggcgtgg | aatatgcaaa | aggcagtcgt | 180 |
| gtcgaaaaag | atcgtaaaaa | agccaattcc | tatttcagac | aagctgctga | aataggactg | 240 |
| cctgaagcgc | agtacaatct | gggacgagcg | tatttcgatg | gcgatggtct | ggaggtagac | 300 |
| aggaaagcag | ctattgaatg | gtacaaaaag | gcagcagaac | agggatttgc | acaggctcaa | 360 |
| tacaacttgg | gcgtaatcta | ccaaaatggt | ttgggcatca | acaggatttt | gattcggct | 420 |
| gtccagtggt | atgagagagc | ggcaaatcag | ggatttgtat | tagcccaata | caatcttgga | 480 |
| atgttatata | taactggagc | aggcgttggc | aagaatccga | acgagggat | tttgtggttg | 540 |
| cgcaaggctg | ctgaaggggg | ttacggtcag | gcgcagcata | tcttggaac | cgtttattac | 600 |
| gagggtattg | gcgtcagaaa | aaattatccg | gaagcggtgc | aatggttcgc | caaagctgct | 660 |
| aaacaagagc | ttggcatggc | gcaatacaat | ctggggatgg | cttactatca | tggagagggc | 720 |
| gtcaaaaaaa | atcctcagaa | agcggtttca | tggttgaaaa | aagcagcaaa | acaaaatctt | 780 |
| cttatagctc | aggctagtct | tggctatata | tatgttacgg | acaggaattt | caaaaataat | 840 |
| ctggcagaag | gaattttctg | gacaaaaaaa | gcctccgcat | atggtaatgc | aagggctcag | 900 |
| gcgacacttg | gtattgcata | tcttattgga | aagggtgtag | aaaaaaatat | tccagaaggc | 960 |
| gtttcgtgga | taaaaaaagc | agcgagacag | ggtaattatc | cggctcaaag | catgcttgct | 1020 |
| tcctgttatg | aaaatgggat | tggcgtaaag | caaaacaagg | tattggctta | tgcactttat | 1080 |
| ttacactcat | ctccttatac | ggaagttgct | atggaagaac | ggcaaaatct | tgaaaaaaag | 1140 |
| ctaagcaaag | atgaaattgt | aaaagcccga | tccatcaaca | tcgaaaaact | tttcgaatga | 1200 |

<210> SEQ ID NO 26
<211> LENGTH: 399
<212> TYPE: PRT
<213> ORGANISM: Oxalobacter formigenes

<400> SEQUENCE: 26

Met Arg Arg Lys Leu Phe Phe Phe Ile Cys Leu Phe Cys Ser Ile Thr
1               5                   10                  15

Ala Ser Val Ser Phe Ala Glu Thr Lys Ile Asn Glu Ser Phe Pro Glu
            20                  25                  30

Ile Glu Arg Ser Gly Glu Glu Ala Lys Arg Glu Thr Ala Ile Lys Leu
        35                  40                  45

Tyr Asn Leu Gly Val Glu Tyr Ala Lys Gly Ser Arg Val Glu Lys Asp
    50                  55                  60

Arg Lys Lys Ala Asn Ser Tyr Phe Arg Gln Ala Glu Ile Gly Leu
65                  70                  75                  80

Pro Glu Ala Gln Tyr Asn Leu Gly Arg Ala Tyr Phe Asp Gly Asp Gly
                85                  90                  95

```
Leu Glu Val Asp Arg Lys Ala Ala Ile Glu Trp Tyr Lys Ala Ala
            100                 105                 110
Glu Gln Gly Phe Ala Gln Ala Gln Tyr Asn Leu Gly Val Ile Tyr Gln
        115                 120                 125
Asn Gly Leu Gly Ile Lys Gln Asp Phe Asp Ser Ala Val Gln Trp Tyr
    130                 135                 140
Glu Arg Ala Ala Asn Gln Gly Phe Val Leu Ala Gln Tyr Asn Leu Gly
145                 150                 155                 160
Met Leu Tyr Ile Thr Gly Ala Gly Val Gly Lys Asn Pro Lys Arg Gly
                165                 170                 175
Ile Leu Trp Leu Arg Lys Ala Ala Glu Gly Gly Tyr Gly Gln Ala Gln
            180                 185                 190
His Asn Leu Gly Thr Val Tyr Tyr Glu Gly Ile Gly Val Arg Lys Asn
        195                 200                 205
Tyr Pro Glu Ala Val Gln Trp Phe Ala Lys Ala Ala Lys Gln Glu Leu
    210                 215                 220
Gly Met Ala Gln Tyr Asn Leu Gly Met Ala Tyr Tyr His Gly Glu Gly
225                 230                 235                 240
Val Lys Lys Asn Pro Gln Lys Ala Val Ser Trp Leu Lys Lys Ala Ala
                245                 250                 255
Lys Gln Asn Leu Leu Ile Ala Gln Ala Ser Leu Gly Tyr Ile Tyr Val
            260                 265                 270
Thr Asp Arg Asn Phe Lys Asn Asn Leu Ala Glu Gly Ile Phe Trp Thr
        275                 280                 285
Lys Lys Ala Ser Ala Tyr Gly Asn Ala Arg Ala Gln Ala Thr Leu Gly
    290                 295                 300
Ile Ala Tyr Leu Ile Gly Lys Gly Val Glu Lys Asn Ile Pro Glu Gly
305                 310                 315                 320
Val Ser Trp Ile Lys Lys Ala Ala Arg Gln Gly Asn Tyr Pro Ala Gln
                325                 330                 335
Ser Met Leu Ala Ser Cys Tyr Glu Asn Gly Ile Gly Val Lys Gln Asn
            340                 345                 350
Lys Val Leu Ala Tyr Ala Leu Tyr Leu His Ser Ser Pro Tyr Thr Glu
        355                 360                 365
Val Ala Met Glu Glu Arg Gln Asn Leu Glu Lys Lys Leu Ser Lys Asp
    370                 375                 380
Glu Ile Val Lys Ala Arg Ser Ile Asn Ile Glu Lys Leu Phe Glu
385                 390                 395
```

<210> SEQ ID NO 27
<211> LENGTH: 909
<212> TYPE: DNA
<213> ORGANISM: Oxalobacter formigenes

<400> SEQUENCE: 27

```
atgaaaaaaa atatttcact catctttttt atatttattt ctttattttc tttgactgga    60
tgtcaaaatg aagataataa agagttaaca gatgaaaaaa caggaattga atactataaa   120
aaaggtgact acgaaaaatc attatccttt ctgaagaaag ccgctgattc cggagtatc    180
aaagcttccc ggtatttggg aaaaatgtat cagtatggca aagtgtcga taaagattat   240
ccgctttctt tcaagtggta tttaaacgca gccgaaaaag gagacaaaga atcatccggt   300
atggttggcg ccagttacta tttgggacaa ggcgtaaaac aagactacaa ggaatcgttt   360
agatggttgt taaaggcatc tgaaaaaatt gatgaaaaaa aaccaactga acgggacgga   420
```

```
aaactcatgc ttcttttggc taatttatat tttacgggaa aaggtacact tcaggatttc    480
agtgagtcag caaatgggc gagaagagct gccgaattgg gaaattccga gtcacaagcc    540
atgcttgcat tcttcctcta ttccgggcaa ggcattttac agaacagaac ggaagcgaaa    600
atctgggcag aaaagtctgc cgggcagggg gatagccttg gacaagtcat aatgggaatg    660
ctttatcagt atggcggcgg aacagatgaa ccggatatga gaaaagcaat cgactggtac    720
gaaaaatcag ctgaaaaggg aaatccgatt gcacaatatc aactggcaac cctttacgaa    780
aatgggaatg gcttgccgaa agatctggaa aaagcaaaat actattatga gcaatcggct    840
aaaagccaat cggaaatacc agtgaaagct ttggcggaat tcaaggccaa acagaaaaga    900
caaaattaa                                                            909
```

<210> SEQ ID NO 28
<211> LENGTH: 302
<212> TYPE: PRT
<213> ORGANISM: Oxalobacter formigenes

<400> SEQUENCE: 28

```
Met Lys Lys Asn Ile Ser Leu Ile Phe Phe Ile Phe Ile Ser Leu Phe
1               5                   10                  15

Ser Leu Thr Gly Cys Gln Asn Glu Asp Asn Lys Glu Leu Thr Asp Glu
            20                  25                  30

Lys Thr Gly Ile Glu Tyr Tyr Lys Lys Gly Asp Tyr Glu Lys Ser Leu
        35                  40                  45

Ser Phe Leu Lys Lys Ala Ala Asp Ser Gly Ser Ile Lys Ala Ser Arg
    50                  55                  60

Tyr Leu Gly Lys Met Tyr Gln Tyr Gly Lys Gly Val Asp Lys Asp Tyr
65                  70                  75                  80

Pro Leu Ser Phe Lys Trp Tyr Leu Asn Ala Ala Glu Lys Gly Asp Lys
                85                  90                  95

Glu Ser Ser Gly Met Val Gly Ala Ser Tyr Tyr Leu Gly Gln Gly Val
            100                 105                 110

Lys Gln Asp Tyr Lys Glu Ser Phe Arg Trp Leu Leu Lys Ala Ser Glu
        115                 120                 125

Lys Ile Asp Glu Lys Lys Pro Thr Glu Arg Asp Gly Lys Leu Met Leu
    130                 135                 140

Leu Leu Ala Asn Leu Tyr Phe Thr Gly Lys Gly Thr Leu Gln Asp Phe
145                 150                 155                 160

Ser Glu Ser Ala Lys Trp Ala Arg Arg Ala Glu Leu Gly Asn Ser
                165                 170                 175

Glu Ser Gln Ala Met Leu Ala Phe Phe Leu Tyr Ser Gly Gln Gly Ile
            180                 185                 190

Leu Gln Asn Arg Thr Glu Ala Lys Ile Trp Ala Glu Lys Ser Ala Gly
        195                 200                 205

Gln Gly Asp Ser Leu Gly Gln Val Ile Met Gly Met Leu Tyr Gln Tyr
    210                 215                 220

Gly Gly Gly Thr Asp Glu Pro Asp Met Lys Lys Ala Ile Asp Trp Tyr
225                 230                 235                 240

Glu Lys Ser Ala Glu Lys Gly Asn Pro Ile Ala Gln Tyr Gln Leu Ala
                245                 250                 255

Thr Leu Tyr Glu Asn Gly Asn Gly Leu Pro Lys Asp Leu Glu Lys Ala
            260                 265                 270

Lys Tyr Tyr Tyr Glu Gln Ser Ala Lys Ser Gln Ser Glu Ile Pro Val
        275                 280                 285
```

Lys Ala Leu Ala Glu Phe Lys Ala Lys Gln Lys Arg Gln Asn
        290                 295                 300

<210> SEQ ID NO 29
<211> LENGTH: 885
<212> TYPE: DNA
<213> ORGANISM: Oxalobacter formigenes

<400> SEQUENCE: 29
atgatgaata aaatatttca ggttttttat atcgtaattc tttctttttt tattagttcc     60
tgccacgaat cagacaacag aatatcagaa aataatggtg tcaatctcta caaggcaaag    120
caatatgaaa tggcattgcc tttacttgaa aaggctgcca atgcaggaga tcctcaggcg    180
ccattctatc tcggcataat gttcgatgaa ggatcaggag taatcaaaga tcagaaaaaa    240
tcatttgaat ggtttgaaaa agcggcaaaa aatggtaaca ctgacgcgtt ttttgttatt    300
ggcagcaggt atttatatgg ttctggcgtt gaaaagatt ataaagaagc cctgaaatgg    360
tataaaagga gtgttgaaga gggcaaaaaa gacgacaaga caatctattt catgatcgga    420
tcgatgtact acaatggttt gggtaccttg aagatacca gcgaggcagc caaatggtat    480
gaaaaagcgg cagaaaaagg agatgctttt tcacaggcaa tgctcgccat gcaatattac    540
agtggtcagg gtattttgac gaatatggaa aaagccagat actgggccga aaaatccgcg    600
gaacaggatt acgatgccgg acaaatgatg atggggattc tgagccagta tggaacacct    660
gaaccagaca tgaaagccgc aattgactgg tatgaaaaag ccgccagaca gggaaacccg    720
attgcacagt ttctattggc gagaagttat gaaaatggaa acggcgtgcc aaaagatctg    780
gaaaaagccc atgcttatta taacaggct gccggtggca tgaagtcgga tgacctggcc    840
agggagttta tggaatttga agcaagacag aaaagacaga ataa                     885

<210> SEQ ID NO 30
<211> LENGTH: 294
<212> TYPE: PRT
<213> ORGANISM: Oxalobacter formigenes

<400> SEQUENCE: 30

Met Met Asn Lys Ile Phe Gln Val Phe Tyr Ile Val Ile Leu Ser Phe
1               5                   10                  15

Phe Ile Ser Ser Cys His Glu Ser Asp Asn Arg Ile Ser Glu Asn Asn
            20                  25                  30

Gly Val Asn Leu Tyr Lys Ala Lys Gln Tyr Glu Met Ala Leu Pro Leu
        35                  40                  45

Leu Glu Lys Ala Ala Asn Ala Gly Asp Pro Gln Ala Pro Phe Tyr Leu
    50                  55                  60

Gly Ile Met Phe Asp Glu Gly Ser Gly Val Ile Lys Asp Gln Lys Lys
65                  70                  75                  80

Ser Phe Glu Trp Phe Glu Lys Ala Ala Lys Asn Gly Asn Thr Asp Ala
                85                  90                  95

Phe Phe Val Ile Gly Ser Arg Tyr Leu Tyr Gly Ser Gly Val Glu Lys
            100                 105                 110

Asp Tyr Lys Glu Ala Leu Lys Trp Tyr Lys Arg Ser Val Glu Glu Gly
        115                 120                 125

Lys Lys Asp Asp Lys Thr Ile Tyr Phe Met Ile Gly Ser Met Tyr Tyr
    130                 135                 140

Asn Gly Leu Gly Thr Leu Lys Asp Thr Ser Glu Ala Ala Lys Trp Tyr
145                 150                 155                 160

Glu Lys Ala Ala Glu Lys Gly Asp Ala Phe Ser Gln Ala Met Leu Ala
            165                 170                 175

Met Gln Tyr Tyr Ser Gly Gln Gly Ile Leu Thr Asn Met Glu Lys Ala
            180                 185                 190

Arg Tyr Trp Ala Glu Lys Ser Ala Glu Gln Asp Tyr Asp Ala Gly Gln
        195                 200                 205

Met Met Met Gly Ile Leu Ser Gln Tyr Gly Thr Pro Glu Pro Asp Met
210                 215                 220

Lys Ala Ala Ile Asp Trp Tyr Glu Lys Ala Arg Gln Gly Asn Pro
225                 230                 235                 240

Ile Ala Gln Phe Leu Leu Ala Arg Ser Tyr Glu Asn Gly Asn Gly Val
            245                 250                 255

Pro Lys Asp Leu Glu Lys Ala His Ala Tyr Tyr Lys Gln Ala Ala Gly
            260                 265                 270

Gly Met Lys Ser Asp Asp Leu Ala Arg Glu Phe Met Glu Phe Glu Ala
            275                 280                 285

Arg Gln Lys Arg Gln Lys
        290

<210> SEQ ID NO 31
<211> LENGTH: 813
<212> TYPE: DNA
<213> ORGANISM: Oxalobacter formigenes

<400> SEQUENCE: 31
atgctgggat atttgtatcg tgaggggtat ggagtcaagc aggattatca aaaggcgttt      60
tttctctatc ttgaaggagc aaaactgggc gacgcaaaaa gccagttcgg tttgggtttt     120
atgtatgagg ggggattatt cgtcaaacag gattatgcca aggcaaaaac atggtatgag     180
tattcatcca atcagggata tctgtctgcg atgaataatc ttggatcgct ttatgacgat     240
gaaaacactg gctttaaaaa cgagaaaatc gcatttgaat ggatattgaa agctgcccaa     300
aaagataacc caactgctca atttaatatc ggttttttt acgaaaaagg cacaggaacc     360
aaaaaagact atgccgaagc ccgaaagtgg tatgaaaaag cagtcatgca gggatatctt     420
ccggccaaag cgaatctggc aaatctctat cttgatggaa aaggtggccc caaagaccag     480
caaaagggcg ttgccctgat aaagaagcg gcgaacgagg aatcgaaagc cgcacaatac     540
acactggcaa acctctacgc cgatggcgaa ggcgttccgc aaagcgatga acaggccgtt     600
tactggttcc acaaggccgc tgaaaacgac agcgcgctgg ccatggacat gctcgccaaa     660
gcctacctga acggaaaata cggactgccg aaaagcccga cgaaatggga ctactggcaa     720
aagagggcag ccgaaacgcg cgcccgtaca cacgaagtcg atccttcaag ctggacaata     780
ttcgactgga tcaaatacaa gttaggcaat tga                                    813

<210> SEQ ID NO 32
<211> LENGTH: 270
<212> TYPE: PRT
<213> ORGANISM: Oxalobacter formigenes

<400> SEQUENCE: 32

Met Leu Gly Tyr Leu Tyr Arg Glu Gly Tyr Gly Val Lys Gln Asp Tyr
1               5                   10                  15

Gln Lys Ala Phe Phe Leu Tyr Leu Glu Gly Ala Lys Leu Gly Asp Ala
            20                  25                  30

Lys Ser Gln Phe Gly Leu Gly Phe Met Tyr Glu Gly Gly Leu Phe Val

```
                35                  40                  45
Lys Gln Asp Tyr Ala Lys Ala Lys Thr Trp Tyr Glu Tyr Ser Ser Asn
 50                  55                  60

Gln Gly Tyr Leu Ser Ala Met Asn Asn Leu Gly Ser Leu Tyr Asp Asp
 65                  70                  75                  80

Glu Asn Thr Gly Phe Lys Asn Glu Lys Ile Ala Phe Glu Trp Ile Leu
                 85                  90                  95

Lys Ala Ala Gln Lys Asp Asn Pro Thr Ala Gln Phe Asn Ile Gly Phe
                100                 105                 110

Phe Tyr Glu Lys Gly Thr Gly Thr Lys Lys Asp Tyr Ala Glu Ala Arg
            115                 120                 125

Lys Trp Tyr Glu Lys Ala Val Met Gln Gly Tyr Leu Pro Ala Lys Ala
130                 135                 140

Asn Leu Ala Asn Leu Tyr Leu Asp Gly Lys Gly Pro Lys Asp Gln
145                 150                 155                 160

Gln Lys Gly Val Ala Leu Ile Lys Glu Ala Asn Glu Glu Ser Lys
                165                 170                 175

Ala Ala Gln Tyr Thr Leu Ala Asn Leu Tyr Ala Asp Gly Glu Gly Val
            180                 185                 190

Pro Gln Ser Asp Glu Gln Ala Val Tyr Trp Phe His Lys Ala Ala Glu
        195                 200                 205

Asn Asp Ser Ala Leu Ala Met Asp Met Leu Ala Lys Ala Tyr Leu Asn
210                 215                 220

Gly Lys Tyr Gly Leu Pro Lys Ser Pro Thr Lys Trp Asp Tyr Trp Gln
225                 230                 235                 240

Lys Arg Ala Ala Glu Thr Arg Ala Arg Thr His Glu Val Asp Pro Ser
                245                 250                 255

Ser Trp Thr Ile Phe Asp Trp Ile Lys Tyr Lys Leu Gly Asn
            260                 265                 270

<210> SEQ ID NO 33
<211> LENGTH: 726
<212> TYPE: DNA
<213> ORGANISM: Oxalobacter formigenes

<400> SEQUENCE: 33
ttgatatttt tcagaaaaaa aagcgacgct ggagaaagtt gcctgagaga tactatgaaa      60
agccgttttt accgcttcaa acatcatttt tcttatatag aaaaatgggt gattttcaat     120
gttgtttttt tgaccatttc tgcttcgtcg tttgcacaaa cgcatccgat aaccggaaca     180
tctgatcccg acagtcaaca tactcaggtt catcaaaaac tcctgtctct cgcagaaaat     240
ggcgatcagg atgcgcagta caatctcgga cgtatatacc tgcaaggaaa aggaacacgt     300
caggattatc aggccgcccg taaatggttc atgcgcgccg ccgaaaaaga ggatgccgga     360
gcccaataca atctgggaaa tatttatcaa aaaggacaag ggattcaaca ggattgcaaa     420
aaagcctttt tctggtacaa aaaggcagct gcaaaattct atgcgccggc tcagtacgct     480
cttggcaagc tttactcaag tggatgtggt gtcaatcaaa attcatataa atcgacagaa     540
tggattctta aggcagccta taatggcatg ccggaagccc aatttcagat aggatatcgg     600
tatctcacag gctatggaat tcaagtcgat aaaaacaagg cctatgaatg gctgttgaag     660
gcggcaaaac aggataaccc agcggcaata aaggttctga aacaaatttt ttccacagaa     720
atatga                                                                726
```

<210> SEQ ID NO 34
<211> LENGTH: 241
<212> TYPE: PRT
<213> ORGANISM: Oxalobacter formigenes

<400> SEQUENCE: 34

```
Met Ile Phe Phe Arg Lys Lys Ser Asp Ala Gly Glu Ser Cys Leu Arg
1               5                   10                  15
Asp Thr Met Lys Ser Arg Phe Tyr Arg Phe Lys His His Phe Ser Tyr
            20                  25                  30
Ile Glu Lys Trp Val Ile Phe Asn Val Val Phe Leu Thr Ile Ser Ala
        35                  40                  45
Ser Ser Phe Ala Gln Thr His Pro Ile Thr Gly Thr Ser Asp Pro Asp
    50                  55                  60
Ser Gln His Thr Gln Val His Gln Lys Leu Leu Ser Leu Ala Glu Asn
65                  70                  75                  80
Gly Asp Gln Asp Ala Gln Tyr Asn Leu Gly Arg Ile Tyr Leu Gln Gly
                85                  90                  95
Lys Gly Thr Arg Gln Asp Tyr Gln Ala Ala Arg Lys Trp Phe Met Arg
            100                 105                 110
Ala Ala Glu Lys Glu Asp Ala Gly Ala Gln Tyr Asn Leu Gly Asn Ile
        115                 120                 125
Tyr Gln Lys Gly Gln Gly Ile Gln Gln Asp Cys Lys Lys Ala Phe Phe
    130                 135                 140
Trp Tyr Lys Lys Ala Ala Lys Phe Tyr Ala Pro Ala Gln Tyr Ala
145                 150                 155                 160
Leu Gly Lys Leu Tyr Ser Ser Gly Cys Gly Val Asn Gln Asn Ser Tyr
                165                 170                 175
Lys Ser Thr Glu Trp Ile Leu Lys Ala Ala Tyr Asn Gly Met Pro Glu
            180                 185                 190
Ala Gln Phe Gln Ile Gly Tyr Arg Tyr Leu Thr Gly Tyr Gly Ile Gln
        195                 200                 205
Val Asp Lys Asn Lys Ala Tyr Glu Trp Leu Leu Lys Ala Ala Lys Gln
    210                 215                 220
Asp Asn Pro Ala Ala Ile Lys Val Leu Lys Thr Asn Phe Ser Thr Glu
225                 230                 235                 240
Ile
```

<210> SEQ ID NO 35
<211> LENGTH: 453
<212> TYPE: DNA
<213> ORGANISM: Oxalobacter formigenes

<400> SEQUENCE: 35

```
atgttttctt ttctgaaaaa agcggttccg gtcagtctcg ttctggtttc tgtcggggtt      60
ttgtctgcct gtactacagg acaggaaatg acggccaagt tgacggcaca ggcgaaaaag     120
ggggatgtgg aagcgatggt cgagctggcg gaggtttatt gcgtggcaa  aaacatcgaa     180
caggacgacc agatttgcgg catgtggatg aaacgggcag ctgaaaaagg ccatgtccgt     240
gcccagtata tgctcggcag aatgtatgaa ctgggtctgg gtatgagagc cgatccggta     300
caggcataca gtggtatag  cttgtctgcc cccattatc  atatgtccca gactggtgca     360
gagactgtat atgccgtcat gacacctgtc cagcagtcag aagccagaaa agtggctgat     420
gaggcgaaga aaaccattcc ttcaaaacaa taa                                  453
```

<210> SEQ ID NO 36
<211> LENGTH: 150
<212> TYPE: PRT
<213> ORGANISM: Oxalobacter formigenes

<400> SEQUENCE: 36

```
Met Phe Ser Phe Leu Lys Lys Ala Val Pro Val Ser Leu Val Leu Val
1               5                   10                  15

Ser Val Gly Val Leu Ser Ala Cys Thr Thr Gly Gln Glu Met Thr Ala
            20                  25                  30

Lys Leu Thr Ala Gln Ala Glu Lys Gly Asp Val Glu Ala Met Val Glu
        35                  40                  45

Leu Ala Glu Val Tyr Cys Gly Gly Lys Asn Ile Glu Gln Asp Asp Gln
    50                  55                  60

Ile Cys Gly Met Trp Met Lys Arg Ala Ala Glu Lys Gly His Val Arg
65                  70                  75                  80

Ala Gln Tyr Met Leu Gly Arg Met Tyr Glu Leu Gly Leu Gly Met Arg
                85                  90                  95

Ala Asp Pro Val Gln Ala Tyr Lys Trp Tyr Ser Leu Ser Ala Pro His
            100                 105                 110

Tyr His Met Ser Gln Thr Gly Ala Glu Thr Val Tyr Ala Val Met Thr
        115                 120                 125

Pro Val Gln Gln Ser Glu Ala Arg Lys Val Ala Asp Glu Ala Lys Lys
    130                 135                 140

Thr Ile Pro Ser Lys Gln
145                 150
```

<210> SEQ ID NO 37
<211> LENGTH: 1536
<212> TYPE: DNA
<213> ORGANISM: Oxalobacter formigenes

<400> SEQUENCE: 37

```
atggctaatc gagaagaatt acaactgttg cgtgaagcac gatccaacca tcacgaagcc    60
cagctccagt tgggcaaact gtatttgttc ggaacaaaaa gcctgccgca agtctgacg    120
accgccctgc actggttaag ccgtgcggcg acacaatcca taaggaagc gtgccttctg    180
attggcgacc atattcctta tgaaattgcc agaaattttc cggatcaggt ggcgatccag    240
tcctggtaca gaacagccct gacagaaggg cattatgagg ctggtctggt attggcccgg    300
ctgattcttt cagatcccaa tcagatcgat gacaaaaagt atgccgaagc gattcgcatt    360
ctcgaaacaa ttgcagatca tgatattgcc gaagcacaat ggttactggc tgaattggcc    420
aaagatccga tgcccggcc atccattatt aacaatgccc ttaaatggac agcgagagcc    480
gccgatgccg gcattgtcga tgcacagatc gccctgattg aacatgcctg gaaaacagg    540
gactaccccg tttttctgca gcatgccttg ccgattgccc gatcgattac tcaggcagtc    600
cagcagggtg atgtcattaa tattgacgaa caatcttccc gtttactgtt cggtgcggg    660
caactgctcc tgaaacagga cggtcatgca tcagaagaga ttcagtccat gtgggaattg    720
ccgccagac agaaaaatgc cgaagccgct ttttcattag cctgtggta cgcgcgcatg    780
aatgaagacg gtatccgcgt cagtattggc gcggccgcga ccagtttcaa aaaagcgatt    840
cgatggctga ctcaggccgg tgaacagggt ctggccaaag catggtacgc actttcactt    900
atttaccaga aggcggaatt ctcacagaga aatatgaatg atgcccaacg ttatctggaa    960
ttggcagcag atcttggaca tgcaacagcc cagtatgaaa gaggcatgca tgcgtggcgg   1020
```

-continued

```
gcacgccggg atgatgaatc aaatgacatt caggctgttt actggctgca gaaagcaaac    1080
ggaaacggaa aagcggacgc ggcagctgtc cttgataaaa ttgctttcaa ggcgaatcct    1140
gcatcatggg cggtaagcgc acgggaatgc ctgactcacg aaattttcag cagccatcca    1200
tttctggccg cccgtatcga actggctgcc gtattcggac tgacacgtcc ggaagcgctc    1260
ttgctcgata tccacaatgc cgacaaaggc cattgccttc tggtcgatat tcgtgaattt    1320
tacagacgca gcaagcgcaa gctcatcctg attcaaactg ccaggaacg ccagattctc     1380 tcccgaatcg gacgtctttt tgaaaaagtg gattgcggcc tgaatggtcc cgagggtaat    1440
tacagacaac gtcaatatcg cctcaaaacg atgctcccgg ccgcttatca ggaaaattca    1500
gatgatgaag aatatcggga acagccgaa gcctag                                1536
```

<210> SEQ ID NO 38
<211> LENGTH: 511
<212> TYPE: PRT
<213> ORGANISM: Oxalobacter formigenes

<400> SEQUENCE: 38

```
Met Ala Asn Arg Glu Glu Leu Gln Leu Leu Arg Glu Ala Arg Ser Asn
1               5                   10                  15

His His Glu Ala Gln Leu Gln Leu Gly Lys Leu Tyr Leu Phe Gly Thr
                20                  25                  30

Lys Ser Leu Pro Gln Ser Leu Thr Thr Ala Leu His Trp Leu Ser Arg
        35                  40                  45

Ala Ala Thr Gln Ser Asn Lys Glu Ala Cys Leu Leu Ile Gly Asp His
    50                  55                  60

Ile Pro Tyr Glu Ile Ala Arg Asn Phe Pro Asp Gln Val Ala Ile Gln
65                  70                  75                  80

Ser Trp Tyr Arg Thr Ala Leu Thr Glu Gly His Tyr Glu Ala Gly Leu
                85                  90                  95

Val Leu Ala Arg Leu Ile Leu Ser Asp Pro Asn Gln Ile Asp Asp Lys
            100                 105                 110

Lys Tyr Ala Glu Ala Ile Arg Ile Leu Glu Thr Ile Ala Asp His Asp
        115                 120                 125

Ile Ala Glu Ala Gln Trp Leu Leu Ala Glu Leu Ala Lys Asp Pro Asn
    130                 135                 140

Ala Arg Pro Ser Ile Ile Asn Asn Ala Leu Lys Trp Thr Ala Arg Ala
145                 150                 155                 160

Ala Asp Ala Gly Ile Val Asp Ala Gln Ile Ala Leu Ile Glu His Ala
                165                 170                 175

Trp Glu Asn Arg Asp Tyr Pro Val Phe Leu Gln His Ala Leu Pro Ile
            180                 185                 190

Ala Arg Ser Ile Thr Gln Ala Val Gln Gln Gly Asp Val Ile Asn Ile
        195                 200                 205

Asp Glu Gln Ser Ser Arg Leu Leu Phe Arg Cys Gly Gln Leu Leu Leu
    210                 215                 220

Lys Gln Asp Gly His Ala Ser Glu Glu Ile Gln Ser Met Trp Glu Leu
225                 230                 235                 240

Ala Ala Arg Gln Lys Asn Ala Glu Ala Phe Ser Leu Gly Leu Trp
                245                 250                 255

Tyr Ala Arg Met Asn Glu Asp Gly Ile Arg Val Ser Ile Gly Ala Ala
            260                 265                 270

Ala Thr Ser Phe Lys Lys Ala Ile Arg Trp Leu Thr Gln Ala Gly Glu
        275                 280                 285
```

```
Gln Gly Leu Ala Lys Ala Trp Tyr Ala Leu Ser Leu Ile Tyr Gln Lys
    290                 295                 300

Ala Glu Phe Ser Gln Arg Asn Met Asn Asp Ala Gln Arg Tyr Leu Glu
305                 310                 315                 320

Leu Ala Ala Asp Leu Gly His Ala Thr Ala Gln Tyr Glu Arg Gly Met
                325                 330                 335

His Ala Trp Arg Ala Arg Arg Asp Asp Glu Ser Asn Asp Ile Gln Ala
            340                 345                 350

Val Tyr Trp Leu Gln Lys Ala Asn Gly Asn Gly Lys Ala Asp Ala Ala
        355                 360                 365

Ala Val Leu Asp Lys Ile Ala Phe Lys Ala Asn Pro Ala Ser Trp Ala
    370                 375                 380

Val Ser Ala Arg Glu Cys Leu Thr His Glu Ile Phe Ser Ser His Pro
385                 390                 395                 400

Phe Leu Ala Ala Arg Ile Glu Leu Ala Ala Val Phe Gly Leu Thr Arg
                405                 410                 415

Pro Glu Ala Leu Leu Leu Asp Ile His Asn Ala Asp Lys Gly His Cys
            420                 425                 430

Leu Leu Val Asp Ile Arg Glu Phe Tyr Arg Arg Ser Lys Arg Lys Leu
        435                 440                 445

Ile Leu Ile Gln Thr Gly Gln Glu Arg Gln Ile Leu Ser Arg Ile Gly
    450                 455                 460

Arg Leu Phe Glu Lys Val Asp Cys Gly Leu Asn Gly Pro Glu Gly Asn
465                 470                 475                 480

Tyr Arg Gln Arg Gln Tyr Arg Leu Lys Thr Met Leu Pro Ala Ala Tyr
                485                 490                 495

Gln Glu Asn Ser Asp Asp Glu Leu Tyr Arg Glu Thr Ala Glu Ala
            500                 505                 510

<210> SEQ ID NO 39
<211> LENGTH: 798
<212> TYPE: DNA
<213> ORGANISM: Oxalobacter formigenes

<400> SEQUENCE: 39
ttggaaaaac ttaatttctt taagaagcaa cctgaactct ctatcaatga attagctttc      60
aaagcaaggc aaggcgatct cgatgcttta aaacgattgc aagaagcagc cgagcaaaat    120
gatgcgaatg cccagaatag acttggggtt atatatgccg atggcaaagg catcccgaga    180
aacgagaact ggctgctgca caggttccaa aaagcagctg aattagaaaa cgctgaagca    240
caggctaacc tagccgccct atatagaaat tcattagttg tcccacgtga taatgcgaag    300
gttatttact gggctcagaa ggctgctgaa catggaaatc ctagaggaca gaatattcta    360
gggtttatgt atatgatcgg agaaggtgta cagcaagatg acgccaaagc agcttcttgg    420
tatcaaaaag ccgctgagca gggattcgca ggagggcaga ggaatttagc gtttatgtat    480
ctcaatggaa agggtgttcc gcaagatgac gctacagcaa cttattggta tcaaaaagcg    540
gcaaatcaag gtgacataca agcgcaaaaa agtttaaaga tgattcaaga aaaagtaaa     600 gaaatgagta actataattt aaatacggta caacaatcac ctccccaggc atcatctcat    660
cagccacttc ccaaagcatc accttcaaat gaaagaaatt tatcaccttt aaaaaatatc    720
tttgacaaac tgaagcagaa ttctgcaaag atgaaatctg ctcctcccgg caacgaagaa    780
caggattacc tgaaatag                                                  798
```

<210> SEQ ID NO 40
<211> LENGTH: 265
<212> TYPE: PRT
<213> ORGANISM: Oxalobacter formigenes

<400> SEQUENCE: 40

```
Met Glu Lys Leu Asn Phe Phe Lys Lys Gln Pro Glu Leu Ser Ile Asn
1               5                   10                  15

Glu Leu Ala Phe Lys Ala Arg Gln Gly Asp Leu Asp Ala Leu Lys Arg
            20                  25                  30

Leu Gln Glu Ala Ala Glu Gln Asn Asp Ala Asn Ala Gln Asn Arg Leu
        35                  40                  45

Gly Val Ile Tyr Ala Asp Gly Lys Gly Ile Pro Arg Asn Glu Asn Leu
    50                  55                  60

Ala Ala Asp Arg Phe Gln Lys Ala Ala Glu Leu Glu Asn Ala Glu Ala
65                  70                  75                  80

Gln Ala Asn Leu Ala Ala Leu Tyr Arg Asn Ser Leu Val Val Pro Arg
                85                  90                  95

Asp Asn Ala Lys Val Ile Tyr Trp Ala Gln Lys Ala Ala Glu His Gly
            100                 105                 110

Asn Pro Arg Gly Gln Asn Ile Leu Gly Phe Met Tyr Met Ile Gly Glu
        115                 120                 125

Gly Val Gln Gln Asp Asp Ala Lys Ala Ala Ser Trp Tyr Gln Lys Ala
    130                 135                 140

Ala Glu Gln Gly Phe Ala Gly Gly Gln Arg Asn Leu Ala Phe Met Tyr
145                 150                 155                 160

Leu Asn Gly Lys Gly Val Pro Gln Asp Asp Ala Thr Ala Thr Tyr Trp
                165                 170                 175

Tyr Gln Lys Ala Ala Asn Gln Gly Asp Ile Gln Ala Gln Lys Ser Leu
            180                 185                 190

Lys Met Ile Gln Glu Lys Ser Lys Glu Met Ser Asn Tyr Asn Leu Asn
        195                 200                 205

Thr Val Gln Gln Ser Pro Pro Gln Ala Ser Ser His Gln Pro Leu Pro
    210                 215                 220

Lys Ala Ser Pro Ser Asn Glu Arg Asn Leu Ser Pro Leu Lys Asn Ile
225                 230                 235                 240

Phe Asp Lys Leu Lys Gln Asn Ser Ala Lys Met Lys Ser Ala Pro Pro
                245                 250                 255

Gly Asn Glu Glu Gln Asp Tyr Leu Lys
            260                 265
```

<210> SEQ ID NO 41
<211> LENGTH: 888
<212> TYPE: DNA
<213> ORGANISM: Oxalobacter formigenes

<400> SEQUENCE: 41

```
atgaacagcc agactgccag aaaaatgttt tctttcgata tcagggcaaa ccatttttt      60 cgagcttttt tgctgcttgc catgtcactt cttgccggtg ttgcctttgc tgacgatttc    120
aacgatggtg tcagcgccta caaaagcggg aactaccagc aggcactgtc gctatttgag    180
gcgggcgcga aaaggacga cccgaaatcg acgtatgccc tcggccttct gtataaaaac     240
ggcgtgatcg tcagaaaaga tatcggacgt ggcctgaatc tgatcatgaa atctgccaat    300
cagggattcg cgagagccca gaattatctc ggagtcacct actacgatgg caatgaggtc    360
```

-continued

```
gaacaggact acaaggaagc gttcgactgg tatggcaagg cagccgttca gggttatcct    420
gatgcggaat acaatctggc cgtcatgtat ggtcttggga agggaacccg gcaggatttt    480
tccgaaacca tcaaatggct gcgcaaggcc gccatgcacc agcttcctga agcccagtac    540
ggtcttggcg taatgtattc ccgaggactt ggtgtcgtga aaaacgatga acagtccgct    600
tactggtttt caaaggcagc gcgggccggt tacctgaaag cgcaaaacaa actgggtatt    660
ttatattccg aaggaaaagg tctggaaaag gacgagaaaa aagcgttcca ctggttcgag    720
gccgctgccg aaaaaggcta tgcaaaagcc caattcaatc tggcggtcat gtacgacaag    780
ggaattggcg ttgcaaagga tgtgtccaaa gccattatgt ggtaccgcaa agcggctaca    840
caaggcaatg tggctgcaca gaaacggttg aaacaactgc attcctaa               888
```

<210> SEQ ID NO 42
<211> LENGTH: 295
<212> TYPE: PRT
<213> ORGANISM: Oxalobacter formigenes

<400> SEQUENCE: 42

```
Met Asn Ser Gln Thr Ala Arg Lys Met Phe Ser Phe Asp Ile Arg Ala
1               5                   10                  15

Asn His Phe Phe Arg Ala Phe Leu Leu Ala Met Ser Leu Leu Ala
            20                  25                  30

Gly Val Ala Phe Ala Asp Asp Phe Asn Asp Gly Val Ser Ala Tyr Lys
        35                  40                  45

Ser Gly Asn Tyr Gln Gln Ala Leu Ser Leu Phe Glu Ala Gly Ala Lys
    50                  55                  60

Lys Asp Asp Pro Lys Ser Thr Tyr Ala Leu Gly Leu Leu Tyr Lys Asn
65                  70                  75                  80

Gly Val Ile Val Arg Lys Asp Ile Gly Arg Gly Leu Asn Leu Ile Met
                85                  90                  95

Lys Ser Ala Asn Gln Gly Phe Ala Arg Ala Gln Asn Tyr Leu Gly Val
            100                 105                 110

Thr Tyr Tyr Asp Gly Asn Glu Val Glu Gln Asp Tyr Lys Glu Ala Phe
        115                 120                 125

Asp Trp Tyr Gly Lys Ala Ala Val Gln Gly Tyr Pro Asp Ala Glu Tyr
    130                 135                 140

Asn Leu Ala Val Met Tyr Gly Leu Gly Lys Gly Thr Arg Gln Asp Phe
145                 150                 155                 160

Ser Glu Thr Ile Lys Trp Leu Arg Lys Ala Met His Gln Leu Pro
                165                 170                 175

Glu Ala Gln Tyr Gly Leu Gly Val Met Tyr Ser Arg Gly Leu Gly Val
            180                 185                 190

Val Lys Asn Asp Glu Gln Ser Ala Tyr Trp Phe Ser Lys Ala Ala Arg
        195                 200                 205

Ala Gly Tyr Leu Lys Ala Gln Asn Lys Leu Gly Ile Leu Tyr Ser Glu
    210                 215                 220

Gly Lys Gly Leu Glu Lys Asp Glu Lys Ala Phe His Trp Phe Glu
225                 230                 235                 240

Ala Ala Ala Glu Lys Gly Tyr Ala Lys Ala Gln Phe Asn Leu Ala Val
                245                 250                 255

Met Tyr Asp Lys Gly Ile Gly Val Ala Lys Asp Val Ser Lys Ala Ile
            260                 265                 270

Met Trp Tyr Arg Lys Ala Ala Thr Gln Gly Asn Val Ala Ala Gln Lys
        275                 280                 285
```

Arg Leu Lys Gln Leu His Ser
    290                 295

<210> SEQ ID NO 43
<211> LENGTH: 459
<212> TYPE: DNA
<213> ORGANISM: Oxalobacter formigenes

<400> SEQUENCE: 43
ttgaaagagt tcaatatcct gcaaggagcg attatgagca aacccagagt tcaaaagacg    60
gatgccgaat ggagagcgca gctttcccct gtggcgtatg ccgtgacccg acaggcagcg   120
acggaaccgc cctttaccgg cgagtactgg aaccatgacg agaccggtgt ttatacgtgc   180
gtcaattgtg gaacgcccct gttcatttcc gatacgaaat tcgacgccgg ttgtggctgg   240
ccaagttttt ttgcaccgat cgaccctgaa aatgtaaggg aaaaggtcga tgtctcgctg   300
ggcatggtgc gtaccgaaat tatctgtgcc atttgtgatg cccatctggg ccatgtgttt   360
gacgacggcc caccccaac ggggctgcgt tattgtatta attctgccgc tttgcggttc   420
gacccgctac cgaagaaggc agaatcttct gacaagtga                          459

<210> SEQ ID NO 44
<211> LENGTH: 152
<212> TYPE: PRT
<213> ORGANISM: Oxalobacter formigenes

<400> SEQUENCE: 44

Met Lys Glu Phe Asn Ile Leu Gln Gly Ala Ile Met Ser Lys Pro Arg
1               5                   10                  15

Val Gln Lys Thr Asp Ala Glu Trp Arg Ala Gln Leu Ser Pro Val Ala
            20                  25                  30

Tyr Ala Val Thr Arg Gln Ala Ala Thr Glu Pro Pro Phe Thr Gly Glu
        35                  40                  45

Tyr Trp Asn His Asp Glu Thr Gly Val Tyr Thr Cys Val Asn Cys Gly
    50                  55                  60

Thr Pro Leu Phe Ile Ser Asp Thr Lys Phe Asp Ala Gly Cys Gly Trp
65                  70                  75                  80

Pro Ser Phe Phe Ala Pro Ile Asp Pro Glu Asn Val Arg Glu Lys Val
                85                  90                  95

Asp Val Ser Leu Gly Met Val Arg Thr Glu Ile Ile Cys Ala Ile Cys
            100                 105                 110

Asp Ala His Leu Gly His Val Phe Asp Asp Gly Pro Pro Thr Gly
        115                 120                 125

Leu Arg Tyr Cys Ile Asn Ser Ala Ala Leu Arg Phe Asp Pro Leu Pro
    130                 135                 140

Lys Lys Ala Glu Ser Ser Asp Lys
145                 150

<210> SEQ ID NO 45
<211> LENGTH: 900
<212> TYPE: DNA
<213> ORGANISM: Oxalobacter formigenes

<400> SEQUENCE: 45
atgcaagaaa aaaacagac gcaaagctgg ttcagcaaat acgccaccct gctgattctg    60
gtcatcctga tcgcacctgc cggactggtt ttcgcaagtc gcaagacgc cgccaaaggc   120
atggcgctct atgaaacgaa acactatcag gatgctttcc cgctcctgaa aaaagccgct   180

```
gaagaaggcg acgtgaccgc ccagctctac gttggcaaca tgtaccgtga aggcctcggc    240
gtcaaaaaag attacgcaaa aaccattcca tggtttgaaa aagccgccaa tgccggcaat    300
gccaaagcgc aaacctacct cggcatcgcc tacagcgaag ccttggcgt cgctcccgac    360 tacaccaaag ccgcccagtg gtttgaaaaa gccgccaacc agaactacgg cccggcccag    420
actttggttg cgttatgta ttacaaggga atgggcgttg aacaaaactt cggaaccgcc    480
aaaatgtggc ttgaaaaagc atctgcacag ggcgaaaaag acgcacagtc cttcctcggc    540
ctcatgtacc ttgaaggcga cgacaacaac aagaacccga aaaaggccgt gaactcctg     600 acaaaggcag ccgatcagaa cgaaccgctg gcccagaccg tactcggcat catgtacatc    660
cagggcaaat tcgtcaaaca ggactacaaa aaagcggaag aactgctgac aaaggcgcc    720 gaagccggca ataccgacgc agcgaccttc ctcggcaaca tgtactaccg tggccagggc    780
gttgacaagg acaaggccaa agccgtcaaa tggctggaaa agccgccat ccgtggcgac     840 gtcgatgcac aggaactgct ccaccgcatc cactacggca cccccggcgc accgaaataa    900
```

<210> SEQ ID NO 46
<211> LENGTH: 299
<212> TYPE: PRT
<213> ORGANISM: Oxalobacter formigenes

<400> SEQUENCE: 46

```
Met Gln Glu Lys Lys Gln Thr Gln Ser Trp Phe Ser Lys Tyr Ala Thr
1               5                   10                  15

Leu Leu Ile Leu Val Ile Leu Ile Ala Pro Ala Gly Leu Val Phe Ala
            20                  25                  30

Ser Pro Gln Asp Ala Ala Lys Gly Met Ala Leu Tyr Glu Thr Lys His
        35                  40                  45

Tyr Gln Asp Ala Phe Pro Leu Leu Lys Lys Ala Ala Glu Glu Gly Asp
    50                  55                  60

Val Thr Ala Gln Leu Tyr Val Gly Asn Met Tyr Arg Glu Gly Leu Gly
65                  70                  75                  80

Val Lys Lys Asp Tyr Ala Lys Thr Ile Pro Trp Phe Glu Lys Ala Ala
                85                  90                  95

Asn Ala Gly Asn Ala Lys Ala Gln Thr Tyr Leu Gly Ile Ala Tyr Ser
            100                 105                 110

Glu Gly Leu Gly Val Ala Pro Asp Tyr Thr Lys Ala Ala Gln Trp Phe
        115                 120                 125

Glu Lys Ala Ala Asn Gln Asn Tyr Gly Pro Ala Gln Thr Leu Val Gly
    130                 135                 140

Val Met Tyr Tyr Lys Gly Met Gly Val Glu Gln Asn Phe Gly Thr Ala
145                 150                 155                 160

Lys Met Trp Leu Glu Lys Ala Ser Ala Gln Gly Glu Lys Asp Ala Gln
                165                 170                 175

Ser Phe Leu Gly Leu Met Tyr Leu Glu Gly Asp Asp Asn Asn Lys Asn
            180                 185                 190

Pro Lys Lys Ala Val Glu Leu Leu Thr Lys Ala Ala Asp Gln Asn Glu
        195                 200                 205

Pro Leu Ala Gln Thr Val Leu Gly Ile Met Tyr Ile Gln Gly Lys Phe
    210                 215                 220

Val Lys Gln Asp Tyr Lys Lys Ala Glu Glu Leu Leu Thr Lys Gly Ala
225                 230                 235                 240

Glu Ala Gly Asn Thr Asp Ala Ala Thr Phe Leu Gly Asn Met Tyr Tyr
```

```
            245                 250                 255
Arg Gly Gln Gly Val Asp Lys Asp Lys Ala Lys Ala Val Lys Trp Leu
        260                 265                 270

Glu Lys Ala Ala Ile Arg Gly Asp Val Asp Ala Gln Glu Leu Leu His
        275                 280                 285

Arg Ile His Tyr Gly Thr Pro Gly Ala Pro Lys
        290                 295

<210> SEQ ID NO 47
<211> LENGTH: 669
<212> TYPE: DNA
<213> ORGANISM: Oxalobacter formigenes

<400> SEQUENCE: 47
atggcaaaca aaactttca gaaaaccctg ctgggttgct ccatcgccct gatgtccgct      60
ttcgtcgccg gcaatgccag cgcggccaaa aaagtcgacg acacctactc cagactgaac    120
cagtgtatcg gctactacaa ccagagccag tacacccagg caatcccctg ctttactcca    180
ctggcaaaag ccggtaacga tcaggcacag acctatctgg catcatgta ccagcacggt     240 ttcggtaccc aaaaagacat ggcaaccgct gccatgtggt ataacagggc cgcccgtcag    300
ggagacaaat gggcctacga caacctcaaa gccatgggta atccgaaact ggcaaccggc    360
aaaacctggg cggattacag aaacaccgtc gaacagaaag ccgctgcggg tgaagcctcg    420
gcccagaccg ctctgggcag cctgtactac ttcggtgtcg gtggcgtcaa acaggactac    480
aacaccgcca aaactggta tgccaaagcc gccgtcaatg cgatgcagc cgccatgaac     540 tacctcggtc gcatgtatta ctacgcactg ggcgtcgaac agaattccat gatggccaaa    600
caatacctga cgcagccgc caaagccggt aacgttcagg caaaaaacct gctgaaaaaa   660
atcaaataa                                                          669

<210> SEQ ID NO 48
<211> LENGTH: 222
<212> TYPE: PRT
<213> ORGANISM: Oxalobacter formigenes

<400> SEQUENCE: 48

Met Ala Asn Lys Thr Phe Gln Lys Thr Leu Leu Gly Cys Ser Ile Ala
1               5                   10                  15

Leu Met Ser Ala Phe Val Ala Gly Asn Ala Ser Ala Ala Lys Lys Val
            20                  25                  30

Asp Asp Thr Tyr Ser Arg Leu Asn Gln Cys Ile Gly Tyr Tyr Asn Gln
        35                  40                  45

Ser Gln Tyr Thr Gln Ala Ile Pro Cys Phe Thr Pro Leu Ala Lys Ala
    50                  55                  60

Gly Asn Asp Gln Ala Gln Thr Tyr Leu Gly Ile Met Tyr Gln His Gly
65                  70                  75                  80

Phe Gly Thr Gln Lys Asp Met Ala Thr Ala Ala Met Trp Tyr Asn Arg
                85                  90                  95

Ala Ala Arg Gln Gly Asp Lys Trp Ala Tyr Asp Asn Leu Lys Ala Met
            100                 105                 110

Gly Asn Pro Lys Leu Ala Thr Gly Lys Thr Trp Ala Asp Tyr Arg Asn
        115                 120                 125

Thr Val Glu Gln Lys Ala Ala Ala Gly Glu Ala Ser Ala Gln Thr Ala
    130                 135                 140

Leu Gly Ser Leu Tyr Tyr Phe Gly Val Gly Gly Val Lys Gln Asp Tyr
```

```
145                 150                 155                 160
Asn Thr Ala Lys Asn Trp Tyr Ala Lys Ala Ala Val Asn Gly Asp Ala
                165                 170                 175

Ala Ala Met Asn Tyr Leu Gly Arg Met Tyr Tyr Ala Leu Gly Val
            180                 185                 190

Glu Gln Asn Ser Met Met Ala Lys Gln Tyr Leu Asn Ala Ala Lys
        195                 200                 205

Ala Gly Asn Val Gln Ala Lys Asn Leu Leu Lys Lys Ile Lys
    210                 215                 220

<210> SEQ ID NO 49
<211> LENGTH: 942
<212> TYPE: DNA
<213> ORGANISM: Oxalobacter formigenes

<400> SEQUENCE: 49
atgttgctga tggatattcg aatagaaaaa ctgaagataa aaacgatct caaagataat    60 aatttcttga ccgaacttag caatgctgat gataatgaat cagcattgct tctttattat   120
gaaatgatga aactatctt aaaagcttta tttgtttgtc ttttttttctt cctcggcaat   180 catgcaattg ccgataatct catggaagga ataggctat cgatgctgg acaatataag    240 gaagccatga ccttctctat gcaacccgat gtacatgatg atccagaagc attaaatctt   300
gtcgcttata tgtataacca tggccttggc gtcagcaaaa atgctgaaaa agcatttatg   360
tgctatatga aatcggcaga atccggatta gctattgctc aatttaacgt gggactggcg   420
tatgaacagg gtaacggtat cctgaaaaat cttccagaag cagtcaagtg gtatagaaaa   480
gctgctgaac aagaagatgc tgatgctgaa gcaaaaatgg ttatttgac tgtaaacggc    540 ataggtatcg gaaagaatta taagaagcc atgaaatggt atcaaaggggc ggccgaacat   600 ggagattatg attcgtatgc cgatatcggt atgatgtatt ccaggggaga tggtgtcaaa   660
aggaatttga accatgcagt tcagtattac atttttgggg ctcaaaaagg cagtacatat   720
tcacaggctt tattgggaaa tgcatatgca tacggaaaag gtatccaaaa ggacatagaa   780
caagcactct actggtacaa gcaggctgcc agaaacggaa acgtcaatgc catgaaagaa   840
ctcggctaca tatacgagac cggtcgactt ggtgtgaaaa aagacccaaa agaagcacaa   900
tactggaaag acatggctga agagcgggc aaaaaacagt aa                      942

<210> SEQ ID NO 50
<211> LENGTH: 313
<212> TYPE: PRT
<213> ORGANISM: Oxalobacter formigenes

<400> SEQUENCE: 50

Met Leu Leu Met Asp Ile Arg Ile Glu Lys Leu Lys Ile Lys Asn Asp
1               5                   10                  15

Leu Lys Asp Asn Asn Phe Leu Thr Glu Leu Ser Asn Ala Asp Asp Asn
            20                  25                  30

Glu Ser Ala Leu Leu Leu Tyr Tyr Glu Met Met Lys Thr Ile Leu Lys
        35                  40                  45

Ala Leu Phe Val Cys Leu Phe Phe Leu Gly Asn His Ala Ile Ala
    50                  55                  60

Asp Asn Leu Met Glu Gly Asn Arg Leu Phe Asp Ala Gly Gln Tyr Lys
65                  70                  75                  80

Glu Ala Met Thr Phe Leu Met Gln Pro Asp Val His Asp Asp Pro Glu
                85                  90                  95
```

```
Ala Leu Asn Leu Val Ala Tyr Met Tyr Asn His Gly Leu Gly Val Ser
            100                 105                 110

Lys Asn Ala Glu Lys Ala Phe Met Cys Tyr Met Lys Ser Ala Glu Ser
            115                 120                 125

Gly Leu Ala Ile Ala Gln Phe Asn Val Gly Leu Ala Tyr Glu Gln Gly
            130                 135                 140

Asn Gly Ile Leu Lys Asn Leu Pro Glu Ala Val Lys Trp Tyr Arg Lys
145                 150                 155                 160

Ala Ala Glu Gln Glu Asp Ala Asp Ala Glu Ala Lys Met Gly Tyr Leu
                165                 170                 175

Thr Val Asn Gly Ile Gly Ile Gly Lys Asn Tyr Lys Glu Ala Met Lys
            180                 185                 190

Trp Tyr Gln Arg Ala Ala Glu His Gly Asp Tyr Asp Ser Tyr Ala Asp
            195                 200                 205

Ile Gly Met Met Tyr Ser Arg Gly Asp Gly Val Lys Arg Asn Leu Asn
            210                 215                 220

His Ala Val Gln Tyr Tyr Ile Phe Gly Ala Gln Lys Gly Ser Thr Tyr
225                 230                 235                 240

Ser Gln Ala Leu Leu Gly Asn Ala Tyr Ala Tyr Gly Lys Gly Ile Gln
                245                 250                 255

Lys Asp Ile Glu Gln Ala Leu Tyr Trp Tyr Lys Gln Ala Ala Arg Asn
            260                 265                 270

Gly Asn Val Asn Ala Met Lys Glu Leu Gly Tyr Ile Tyr Glu Thr Gly
            275                 280                 285

Arg Leu Gly Val Lys Lys Asp Pro Lys Glu Ala Gln Tyr Trp Lys Asp
            290                 295                 300

Met Ala Glu Arg Ala Gly Lys Lys Gln
305                 310

<210> SEQ ID NO 51
<211> LENGTH: 195
<212> TYPE: DNA
<213> ORGANISM: Oxalobacter formigenes

<400> SEQUENCE: 51
atgcctatgg aaaaggaatt tccaaagata ccaaaagccc tctactggta caaaaccgca      60
gccaaaaacg gaaacgtcaa tgccatgaaa gaactgggtt ccatttatgc agaaggtgat     120
ctcggagtcc aaaaggacat acaagaagcg aaacgatgga cgacatggcc agaaaagcg      180 gaacaaaaga aataa                                                       195

<210> SEQ ID NO 52
<211> LENGTH: 64
<212> TYPE: PRT
<213> ORGANISM: Oxalobacter formigenes

<400> SEQUENCE: 52

Met Pro Met Glu Lys Glu Phe Pro Lys Ile Pro Lys Ala Leu Tyr Trp
1               5                   10                  15

Tyr Lys Thr Ala Ala Lys Asn Gly Asn Val Asn Ala Met Lys Glu Leu
            20                  25                  30

Gly Ser Ile Tyr Ala Glu Gly Asp Leu Gly Val Gln Lys Asp Ile Gln
            35                  40                  45

Glu Ala Lys Arg Trp Asn Asp Met Ala Arg Lys Ala Glu Gln Lys Lys
        50                  55                  60
```

<210> SEQ ID NO 53
<211> LENGTH: 948
<212> TYPE: DNA
<213> ORGANISM: Oxalobacter formigenes

<400> SEQUENCE: 53

```
atggttacgc ccgaatcgga taatgaaatc gacgacatca tctggtcaga aattgaatcc      60
agtgattcgc acggtgattt cgtctgctat gccgttcacg ctccatataa ggcaaaatat    120
ctggagaatg ccaaagctcg tatcgaatcc ggaaaatatc tggacaacct cgctcctgtc    180
cgctatctga aggctgttga acgtattgaa aaactggccg gaacgggcga cccggcggca    240
acattccaca tgggaaaaat atatgccatt ggcattgccg ttccgcaaaa tgtacccaaa    300
gccgttgaat ggtatgaaaa ggccatcgca ctcggagaac ccagagctta cgccaatctc    360
ggctggtttt atcaatcggg ttacggtgtt ccgactgaca aatcgaaagc tttcgaattg    420
ctgtcgttcg gtgctgaaaa cggagttttg tctgcaaagg ctgccatcgg catgatgctt    480
ttgaacgggg aaggatgtac cctgaatccg gaactcgggt tcagaaaact tgaggaatcg    540
ttcaacagcg gttatctgaa tgcgggcaac cacatttctg atgtgtattt tgaaggcaaa    600
ctggttccag gggatatcga gcttgcccat gaatggctac agaaagtggc ggatagcggc    660
gatgaaagat caatggcgat ccttggccac tatcttgtga caggaagtca tggaaagaca    720
gacacggcaa aagggcttga tttgcttgag caggcaaccc gactgcaata tctgcctgcc    780
tatttatggc tgggtacctt gtacaaaaaa gggcttggcg ttgagctgga tgccgaaaaa    840
gccattgaat ggttcaaaaa gggcatcaag gcgggctgtc gcgactgcca gatagcactt    900
acgatgatgt ccatgcctga acggacaat ccgaagtcgt atcattaa                  948
```

<210> SEQ ID NO 54
<211> LENGTH: 315
<212> TYPE: PRT
<213> ORGANISM: Oxalobacter formigenes

<400> SEQUENCE: 54

```
Met Val Thr Pro Glu Ser Asp Asn Glu Ile Asp Asp Ile Ile Trp Ser
1               5                   10                  15

Glu Ile Glu Ser Ser Asp Ser His Gly Asp Phe Val Cys Tyr Ala Val
            20                  25                  30

His Ala Pro Tyr Lys Ala Lys Tyr Leu Glu Asn Ala Lys Ala Arg Ile
        35                  40                  45

Glu Ser Gly Lys Tyr Leu Asp Asn Leu Ala Pro Val Arg Tyr Leu Lys
    50                  55                  60

Ala Val Glu Arg Ile Glu Lys Leu Ala Gly Thr Gly Asp Pro Ala Ala
65                  70                  75                  80

Thr Phe His Met Gly Lys Ile Tyr Ala Ile Gly Ile Ala Val Pro Gln
                85                  90                  95

Asn Val Pro Lys Ala Val Glu Trp Tyr Glu Lys Ala Ile Ala Leu Gly
            100                 105                 110

Glu Pro Arg Ala Tyr Ala Asn Leu Gly Trp Phe Tyr Gln Ser Gly Tyr
        115                 120                 125

Gly Val Pro Thr Asp Lys Ser Lys Ala Phe Glu Leu Ser Phe Gly
    130                 135                 140

Ala Glu Asn Gly Val Leu Ser Ala Lys Ala Ala Ile Gly Met Met Leu
145                 150                 155                 160

Leu Asn Gly Glu Gly Cys Thr Leu Asn Pro Glu Leu Gly Phe Gln Lys
```

165                 170                 175
Leu Glu Glu Ser Phe Asn Ser Gly Tyr Leu Asn Ala Gly Asn His Ile
            180                 185                 190

Ser Asp Val Tyr Phe Glu Gly Lys Leu Val Pro Gly Asp Ile Glu Leu
        195                 200                 205

Ala His Glu Trp Leu Gln Lys Val Ala Asp Ser Gly Asp Glu Arg Ser
    210                 215                 220

Met Ala Ile Leu Gly His Tyr Leu Val Thr Gly Ser His Gly Lys Thr
225                 230                 235                 240

Asp Thr Ala Lys Gly Leu Asp Leu Leu Glu Gln Ala Thr Arg Leu Gln
                245                 250                 255

Tyr Leu Pro Ala Tyr Leu Trp Leu Gly Thr Leu Tyr Lys Lys Gly Leu
            260                 265                 270

Gly Val Glu Leu Asp Ala Glu Lys Ala Ile Glu Trp Phe Lys Lys Gly
        275                 280                 285

Ile Lys Ala Gly Cys Arg Asp Cys Gln Ile Ala Leu Thr Met Met Ser
    290                 295                 300

Met Pro Glu Thr Asp Asn Pro Lys Ser Tyr His
305                 310                 315

<210> SEQ ID NO 55
<211> LENGTH: 912
<212> TYPE: DNA
<213> ORGANISM: Oxalobacter formigenes

<400> SEQUENCE: 55
atgaacaagc cttatccaaa cctgtcattt caaatgaaat cttttttcaa gatcttctgt    60
atagtctgtc tgtttctttt cagtgttcct tcttttgccg acaacgccaa ggaaggcatg   120
cgtctgttcc aggctggaaa atatcagcag gccatgacat atttcatgaa gccggatgcc   180
caaaagaatc cggatgtatt aaaccgcata gcttatatgt atgacaaagg ctttggtgtt   240
gaaaagaatc tgcaaacaag tgtcaagtgg tataaaaaag cagctgaaat gggattcaaa   300
gtagcacagt tcaatctcgg attaagttat caaaaaggct tgggagttcc aaaagatatc   360
aatgaagcca tcaaatggta ccgtaaatca gcagaacagg gatatcccag cgccgaatcc   420
aaaatgggtt atttcactgt caagggaaaa ggaataaaac aggattttgc acaagccttg   480
aaatggtatc gtctcgctgc tgaacatggc gatgaccgtt cttatgccga tatcggcatt   540
ttttatgccg aaggttatgg cgtcaaaaaa gacaggaacc gtgccgtgca gtattacatc   600
atgggtgctg aaaaaggcga cgcttatgcc cagtatcttt taggccgcgc ctatgagcag   660
gggcggggca ttcaatactc tcccgaacgt tcactttact ggctcaaaaa agctgccgac   720
aatggaagtt tccttgccat gaaagaactc gggatcgttt atgccaatgg acttctggac   780
cagaaaatgg atacggatgc tgccgcaaaa tggggtgaaa aagcctggga aacccgcaag   840
aagaacgggg aatccgatcc ggaggtcgac cgcagactgc gcttttttcgg catagacccg   900 gatgacttat ag                                                        912

<210> SEQ ID NO 56
<211> LENGTH: 303
<212> TYPE: PRT
<213> ORGANISM: Oxalobacter formigenes

<400> SEQUENCE: 56

Met Asn Lys Pro Tyr Pro Asn Leu Ser Phe Gln Met Lys Ser Phe Phe
1               5                   10                  15

```
Lys Ile Phe Cys Ile Val Cys Leu Phe Leu Phe Ser Val Pro Ser Phe
            20                  25                  30

Ala Asp Asn Ala Lys Glu Gly Met Arg Leu Phe Gln Ala Gly Lys Tyr
        35                  40                  45

Gln Gln Ala Met Thr Tyr Phe Met Lys Pro Asp Ala Gln Lys Asn Pro
    50                  55                  60

Asp Val Leu Asn Arg Ile Ala Tyr Met Tyr Asp Lys Gly Phe Gly Val
65                  70                  75                  80

Glu Lys Asn Leu Gln Thr Ser Val Lys Trp Tyr Lys Lys Ala Ala Glu
                85                  90                  95

Met Gly Phe Lys Val Ala Gln Phe Asn Leu Gly Leu Ser Tyr Gln Lys
            100                 105                 110

Gly Leu Gly Val Pro Lys Asp Ile Asn Glu Ala Ile Lys Trp Tyr Arg
        115                 120                 125

Lys Ser Ala Glu Gln Gly Tyr Pro Ser Ala Glu Ser Lys Met Gly Tyr
    130                 135                 140

Phe Thr Val Lys Gly Lys Gly Ile Lys Gln Asp Phe Ala Gln Ala Leu
145                 150                 155                 160

Lys Trp Tyr Arg Leu Ala Ala Glu His Gly Asp Asp Arg Ser Tyr Ala
                165                 170                 175

Asp Ile Gly Ile Phe Tyr Ala Glu Gly Tyr Gly Val Lys Lys Asp Arg
            180                 185                 190

Asn Arg Ala Val Gln Tyr Tyr Ile Met Gly Ala Glu Lys Gly Asp Ala
        195                 200                 205

Tyr Ala Gln Tyr Leu Leu Gly Arg Ala Tyr Glu Gln Gly Arg Gly Ile
    210                 215                 220

Gln Tyr Ser Pro Glu Arg Ser Leu Tyr Trp Leu Lys Lys Ala Ala Asp
225                 230                 235                 240

Asn Gly Ser Phe Leu Ala Met Lys Glu Leu Gly Ile Val Tyr Ala Asn
                245                 250                 255

Gly Leu Leu Asp Gln Lys Met Asp Thr Asp Ala Ala Ala Lys Trp Gly
            260                 265                 270

Glu Lys Ala Trp Glu Thr Arg Lys Lys Asn Gly Glu Ser Asp Pro Glu
        275                 280                 285

Val Asp Arg Arg Leu Arg Phe Phe Gly Ile Asp Pro Asp Asp Leu
    290                 295                 300

<210> SEQ ID NO 57
<211> LENGTH: 936
<212> TYPE: DNA
<213> ORGANISM: Oxalobacter formigenes

<400> SEQUENCE: 57
atggcactcc cttctttccc gtcatcccca ttcatcaagt ggctctcccg tctggcgctg      60
gtctgtttca tcctgcccgc gatgccgatc gaagccgttg caaaagaccg gagcgaaggt     120
gtgaagcttt actataacca gcaatacaaa aaggccgccc ctttcctgat gaaagaagcc     180
aaaaaaggca tgccaaggc acaggtctgc ctcgggatga tgtatcagga gggtcttggc     240
ctgaaacaga actacatgct ggccagacgc tggtatgaaa atcggcgaa gaaaaaccgg     300 gctgacgcac aaactttcct cggcatgctc tacagtcagg gcttggtgt ggcgaaagat     360 ttcgaaaaag ccaaatattg gttcgacaag gccgccggac agggctttgc ccctgcccag     420
acactcgtcg gcctgatgta cgccaaaggc gtcggcaccg caaaaagcat gtcgcaagcg     480
```

| | | |
|---|---|---|
| gaaaaatggc tgcggctggc cgccaaacag ggtgaaccgg acgcccagac ctatctgggc | 540 | |
| cttttgtacc ttgacggcac tgaactgccg caggacgtag gtgaagccgc gcgacttttg | 600 | |
| aaagaagcgg ccgtaaaagg cgacccgaac gcccagtctg cactgggcat gatgtatttt | 660 | |
| tccggcaagg gggtcgatca ggacatgaac gagtcgaaaa atggcttga aaaggcggcc | 720 | |
| attgccggta acgtcgatgc acagactttc ctcggcaacc tctattacaa gggtatcggc | 780 | |
| gtcgcgaaag acgatacccg cgcacgctac tggcttcaga aagcggcgat tgccggtgat | 840 | |
| ccggacgcac aggccacatt aaatgatatg ttgaaagacg atgcagcgcc cgttttgccc | 900 | |
| ttcgaggaca agaagcccct ttccggttcc ctgtaa | 936 | |

<210> SEQ ID NO 58
<211> LENGTH: 311
<212> TYPE: PRT
<213> ORGANISM: Oxalobacter formigenes

<400> SEQUENCE: 58

Met Ala Leu Pro Ser Phe Pro Ser Ser Pro Phe Ile Lys Trp Leu Ser
1               5                   10                  15

Arg Leu Ala Leu Val Cys Phe Ile Leu Pro Ala Met Pro Ile Glu Ala
            20                  25                  30

Val Ala Lys Asp Arg Ser Glu Gly Val Lys Leu Tyr Tyr Asn Gln Gln
        35                  40                  45

Tyr Lys Lys Ala Ala Pro Phe Leu Met Lys Glu Ala Lys Lys Gly Asn
    50                  55                  60

Ala Lys Ala Gln Val Cys Leu Gly Met Met Tyr Gln Glu Gly Leu Gly
65                  70                  75                  80

Leu Lys Gln Asn Tyr Met Leu Ala Arg Arg Trp Tyr Glu Lys Ser Ala
                85                  90                  95

Lys Lys Asn Arg Ala Asp Ala Gln Thr Phe Leu Gly Met Leu Tyr Ser
            100                 105                 110

Gln Gly Leu Gly Val Ala Lys Asp Phe Glu Lys Ala Lys Tyr Trp Phe
        115                 120                 125

Asp Lys Ala Ala Gly Gln Gly Phe Ala Pro Ala Gln Thr Leu Val Gly
    130                 135                 140

Leu Met Tyr Ala Lys Gly Val Gly Thr Ala Lys Ser Met Ser Gln Ala
145                 150                 155                 160

Glu Lys Trp Leu Arg Leu Ala Ala Lys Gln Gly Glu Pro Asp Ala Gln
                165                 170                 175

Thr Tyr Leu Gly Leu Leu Tyr Leu Asp Gly Thr Glu Leu Pro Gln Asp
            180                 185                 190

Val Gly Glu Ala Ala Arg Leu Leu Lys Glu Ala Ala Val Lys Gly Asp
        195                 200                 205

Pro Asn Ala Gln Ser Ala Leu Gly Met Met Tyr Phe Ser Gly Lys Gly
    210                 215                 220

Val Asp Gln Asp Met Asn Glu Ser Glu Lys Trp Leu Glu Lys Ala Ala
225                 230                 235                 240

Ile Ala Gly Asn Val Asp Ala Gln Thr Phe Leu Gly Asn Leu Tyr Tyr
                245                 250                 255

Lys Gly Ile Gly Val Ala Lys Asp Asp Thr Arg Ala Arg Tyr Trp Leu
            260                 265                 270

Gln Lys Ala Ala Ile Ala Gly Asp Pro Asp Ala Gln Ala Thr Leu Asn
        275                 280                 285

Asp Met Leu Lys Asp Asp Ala Ala Pro Val Leu Pro Phe Glu Asp Lys

```
                    290                 295                 300
Lys Pro Leu Ser Gly Ser Leu
305                 310

<210> SEQ ID NO 59
<211> LENGTH: 660
<212> TYPE: DNA
<213> ORGANISM: Oxalobacter formigenes

<400> SEQUENCE: 59
atgtccaggg gttccaaaaa caaaaagctt tttttatggc tcattctcgc cgccacgatc      60
atcctgatca tcatcagcca gactgctttc gcagtcggtg agcgcgacct tgaacaggcg     120
atgcagtcct attccgccgg acaatacaaa gaggctgttc cccaattcga aaaagcggca     180
acgctgggca caacaaggc acaaaccatg ctgggtgtcc tgtattttca gggcaaggga      240
tgcgaaaagg actacgtgaa ggccgccgaa tggttcgacc gtgcggccaa tggcggcaat     300
atcgaagcgc aaaccttcat gggcatcatc aatcttgaag gcctcggtac tcccaaaaac     360
gaaaaaacgg cctattactg gttcgaaaaa gccgcccgtg gcggtgaaac cagcgcacag     420
aattatctcg gcaccctgct catgaatgga cagggcacga aaagagactc tgcaaaagcg     480
gctgaatggt ttaccaaagc cgccgaaaag ggtgacctga cgcccggaa atccttggc      540 gcgatgtact ttcagggcac aggcgttgcc aaagacatgg taaaagcccg gtactggctg     600 caaaagcgg ctgatgacgg tgacatggac gcaaaaaaca tgctctccga actcaaataa     660

<210> SEQ ID NO 60
<211> LENGTH: 219
<212> TYPE: PRT
<213> ORGANISM: Oxalobacter formigenes

<400> SEQUENCE: 60

Met Ser Arg Gly Ser Lys Asn Lys Lys Leu Phe Leu Trp Leu Ile Leu
1               5                   10                  15

Ala Ala Thr Ile Ile Leu Ile Ile Ile Ser Gln Thr Ala Phe Ala Val
                20                  25                  30

Gly Glu Arg Asp Leu Glu Gln Ala Met Gln Ser Tyr Ser Ala Gly Gln
            35                  40                  45

Tyr Lys Glu Ala Val Pro Gln Phe Glu Lys Ala Ala Thr Leu Gly Asn
        50                  55                  60

Asn Lys Ala Gln Thr Met Leu Gly Val Leu Tyr Phe Gln Gly Lys Gly
65                  70                  75                  80

Cys Glu Lys Asp Tyr Val Lys Ala Ala Glu Trp Phe Asp Arg Ala Ala
                85                  90                  95

Asn Gly Gly Asn Ile Glu Ala Gln Thr Phe Met Gly Ile Ile Asn Leu
            100                 105                 110

Glu Gly Leu Gly Thr Pro Lys Asn Glu Lys Thr Ala Tyr Tyr Trp Phe
        115                 120                 125

Glu Lys Ala Ala Arg Gly Gly Glu Thr Ser Ala Gln Asn Tyr Leu Gly
    130                 135                 140

Thr Leu Leu Met Asn Gly Gln Gly Thr Lys Arg Asp Ser Ala Lys Ala
145                 150                 155                 160

Ala Glu Trp Phe Thr Lys Ala Ala Glu Lys Gly Asp Leu Asn Ala Arg
                165                 170                 175

Lys Ile Leu Gly Ala Met Tyr Phe Gln Gly Thr Gly Val Ala Lys Asp
            180                 185                 190
```

Met Val Lys Ala Arg Tyr Trp Leu Gln Lys Ala Ala Asp Asp Gly Asp
    195                 200                 205

Met Asp Ala Lys Asn Met Leu Ser Glu Leu Lys
    210                 215

<210> SEQ ID NO 61
<211> LENGTH: 3546
<212> TYPE: DNA
<213> ORGANISM: Oxalobacter formigenes

<400> SEQUENCE: 61

| | | | | | |
|---|---|---|---|---|---|
| atgaattctt | ttcaatggca | cattgtcaaa | ctcaaacacc | gcgcacttct | gtccagcctg | 60 |
| atcgtcgcgg | cggctttcat | tccctttta | tcgacaacag | cagggacagc | aaacccgccc | 120 |
| accattcaga | aaactcccga | acttgcccgt | caggtcaatg | aaacgcttaa | cttcgatcac | 180 |
| aaaacagaag | acatcctgaa | acactgacg | gaatcaaaaa | acccgtccga | taaaaccctg | 240 |
| atgggagcgt | tttacggttc | cggtgcaggt | ggaaaacagg | actggggaaa | agcccggatg | 300 |
| tggtttgaaa | aagcggccag | tgaaggcgat | gcgcacgctg | aatattttct | gggtcttctt | 360 |
| tacatggggg | gtctgggcac | ccccaaagat | tatgacaagg | cgtttcattg | gctattgttg | 420 |
| gccgcccgta | aggacattcc | cgacgcacag | taccagttga | gttggttcta | tgccaacgga | 480 |
| aaaggtacga | gccaaagtct | gcgtgaaacg | gtttactgga | tacaaaaggc | agcccacaag | 540 |
| gggcatgtag | tagccatgcg | aagcatggga | atgctcagtt | actcgggatt | aggcatgccc | 600 |
| gaaaacaagg | tcgacgcttt | caaatggttt | gaaaagcgg | cgagtgcagg | cgatgccgaa | 660 |
| gcccaatatc | accttggcat | gtcctatatg | gcaggcaagg | gaacggaaaa | agacggaaaa | 720 |
| aagggagaag | aatggcttta | tcgtgccgcg | ctgcaaaatc | agacgaaagc | ccaggattat | 780 |
| ctttccgtcc | tttatgtgca | gcgattgctt | gataaaaaaa | acaggccggg | cgaaatcgaa | 840 |
| caggcaagac | agtggctgga | aaacgccgcc | cgacgaaacg | ataaaaatgc | gatatacatg | 900 |
| ctgaacgtca | ttgagcagta | ttctcgcaaa | acatcgaaaa | atcaggccga | aaccctcgac | 960 |
| acccttcgtc | gtcgcgccga | acagggcaat | gccgattccc | aattcatgct | gggagaggcc | 1020 |
| ctgcttgccg | aacgggaat | gaagaaaaat | ccggaagaag | ctgtccgctg | gtttgaaaaa | 1080 |
| gcggcaaaac | agggcaacat | tgatgcacag | tccgccctgg | gatatatgca | ttatttcggc | 1140 |
| gtccatgtcc | ctgtcgatta | cgcaaaagcc | attcccctgt | taaaacaggg | tgccgataag | 1200 |
| gggaacagcc | aggcacaaac | cgctatggga | ttcgcctatg | ccagtggaac | aggaattgcc | 1260 |
| aaaaacgagc | aaaaagcatt | tgaactgttt | gaaaaagcgg | cccggaacaa | tgtccgaagt | 1320 |
| gcccagtttt | acctcggtga | aatgcttgaa | atggcattg | aacccaacg | aaacgtccca | 1380 |
| gagggattgg | catggatcga | aaaatcggcg | aaggcaggat | acgaccaggc | ccagtttacg | 1440 |
| atgggaataa | acgctctccg | tggcaaggac | aagatgcaaa | atattgacga | agcgcgcaaa | 1500 |
| tggatgcgtc | tggccgccaa | acagaatcat | gcagaagccc | agtacatgct | cggcatgtca | 1560 |
| tattttctgg | gagaactgac | accggaaaat | caaaaggaag | gtatttctg | gtgggacaag | 1620 |
| gccgccgccc | aaaatcacgt | cgaagcccgg | ctcatgctgt | tcaagtatca | ctgcgatccc | 1680 |
| aaaatgcatt | atgcggatcg | taaacgatgt | tcctcgatct | ctgaacaaat | gcacgatatc | 1740 |
| cgtgaccctg | acgcgcttta | ttcccttgga | gaattatttt | ttttcggtaa | tgacaaccat | 1800 |
| aaaaaaaacg | tcccgaaagc | tgtcgatttt | ttcagcaagg | cggctgatct | gaaccataca | 1860 |
| gaaagccagt | acatgctggg | gctgattctc | tattccaaaa | cggatgtcgg | acaaaacaaa | 1920 |
| aaacaagcct | gccagtggtt | tgaaaaagcg | gcaagtcaca | atcacccgga | aagccaatat | 1980 |

```
atgctcggaa tctgtgttct cgaggggaac cacacttccg ccgacaaaaa aaaggcgctt    2040
gaactgatca gactggcagc cgacaaaaac gtcagcatcg cccagaacaa atgggggtat    2100
ctgtatgaaa caggccatat cgttccgaaa gacatgaaaa aagccatcga atggtacaca    2160
cttgccgaac agaatggatt tacgatgcg gcttaccatc tggccctgtt gtaccttgcc     2220
agttccccac ccctgcaaaa cgatccgctg gctctgcgtt atcttgaaaa agcggctagc    2280
gcaaacaata caaatgctct ttataaactg gaacgttttt atttccacgg tcaatactcg    2340
gccacaaaag atcggaaaaa agcggcggag tatttccgcc gtgccgccaa actcggccat    2400
aaaaacagcc aaatagccta tgccgacatc ctccaaaaag gtaagggagt tgaaaaaaac    2460
gaaaaactgg cttgcgaaat ctatgaaaaa acagccaaag aaggtagccc ttacggacaa    2520
ttccgctcag gactgtgcta tcagacaggt cttggaaata gacccaaaaa tcctgccaaa    2580
gcggtcagtc tttttgaaca ggcagccaga caaaacctgc cggatggcca gattgccctg    2640
gcatactgtt atgaaaccgg acagggcgtt gcccaaaatc ttgcgctggc gttcaaatgg    2700
tacaaaatgg cagctgaaaa gggagatgtc ggcagcatga tcacaaccgg aaagatgctg    2760
gacaagggag aaggaacagc acgcgacagc aaacaggctt tttactggtt ttcaaaagcg    2820
gctgagaaag gatcacccga agcagaagtt cagttgggcc aactgtatta tgccggacgt    2880
ggcatttccg ctgacatgaa aaaagcggtt tccctcttcg accattcggc cagacaaggc    2940
aacgctttgg ctcaatactg gatgggttat ctctgtcttc acggaaaagg ggtcgaaaaa    3000
aatgagccac tggctcgtga ctggctcgaa aaagccgccg tccagaatca gacaggcgcc    3060
gcttttgaac tggcaaaaca gtattggaat ggcaacggca tcccgtccga tccggaacag    3120
gctattgtct ggttcaccaa agccgcacaa aataacgatg ttcaggcaca agagcactg     3180 gcgttcattt atagcgtcca tggcgcgaaa aagggataa agccggatga ccaaaaagcc    3240
ttttactggg caaacaaagc cgccagatat aacgatgatc cctcgaccag actgttgctg    3300
ggaacgtttt atatctcggg aaaagggacc gctgtagatg aaaaaaaagg ccttctcctt    3360
ctgaaagaag ccgcagagaa aaactatccc caggcaatgg cgatgctggg tgagttctat    3420
cttgagaaaa aagacaggaa agaagcacaa atgtggttca agcgtgctgc cgcctccggt    3480
gatcagaagg tcatcgaaat aatgaagaaa aaaggcgttt atccgcaaaa ccccgtccat    3540
ccctga                                                                3546
```

<210> SEQ ID NO 62
<211> LENGTH: 1181
<212> TYPE: PRT
<213> ORGANISM: Oxalobacter formigenes

<400> SEQUENCE: 62

Met Asn Ser Phe Gln Trp His Ile Val Lys Leu Lys His Arg Ala Leu
1               5                   10                  15

Leu Ser Ser Leu Ile Val Ala Ala Ala Phe Ile Pro Phe Ser Ser Thr
            20                  25                  30

Thr Ala Gly Thr Ala Asn Pro Pro Thr Ile Gln Lys Thr Pro Glu Leu
        35                  40                  45

Ala Arg Gln Val Asn Glu Thr Leu Asn Phe Asp His Lys Thr Glu Asp
    50                  55                  60

Ile Leu Lys Thr Leu Thr Glu Ser Lys Asn Pro Ser Asp Lys Thr Leu
65                  70                  75                  80

Met Gly Ala Phe Tyr Gly Ser Gly Ala Gly Gly Lys Gln Asp Trp Gly

```
            85                  90                  95
Lys Ala Arg Met Trp Phe Glu Lys Ala Ala Ser Glu Gly Asp Ala His
                100                 105                 110
Ala Glu Tyr Phe Leu Gly Leu Leu Tyr Met Gly Gly Leu Gly Thr Pro
            115                 120                 125
Lys Asp Tyr Asp Lys Ala Phe His Trp Leu Leu Ala Ala Arg Lys
    130                 135                 140
Asp Ile Pro Asp Ala Gln Tyr Gln Leu Ser Trp Phe Tyr Ala Asn Gly
145                 150                 155                 160
Lys Gly Thr Ser Gln Ser Leu Arg Glu Thr Val Tyr Trp Ile Gln Lys
                165                 170                 175
Ala Ala His Lys Gly His Val Val Ala Met Arg Ser Met Gly Met Leu
            180                 185                 190
Ser Tyr Ser Gly Leu Gly Met Pro Glu Asn Lys Val Asp Ala Phe Lys
        195                 200                 205
Trp Phe Glu Lys Ala Ala Ser Ala Gly Asp Ala Glu Ala Gln Tyr His
    210                 215                 220
Leu Gly Met Ser Tyr Met Ala Gly Lys Gly Thr Glu Lys Asp Gly Lys
225                 230                 235                 240
Lys Gly Glu Glu Trp Leu Tyr Arg Ala Ala Leu Gln Asn Gln Thr Lys
                245                 250                 255
Ala Gln Asp Tyr Leu Ser Val Leu Tyr Val Gln Arg Leu Leu Asp Lys
            260                 265                 270
Lys Asn Arg Pro Gly Glu Ile Glu Gln Ala Arg Gln Trp Leu Glu Asn
        275                 280                 285
Ala Ala Arg Arg Asn Asp Lys Asn Ala Ile Tyr Met Leu Asn Val Ile
    290                 295                 300
Glu Gln Tyr Ser Arg Lys Thr Ser Lys Asn Gln Ala Glu Thr Leu Asp
305                 310                 315                 320
Thr Leu Arg Arg Arg Ala Glu Gln Gly Asn Ala Asp Ser Gln Phe Met
                325                 330                 335
Leu Gly Glu Ala Leu Leu Ala Gly Thr Gly Met Lys Lys Asn Pro Glu
            340                 345                 350
Glu Ala Val Arg Trp Phe Glu Lys Ala Ala Lys Gln Gly Asn Ile Asp
        355                 360                 365
Ala Gln Ser Ala Leu Gly Tyr Met His Tyr Phe Gly Val His Val Pro
    370                 375                 380
Val Asp Tyr Ala Lys Ala Ile Pro Leu Leu Lys Gln Gly Ala Asp Lys
385                 390                 395                 400
Gly Asn Ser Gln Ala Gln Thr Ala Met Gly Phe Ala Tyr Ala Ser Gly
                405                 410                 415
Thr Gly Ile Ala Lys Asn Glu Gln Lys Ala Phe Glu Leu Phe Glu Lys
            420                 425                 430
Ala Ala Arg Asn Asn Val Arg Ser Ala Gln Phe Tyr Leu Gly Glu Met
        435                 440                 445
Leu Glu Asn Gly Ile Gly Thr Gln Arg Asn Val Pro Glu Gly Leu Ala
    450                 455                 460
Trp Ile Glu Lys Ser Ala Lys Ala Gly Tyr Asp Gln Ala Gln Phe Thr
465                 470                 475                 480
Met Gly Ile Asn Ala Leu Arg Gly Lys Asp Lys Met Gln Asn Ile Asp
                485                 490                 495
Glu Ala Arg Lys Trp Met Arg Leu Ala Ala Lys Gln Asn His Ala Glu
            500                 505                 510
```

```
Ala Gln Tyr Met Leu Gly Met Ser Tyr Phe Leu Gly Glu Leu Thr Pro
        515                 520                 525
Glu Asn Gln Lys Glu Gly Ile Phe Trp Trp Asp Lys Ala Ala Ala Gln
        530                 535                 540
Asn His Val Glu Ala Arg Leu Met Leu Phe Lys Tyr His Cys Asp Pro
545                 550                 555                 560
Lys Met His Tyr Ala Asp Arg Lys Arg Cys Ser Ser Ile Ser Glu Gln
                565                 570                 575
Met His Asp Ile Arg Asp Pro Asp Ala Leu Tyr Ser Leu Gly Glu Leu
                580                 585                 590
Phe Phe Phe Gly Asn Asp Asn His Lys Lys Asn Val Pro Lys Ala Val
        595                 600                 605
Asp Phe Phe Ser Lys Ala Ala Asp Leu Asn His Thr Glu Ser Gln Tyr
        610                 615                 620
Met Leu Gly Leu Ile Leu Tyr Ser Lys Thr Asp Val Gly Gln Asn Lys
625                 630                 635                 640
Lys Gln Ala Cys Gln Trp Phe Glu Lys Ala Ala Ser His Asn His Pro
                645                 650                 655
Glu Ser Gln Tyr Met Leu Gly Ile Cys Val Leu Glu Gly Asn His Thr
                660                 665                 670
Ser Ala Asp Lys Lys Lys Ala Leu Glu Leu Ile Arg Leu Ala Ala Asp
        675                 680                 685
Lys Asn Val Ser Ile Ala Gln Asn Lys Met Gly Tyr Leu Tyr Glu Thr
        690                 695                 700
Gly His Ile Val Pro Lys Asp Met Lys Lys Ala Ile Glu Trp Tyr Thr
705                 710                 715                 720
Leu Ala Glu Gln Asn Gly Phe Thr Asp Ala Ala Tyr His Leu Ala Leu
                725                 730                 735
Leu Tyr Leu Ala Ser Ser Pro Pro Leu Gln Asn Asp Pro Leu Ala Leu
                740                 745                 750
Arg Tyr Leu Glu Lys Ala Ala Ser Ala Asn Asn Thr Asn Ala Leu Tyr
        755                 760                 765
Lys Leu Gly Thr Phe Tyr Phe His Gly Gln Tyr Ser Ala Thr Lys Asp
        770                 775                 780
Arg Lys Lys Ala Ala Glu Tyr Phe Arg Arg Ala Ala Lys Leu Gly His
785                 790                 795                 800
Lys Asn Ser Gln Ile Ala Tyr Ala Asp Ile Leu Gln Lys Gly Lys Gly
                805                 810                 815
Val Glu Lys Asn Glu Lys Leu Ala Cys Glu Ile Tyr Glu Lys Thr Ala
                820                 825                 830
Lys Glu Gly Ser Pro Tyr Gly Gln Phe Arg Ser Gly Leu Cys Tyr Gln
        835                 840                 845
Thr Gly Leu Gly Asn Arg Pro Lys Asn Pro Ala Lys Ala Val Ser Leu
        850                 855                 860
Phe Glu Gln Ala Ala Arg Gln Asn Leu Pro Asp Gly Gln Ile Ala Leu
865                 870                 875                 880
Ala Tyr Cys Tyr Glu Thr Gly Gln Gly Val Ala Gln Asn Leu Ala Leu
                885                 890                 895
Ala Phe Lys Trp Tyr Lys Met Ala Ala Glu Lys Gly Asp Val Gly Ser
                900                 905                 910
Met Ile Thr Thr Gly Lys Met Leu Asp Lys Gly Glu Gly Thr Ala Arg
        915                 920                 925
```

```
Asp Ser Lys Gln Ala Phe Tyr Trp Phe Ser Lys Ala Ala Glu Lys Gly
    930                 935                 940

Ser Pro Glu Ala Glu Val Gln Leu Gly Gln Leu Tyr Tyr Ala Gly Arg
945                 950                 955                 960

Gly Ile Ser Ala Asp Met Lys Lys Ala Val Ser Leu Phe Asp His Ser
                965                 970                 975

Ala Arg Gln Gly Asn Ala Leu Ala Gln Tyr Trp Met Gly Tyr Leu Cys
            980                 985                 990

Leu His Gly Lys Gly Val Glu Lys Asn Glu Pro Leu Ala Arg Asp Trp
        995                 1000                1005

Leu Glu Lys Ala Ala Val Gln Asn Gln Thr Gly Ala Ala Phe Glu
    1010                1015                1020

Leu Ala Lys Gln Tyr Trp Asn Gly Asn Gly Ile Pro Ser Asp Pro
    1025                1030                1035

Glu Gln Ala Ile Val Trp Phe Thr Lys Ala Ala Gln Asn Asn Asp
    1040                1045                1050

Val Gln Ala Gln Arg Ala Leu Ala Phe Ile Tyr Ser Val His Gly
    1055                1060                1065

Ala Lys Lys Gly Ile Lys Pro Asp Asp Gln Lys Ala Phe Tyr Trp
    1070                1075                1080

Ala Asn Lys Ala Ala Arg Tyr Asn Asp Asp Pro Ser Thr Arg Leu
    1085                1090                1095

Leu Leu Gly Thr Phe Tyr Ile Ser Gly Lys Gly Thr Ala Val Asp
    1100                1105                1110

Glu Lys Lys Gly Leu Leu Leu Leu Lys Glu Ala Ala Glu Lys Asn
    1115                1120                1125

Tyr Pro Gln Ala Met Ala Met Leu Gly Glu Phe Tyr Leu Glu Lys
    1130                1135                1140

Lys Asp Arg Lys Glu Ala Gln Met Trp Phe Lys Arg Ala Ala Ala
    1145                1150                1155

Ser Gly Asp Gln Lys Val Ile Glu Ile Met Lys Lys Lys Gly Val
    1160                1165                1170

Tyr Pro Gln Asn Pro Val His Pro
    1175                1180

<210> SEQ ID NO 63
<211> LENGTH: 3852
<212> TYPE: DNA
<213> ORGANISM: Oxalobacter formigenes

<400> SEQUENCE: 63
atgaaccctt tgccatcaga cagccatttt ttcaaacgtt ttgtacgggg atatatcctg      60
ccttgccttt tcttccccat cacggtagcc acagcctctc cggctcagca ccttgtttat     120
ccggagatca tggaaatgcc acaggagata gaccaaaccc tgctggtcga tcatgacagt     180
gaaaaaatac tgaacaaact ggcggactca aacgcccccg ccatgaaaac actcatggga     240
gcctggtacg ctatcggagc cggaggcaaa agggactgga tcaaagcccg catctggttt     300
gaaaaagccg ccactgaagg cgacacaaga gccgcatatc ccctcggtct tttatactcg     360
gccggtctgg gcaccccat cgattacgac aaggcctttt actggctgtc aatcgcggca     420
cgccagaata ttccggatgc ccagtaccgg ctggcaggac tttatcagga aggaaaagga     480
accgccaaaa gcaacgtgaa ttcgcttac tgggtaaaaa aagccgctgg aaacggacac     540
attgacgccc agagagccat ggaatgatc cttcattatg gtctcggagt tcacaaaaac     600
```

```
cttcctgaat cggtcaaatg gtttgaaaaa gcagccaatg ccggaaacgc aaccgcacaa      660
tattatctcg gcatggatta tatgaatggt aatggcctcg ccaaaaatga agggaagga      720 gaaaagtggc tttatcgcgc cgccatgcaa gaccatcttg aagctcaaac atatctcggc      780
accatttatc tgaaacgcaa gcttcaaaat gaaggtcagc caccgaaaac cgcccttgcc      840
atccagtgga tggaaaatgc cgctacgcga aatgacccgt acgctatccg gcttctatcc      900
atggtgtaca ggcatattcc cgaactgcaa acaacgccaa aaggcatgct tcatcttcgc      960
cgcagtgccg agatggggaa tgcatcagcc caattcgatc tcggaagaac cctgtttcag     1020
gataaaaact cacctgcaaa acgcaaggaa gctgtcgtct ggcttgaaaa agccgcgcaa     1080
caggacgaac gtagggcaca ggcttttctt ggtaacatgt attactatgg cgagttcgtt     1140
cctgtcgatt atgtcaaggc gctccctctt ttgatgaggg ctgccgacaa gggagacagc     1200
tttgcacaat acacgcttgg tttggcttat atcgatggga atggcattgc caaagatgaa     1260
cgaaaggctt tttcatggtt ggaaaaatca gccagtcaaa acagggcaag tgcccagtat     1320
tttttaggac ttatgtacct tgatggaaca gggacacctg tcaatgagga aaaaggcatc     1380
cgtttgctca agaattagc aaagacaggg tatgtctatg cccaatataa gcttggtacc     1440
tacgcccata gcgggcttca tatggccaaa gatctggcag aagcgagaaa atggtaccag     1500
ttggcggcca gtcaggatca tatcaaggcg aaatactggc tcggcatgtc cctctttcag     1560
ggcccggaca gtgaacagga caggaaaaaa ggcgtttact ggttcaccga agcagcaaaa     1620
caggatgacc cggatgcgca gcttgaactg ggaaaatccc tgctctacgg cgatggtatc     1680
gacaaaaacg aaaagcaggc gtgcacgtgg ttcaaaaaag ccgccaataa ccaacagcac     1740
accggccagt attacgcagg aatgtgcctt atgcggggca tcaatgggcc ggtcgatatt     1800
ccgaaaggaa tgtcactcat tgaaatgtct gcgaataata aggtctcaat ggcccagttc     1860
cagcttggga aactgtatga atatggtttg aaagagttgc cgaaagacat ctcgaaagcc     1920
attggctggt acacacgtgc cgcagaaaat ggacatgcaa ctgcccaata ccggctggga     1980
aagctttatc tcaaagctga tactccactc aaaaatattc cgctcggcct cgaattcctt     2040
gaaaaatccg cttcacaaaa tataaccagt gccattttg atctgggtaa catttactat     2100
gacggaaaaa ttgtcaaaca ggatatggca aaagcgttga attactttca gaagggaacc     2160
ggactgggcc atctcccgag ccagaatttt gtcggattca tgatcgagaa tggaagcgga     2220
gttaaaaagg ataaagaaaa agcatgcaaa atctatgatg aaaccggtcg acgcggaagt     2280
gcatatggac tttaccgcta tggcttgtgc cagcttccg atcccgatcc atccccggaa     2340
aaccagaaaa aagcgtttat tctttttcgaa caggctgccc gaaaaaatct ggcagacgcc     2400
caatactttt tagccctgtg ttacgaatat ggcaaaggga ctcccaaaaa ccctggcgaa     2460
gctattgaat ggtacaggcg tgcctcggaa aacgacaaac cggaagcact gtaccagttg     2520
ggtatgcttt atatcaccag cccgtctcct cgccaaaaca taccgctggg tctggattat     2580
ctggagaaag cagccgcccg ggatctgtcg tccgcattca acgaactggg ccgaatttat     2640
tatgacggga aaatcgtcag gcaggatctc aaaaaatccg tcttctggta tcgcaaggga     2700
gcacaatcgg gagatacaag aagccagaat gatctggctt atatgatgga atacggtaaa     2760
ggtcttgaaa aagacgaaaa ggcggcctgc acgatgtatg aaaaaacggc aggggaaaaa     2820
aacgcttatg ccagttccg tctgggggctc tgctatctga atggaaaagg cggtaaagcg     2880
aaggatcaac gggaagcagt ccggctcttc gaatctgccg ccggacaaaa tctggcgtct     2940
gcccaatatt ttctgggaat ttaccataaa gaaggtaaag gtgtcgtcaa aaacatgaat     3000
```

-continued

```
gaggctttca aatggtacct gacggcagcc gataacggtc acgtcagttc catgtttgaa   3060
gtcggtaaaa tgttcgctaa tggcagaggt acgaacgcg  acgacaaaaa ggcatttcac   3120
tggtttgaga aagcagctga aaacgggtct gattccgctt tgacccagct gggcattatg   3180
tattataaag gcttgggcat ttcagccgac aaaagcaaag ccgcctcctt ttttttgaaa   3240
gctgccgaaa aaacaattc  atacgcccaa cactggctcg gctatatgta cctgtacggt   3300 aagggggctgg aaaaaacgg  ggagctggca aatcagtggt tatcaaaagc ggctgaccag   3360
aatgaaacgg gcgcgatttt tgaactggga aaacaatact ggtatggcat gggcgtcccg   3420
gtcaatcctg aaaaggcaat cgtcctgctt caaaaagcag ggaacgatgg ccatgttatt   3480
gcacaaagga tactgggcta tatttatgct gatggcggcc cggaaaaagg gattcccctt   3540
gatttcgaaa aggccgtcca atggtttgaa aaagcggccc gacaagacga cgccgccggg   3600
aaaatggggt tggcattgct cactctgacc ggaaaaggaa ctccaaaaaa tgaggagaaa   3660
ggtatccggc ttttgacgca gtctgcaaac atgaattatc catccgcgat ggaactgctc   3720
ggggattttt atcgtgaaga aaaaggtgat aaaaagaag  cggaaaaatg gtatcgtcgt   3780
gccgccgaaa ccggcgacaa aaccgttatc gaatccatga agaaaaaagg cgtttatccg   3840
gcaaacccgt aa                                                      3852
```

<210> SEQ ID NO 64
<211> LENGTH: 1283
<212> TYPE: PRT
<213> ORGANISM: Oxalobacter formigenes

<400> SEQUENCE: 64

```
Met Asn Pro Leu Pro Ser Asp Ser His Phe Phe Lys Arg Phe Val Arg
1               5                   10                  15

Gly Tyr Ile Leu Pro Cys Leu Phe Phe Pro Ile Thr Val Ala Thr Ala
                20                  25                  30

Ser Pro Ala Gln His Leu Val Tyr Pro Glu Ile Met Glu Met Pro Gln
            35                  40                  45

Glu Ile Asp Gln Thr Leu Leu Val Asp His Asp Ser Glu Lys Ile Leu
        50                  55                  60

Asn Lys Leu Ala Asp Ser Asn Ala Pro Ala Met Lys Thr Leu Met Gly
65                  70                  75                  80

Ala Trp Tyr Ala Ile Gly Ala Gly Gly Lys Arg Asp Trp Ile Lys Ala
                85                  90                  95

Arg Ile Trp Phe Glu Lys Ala Ala Thr Glu Gly Asp Thr Arg Ala Ala
                100                 105                 110

Tyr Pro Leu Gly Leu Leu Tyr Ser Ala Gly Leu Gly Thr Pro Ile Asp
            115                 120                 125

Tyr Asp Lys Ala Phe Tyr Trp Leu Ser Ile Ala Ala Arg Gln Asn Ile
        130                 135                 140

Pro Asp Ala Gln Tyr Arg Leu Ala Gly Leu Tyr Gln Glu Gly Lys Gly
145                 150                 155                 160

Thr Ala Lys Ser Glu Arg Glu Phe Ala Tyr Trp Val Lys Lys Ala Ala
                165                 170                 175

Gly Asn Gly His Ile Asp Ala Gln Arg Ala Met Gly Met Ile Leu His
            180                 185                 190

Tyr Gly Leu Gly Val His Lys Asn Leu Pro Glu Ser Val Lys Trp Phe
        195                 200                 205

Glu Lys Ala Ala Asn Ala Gly Asn Ala Thr Ala Gln Tyr Tyr Leu Gly
```

```
             210                 215                 220
Met Asp Tyr Met Asn Gly Asn Gly Leu Ala Lys Asn Glu Arg Glu Gly
225                 230                 235                 240

Glu Lys Trp Leu Tyr Arg Ala Ala Met Gln Asp His Leu Glu Ala Gln
                    245                 250                 255

Thr Tyr Leu Gly Thr Ile Tyr Leu Lys Arg Lys Leu Gln Asn Glu Gly
                260                 265                 270

Gln Pro Pro Glu Thr Ala Leu Ala Ile Gln Trp Met Glu Asn Ala Ala
            275                 280                 285

Thr Arg Asn Asp Pro Tyr Ala Ile Arg Leu Leu Ser Met Val Tyr Arg
        290                 295                 300

His Ile Pro Glu Leu Gln Asn Asn Ala Lys Gly Met Leu His Leu Arg
305                 310                 315                 320

Arg Ser Ala Glu Met Gly Asn Ala Ser Ala Gln Phe Asp Leu Gly Arg
                    325                 330                 335

Thr Leu Phe Gln Asp Lys Asn Ser Pro Ala Lys Arg Lys Glu Ala Val
                340                 345                 350

Val Trp Leu Glu Lys Ala Ala Gln Gln Asp Glu Arg Arg Ala Gln Ala
            355                 360                 365

Phe Leu Gly Asn Met Tyr Tyr Tyr Gly Glu Phe Val Pro Val Asp Tyr
        370                 375                 380

Val Lys Ala Leu Pro Leu Leu Met Arg Ala Ala Asp Lys Gly Asp Ser
385                 390                 395                 400

Phe Ala Gln Tyr Thr Leu Gly Leu Ala Tyr Ile Asp Gly Asn Gly Ile
                    405                 410                 415

Ala Lys Asp Glu Arg Lys Ala Phe Ser Trp Leu Glu Lys Ser Ala Ser
                420                 425                 430

Gln Asn Arg Ala Ser Ala Gln Tyr Phe Leu Gly Leu Met Tyr Leu Asp
            435                 440                 445

Gly Thr Gly Thr Pro Val Asn Glu Glu Lys Gly Ile Arg Leu Leu Lys
        450                 455                 460

Glu Leu Ala Lys Thr Gly Tyr Val Tyr Ala Gln Tyr Lys Leu Gly Thr
465                 470                 475                 480

Tyr Ala His Ser Gly Leu His Met Ala Lys Asp Leu Ala Glu Ala Arg
                    485                 490                 495

Lys Trp Tyr Gln Leu Ala Ala Ser Gln Asp His Ile Lys Ala Lys Tyr
                500                 505                 510

Trp Leu Gly Met Ser Leu Phe Gln Gly Pro Asp Ser Glu Gln Asp Arg
            515                 520                 525

Lys Lys Gly Val Tyr Trp Phe Thr Glu Ala Ala Lys Gln Asp Asp Pro
        530                 535                 540

Asp Ala Gln Leu Glu Leu Gly Lys Ser Leu Leu Tyr Gly Asp Gly Ile
545                 550                 555                 560

Asp Lys Asn Glu Lys Gln Ala Cys Thr Trp Phe Lys Lys Ala Ala Asn
                    565                 570                 575

Asn Gln Gln His Thr Gly Gln Tyr Tyr Ala Gly Met Cys Leu Met Arg
                580                 585                 590

Gly Ile Asn Gly Pro Val Asp Ile Pro Lys Gly Met Ser Leu Ile Glu
            595                 600                 605

Met Ser Ala Asn Asn Lys Val Ser Met Ala Gln Phe Gln Leu Gly Lys
        610                 615                 620

Leu Tyr Glu Tyr Gly Leu Lys Glu Leu Pro Lys Asp Ile Ser Lys Ala
625                 630                 635                 640
```

```
Ile Gly Trp Tyr Thr Arg Ala Ala Glu Asn Gly His Ala Thr Ala Gln
            645                 650                 655

Tyr Arg Leu Gly Lys Leu Tyr Leu Lys Ala Asp Thr Pro Leu Lys Asn
            660                 665                 670

Ile Pro Leu Gly Leu Glu Phe Leu Glu Lys Ser Ala Ser Gln Asn Ile
            675                 680                 685

Thr Ser Ala Ile Phe Asp Leu Gly Asn Ile Tyr Tyr Asp Gly Lys Ile
            690                 695                 700

Val Lys Gln Asp Met Ala Lys Ala Leu Asn Tyr Phe Gln Lys Gly Thr
705                 710                 715                 720

Gly Leu Gly His Leu Pro Ser Gln Asn Phe Val Gly Phe Met Ile Glu
            725                 730                 735

Asn Gly Ser Gly Val Lys Lys Asp Lys Glu Lys Ala Cys Lys Ile Tyr
            740                 745                 750

Asp Glu Thr Gly Arg Arg Gly Ser Ala Tyr Gly Leu Tyr Arg Tyr Gly
            755                 760                 765

Leu Cys Gln Leu Ser Asp Pro Asp Ser Pro Glu Asn Gln Lys Lys
            770                 775                 780

Ala Phe Ile Leu Phe Glu Gln Ala Ala Arg Lys Asn Leu Ala Asp Ala
785                 790                 795                 800

Gln Tyr Phe Leu Ala Leu Cys Tyr Glu Tyr Gly Lys Gly Thr Pro Lys
            805                 810                 815

Asn Pro Gly Glu Ala Ile Glu Trp Tyr Arg Arg Ala Ser Glu Asn Asp
            820                 825                 830

Lys Pro Glu Ala Leu Tyr Gln Leu Gly Met Leu Tyr Ile Thr Ser Pro
            835                 840                 845

Ser Pro Arg Gln Asn Ile Pro Leu Gly Leu Asp Tyr Leu Glu Lys Ala
            850                 855                 860

Ala Ala Arg Asp Leu Ser Ser Ala Phe Asn Glu Leu Gly Arg Ile Tyr
865                 870                 875                 880

Tyr Asp Gly Lys Ile Val Arg Gln Asp Leu Lys Lys Ser Val Phe Trp
            885                 890                 895

Tyr Arg Lys Gly Ala Gln Ser Gly Asp Thr Arg Ser Gln Asn Asp Leu
            900                 905                 910

Ala Tyr Met Met Glu Tyr Gly Lys Gly Leu Glu Lys Asp Glu Lys Ala
            915                 920                 925

Ala Cys Thr Met Tyr Glu Lys Thr Ala Gly Lys Asn Ala Tyr Gly
            930                 935                 940

Gln Phe Arg Leu Gly Leu Cys Tyr Leu Asn Gly Lys Gly Gly Lys Ala
945                 950                 955                 960

Lys Asp Gln Arg Glu Ala Val Arg Leu Phe Glu Ser Ala Ala Gly Gln
            965                 970                 975

Asn Leu Ala Ser Ala Gln Tyr Phe Leu Gly Ile Tyr His Lys Glu Gly
            980                 985                 990

Lys Gly Val Val Lys Asn Met Asn Glu Ala Phe Lys Trp Tyr Leu Thr
            995                 1000                1005

Ala Ala Asp Asn Gly His Val Ser Ser Met Phe Glu Val Gly Lys
            1010                1015                1020

Met Phe Ala Asn Gly Arg Gly Thr Glu Arg Asp Asp Lys Lys Ala
            1025                1030                1035

Phe His Trp Phe Glu Lys Ala Ala Glu Asn Gly Ser Asp Ser Ala
            1040                1045                1050
```

| Leu | Thr | Gln | Leu | Gly | Ile | Met | Tyr | Tyr | Lys | Gly | Leu | Gly | Ile | Ser |
| | 1055 | | | | 1060 | | | | | 1065 | | | | |

Ala Asp Lys Ser Lys Ala Ala Ser Phe Phe Leu Lys Ala Ala Glu
    1070            1075                 1080

Lys Asn Asn Ser Tyr Ala Gln His Trp Leu Gly Tyr Met Tyr Leu
    1085            1090                 1095

Tyr Gly Lys Gly Leu Glu Lys Asn Gly Glu Leu Ala Asn Gln Trp
    1100            1105                 1110

Leu Ser Lys Ala Ala Asp Gln Asn Glu Thr Gly Ala Ile Phe Glu
    1115            1120                 1125

Leu Gly Lys Gln Tyr Trp Tyr Gly Met Gly Val Pro Val Asn Pro
    1130            1135                 1140

Glu Lys Ala Ile Val Leu Leu Gln Lys Ala Gly Asn Asp Gly His
    1145            1150                 1155

Val Ile Ala Gln Arg Ile Leu Gly Tyr Ile Tyr Ala Asp Gly Gly
    1160            1165                 1170

Pro Glu Lys Gly Ile Pro Leu Asp Phe Glu Lys Ala Val Gln Trp
    1175            1180                 1185

Phe Glu Lys Ala Ala Arg Gln Asp Asp Ala Ala Gly Lys Met Gly
    1190            1195                 1200

Leu Ala Leu Leu Thr Leu Thr Gly Lys Gly Thr Pro Lys Asn Glu
    1205            1210                 1215

Glu Lys Gly Ile Arg Leu Leu Thr Gln Ser Ala Asn Met Asn Tyr
    1220            1225                 1230

Pro Ser Ala Met Glu Leu Leu Gly Asp Phe Tyr Arg Glu Glu Lys
    1235            1240                 1245

Gly Asp Lys Lys Glu Ala Glu Lys Trp Tyr Arg Arg Ala Ala Glu
    1250            1255                 1260

Thr Gly Asp Lys Thr Val Ile Glu Ser Met Lys Lys Lys Gly Val
    1265            1270                 1275

Tyr Pro Ala Asn Pro
    1280

<210> SEQ ID NO 65
<211> LENGTH: 1245
<212> TYPE: DNA
<213> ORGANISM: Oxalobacter formigenes

<400> SEQUENCE: 65

```
atgccgtatt ggtccggcgc tcatctgcgc tacaatgaca gcaaaataaa atttcccgtc      60
atgactctat ccctgttccg aaaaattcat atgaaagctg cctttgcctg ctgcgctttc     120
ctgatagcct tgccttttc cgcaagccat gcaggaaata tcgtccattc cgggttgccc     180
ggagcgcccg ttattgtcgg gacggaaaac cggaaacctc cggaaaccgt ctctgaaaac     240
aatgttcccg aagcagcccg ttcaccagtc gatcagaacg acgcaaaaac acagtttcat     300
cttgggctga tgtcgaaaaa cggctatgga gtccctgtcg acccggtaaa agcccgcgaa     360
tggtttgcga agcggccgg acaaaattac cagcccgccc aataccagct tgccctcatg     420
caattttcag gcacaggcgg cacagaaaac aaaagtgccg cgatcgaaca attcaaaaaa     480
ctggcttctg aaggatatgc tcccgcccaa tacacgctcg atatctgaa cctgaaaggc     540
gatggcatcc cgcaaaattc cggagaagcc cgcttctggt tcgaaaaggc cgccgcaaaa     600
aacgatgtgc cgcaaccgc tgcactggca tggctttatc tgaaaggcgt cggcgctccc     660
atcgatgaga aaaaagccgc cgtcctgttt gaaaagctg ccaatatggg tgacgcatac     720
```

```
agccaggatc aattcggcat gatgctcggt cagggaactg gcatgaatgc cgaacccgaa    780
aaagcgtttt tatggattga aaaagcggca accagcaat atccggttgc cgaataccat    840
atggccatga tgtacctgac aggttcggga acggaaaaaa atccggagct agccgtcaaa    900
tggcttgaaa aagccgcttt ccacgggaac gtcgatgccc agaatttcta tgccagcctg    960
ctttatctcg gttatggaat caaacaggac attcccaggg ccatcgggta ttttaccgaa   1020
gcggccgagg gcggacacgc cgaatcccag ttcttgctgg gaaccatcta cgtcaaggga   1080
aatggcgttt taacgaacct gaaaactgcc cgaaactggt ttgaaaaagc ggaaaagaac   1140
ggacaccccg atgcaaaagc cgcactggaa aaactggatg aaatggaagg caaaggccgt   1200
gcaacacctg aaaagaccga taccggcaat cactatccat cttga                  1245
```

<210> SEQ ID NO 66
<211> LENGTH: 414
<212> TYPE: PRT
<213> ORGANISM: Oxalobacter formigenes

<400> SEQUENCE: 66

```
Met Pro Tyr Trp Ser Gly Ala His Leu Arg Tyr Asn Asp Ser Lys Ile
1               5                   10                  15

Lys Phe Pro Val Met Thr Leu Ser Leu Phe Arg Lys Ile His Met Lys
            20                  25                  30

Ala Ala Phe Ala Cys Cys Ala Phe Leu Ile Ala Leu Pro Phe Ser Ala
        35                  40                  45

Ser His Ala Gly Asn Ile Val His Ser Gly Leu Pro Gly Ala Pro Val
    50                  55                  60

Ile Val Gly Thr Glu Asn Arg Lys Pro Pro Glu Thr Val Ser Glu Asn
65                  70                  75                  80

Asn Val Pro Glu Ala Ala Arg Ser Pro Val Asp Gln Asn Asp Ala Lys
                85                  90                  95

Thr Gln Phe His Leu Gly Leu Met Ser Lys Asn Gly Tyr Gly Val Pro
            100                 105                 110

Val Asp Pro Val Lys Ala Arg Glu Trp Phe Ala Lys Ala Ala Gly Gln
        115                 120                 125

Asn Tyr Gln Pro Ala Gln Tyr Gln Leu Ala Leu Met Gln Phe Ser Gly
    130                 135                 140

Thr Gly Gly Thr Glu Asn Lys Ser Ala Ala Ile Glu Gln Phe Lys Lys
145                 150                 155                 160

Leu Ala Ser Glu Gly Tyr Ala Pro Ala Gln Tyr Thr Leu Gly Tyr Leu
                165                 170                 175

Asn Leu Lys Gly Asp Gly Ile Pro Gln Asn Ser Gly Glu Ala Arg Phe
            180                 185                 190

Trp Phe Glu Lys Ala Ala Ala Lys Asn Asp Val Arg Ala Thr Ala Ala
        195                 200                 205

Leu Ala Trp Leu Tyr Leu Lys Gly Val Gly Ala Pro Ile Asp Glu Lys
    210                 215                 220

Lys Ala Ala Val Leu Phe Glu Lys Ala Ala Asn Met Gly Asp Ala Tyr
225                 230                 235                 240

Ser Gln Asp Gln Phe Gly Met Met Leu Gly Gln Gly Thr Gly Met Asn
                245                 250                 255

Ala Glu Pro Glu Lys Ala Phe Leu Trp Ile Glu Lys Ala Ala Asn Gln
            260                 265                 270

Gln Tyr Pro Val Ala Glu Tyr His Met Ala Met Met Tyr Leu Thr Gly
```

```
                275                 280                 285
Ser Gly Thr Glu Lys Asn Pro Glu Leu Ala Val Lys Trp Leu Glu Lys
    290                 295                 300

Ala Ala Phe His Gly Asn Val Asp Ala Gln Asn Phe Tyr Ala Ser Leu
305                 310                 315                 320

Leu Tyr Leu Gly Tyr Gly Ile Lys Gln Asp Ile Pro Arg Ala Ile Gly
                325                 330                 335

Tyr Phe Thr Glu Ala Ala Glu Gly Gly His Ala Glu Ser Gln Phe Leu
            340                 345                 350

Leu Gly Thr Ile Tyr Val Lys Gly Asn Gly Val Leu Thr Asn Leu Lys
        355                 360                 365

Thr Ala Arg Asn Trp Phe Glu Lys Ala Glu Lys Asn Gly His Pro Asp
    370                 375                 380

Ala Lys Ala Ala Leu Glu Lys Leu Asp Glu Met Glu Gly Lys Gly Arg
385                 390                 395                 400

Ala Thr Pro Glu Lys Thr Asp Thr Gly Asn His Tyr Pro Ser
                405                 410

<210> SEQ ID NO 67
<211> LENGTH: 630
<212> TYPE: DNA
<213> ORGANISM: Oxalobacter formigenes

<400> SEQUENCE: 67
atggagtgct tgagcctgaa aaaaacaggc tgttccctga tggcaatgac cctttgtttc    60
attttccttt cggcgtgcaa accaaaaacc attttggaca ccactccgct gaaagcggaa   120
atcgcgcagg aatttgccaa agccgataaa ggcgacgcgg ctgcccggtt caatatcggc   180
ctcatgtact caggggaga aggtgtccct caggattacc ggcaggcgcg cgtctggttt   240
gaaaaagcgg ccatgcaagg gctcggcgaa gcccaataca atatgggagc catgctggag   300
cagggactcg gcacagaaaa gaatgccgcc acagccagaa cctggtatga aaaagcggca   360
gcacagggca acgctcacgc ccagtacaac cttgccaggc tttacctgac aggcaaaggc   420
acgtcacaaa acatcggcaa ggcaggtgaa tggatgcaaa agcggcagc acagggaatg   480 acagaagcaa agaacgcttt tccattcta ttcgacagtc aatccggctc atttaaaccg   540
gcaaaaatcc agtcatggat tgaacaatcg gtccagaccg gtggggaaaa agcgaaaatc   600
ctgcaggaaa aataagaag ccatagctga                                    630

<210> SEQ ID NO 68
<211> LENGTH: 209
<212> TYPE: PRT
<213> ORGANISM: Oxalobacter formigenes

<400> SEQUENCE: 68

Met Glu Cys Leu Ser Leu Lys Lys Thr Gly Cys Ser Leu Met Ala Met
1               5                   10                  15

Thr Leu Cys Phe Ile Phe Leu Ser Ala Cys Lys Pro Lys Thr Ile Leu
            20                  25                  30

Asp Thr Thr Pro Leu Lys Ala Glu Ile Ala Gln Glu Phe Ala Lys Ala
        35                  40                  45

Asp Lys Gly Asp Ala Ala Ala Arg Phe Asn Ile Gly Leu Met Tyr Phe
    50                  55                  60

Arg Gly Glu Gly Val Pro Gln Asp Tyr Arg Gln Ala Arg Val Trp Phe
65                  70                  75                  80
```

```
Glu Lys Ala Ala Met Gln Gly Leu Gly Glu Ala Gln Tyr Asn Met Gly
            85                  90                  95

Ala Met Leu Glu Gln Gly Leu Gly Thr Glu Lys Asn Ala Ala Thr Ala
            100                 105                 110

Arg Thr Trp Tyr Glu Lys Ala Ala Ala Gln Gly Asn Ala His Ala Gln
            115                 120                 125

Tyr Asn Leu Ala Arg Leu Tyr Leu Thr Gly Lys Gly Thr Ser Gln Asn
            130                 135                 140

Ile Gly Lys Ala Gly Glu Trp Met Gln Lys Ala Ala Gln Gly Met
145                 150                 155                 160

Thr Glu Ala Lys Glu Arg Phe Ser Ile Leu Phe Asp Ser Gln Ser Gly
            165                 170                 175

Ser Phe Lys Pro Ala Lys Ile Gln Ser Trp Ile Glu Gln Ser Val Gln
            180                 185                 190

Thr Gly Gly Glu Lys Ala Lys Ile Leu Gln Glu Lys Ile Arg Ser His
            195                 200                 205

Ser

<210> SEQ ID NO 69
<211> LENGTH: 1461
<212> TYPE: DNA
<213> ORGANISM: Oxalobacter formigenes

<400> SEQUENCE: 69
atgaatgaat cgacgtcttt tcaaacagtg aaatcccatt tcatgaaaac cggctttatt      60
tcaatctgca acgggcgat tcccgtcctg ctcttctcat tcatggcttc cctgtcgaat     120
ccggcagcgg gacaaaccga cgccgatgcg aaaaccgaag gcatcaggct gtatcaggaa     180
aaaaaataca tcgaagccct tccctacctc aatgcgcccg atgcccaaaa agacccgctt     240
gtccagagcg cgctcggcaa tatgttttca atggggctgg gcgtcgacgt caatcaggaa     300
aaagccttcg actggtacct gaaagccgcc aaacagaata cgcgatggc ccagctctac     360
gtcgcctata tgcttgaaaa aggacttggc gtccgcaaaa cgacaggga agccttcaac     420
tggtacaaaa aagcagccga acagaacgta ccgaacgcac aatacaaact cggcactctt     480
tacgaaaaag gcatcggcac ccgaatcaat ctgaagaag ccctgaactg gtaccggaaa     540
gccgccgaag gaggcctgtc gggagcgcaa gtcaaactgg ccgcctgta cagcgaaggc     600
atcggcgtca acgcgactg taccgaagcc gcccgctggt tctaccctgc agccgaaaaa     660
ggggacgtca tggcacagac tgcccttgcc ttcctcttg aaaacgggct tggcgtccag     720
caggatgacg ccttcgctat cagctggtac tccaaagcgg ccgaaaaggg tttcgctcct     780
gcccagaaca atctgggtta cctgtacgac aacggcatcg gcgtcctgcg tgactacacc     840
accgccagaa aatggtacga agccgccgca aaacagggga atgtggaagc ccagttcaac     900
ctcggccagc tctacaccct ggccacggc accgttcagg actacggcaa ggccgccgaa     960
tggctcgaaa aagccgctgc caaaggccac ccgaaagccc tgaacaatct cggcatggcc    1020
agtcttgacg gcatgggcgt tccgatggat cgcgtcaagg ccggagaata cttccggaaa    1080
gccgccctgc tcggcaacgc ccatgcccag tacaatctgg ctaccctgta cgtccagcat    1140
ccagacgcac tgacaaaaga caagcgaagc aaaaccgacg ctttggcccct gcaatggttc    1200
aaaaaaagcg cggctgccgg tcaccctgcc gcgatggcct atctggctga cgtctatacc    1260
tacggcaaac tgggacagag accccaaccgg aaactggccg ccagctggaa acagaaagcc    1320
gatgccgccg aagaaaaacg caaaagagca cagaccatca ctccgctgcc cagaaccgaa    1380
```

-continued

```
gcggccagac cgccaaaac cgaaccggtc aagcccgtca caaaggattt caatcccaac    1440
gaccgcgact ggctggaata g                                            1461
```

<210> SEQ ID NO 70
<211> LENGTH: 486
<212> TYPE: PRT
<213> ORGANISM: Oxalobacter formigenes

<400> SEQUENCE: 70

```
Met Asn Glu Ser Thr Ser Phe Gln Thr Val Lys Ser His Phe Met Lys
1               5                   10                  15

Thr Gly Phe Ile Ser Ile Cys Lys Arg Ala Ile Pro Val Leu Leu Phe
            20                  25                  30

Ser Phe Met Ala Ser Leu Ser Asn Pro Ala Ala Gly Gln Thr Asp Ala
        35                  40                  45

Asp Ala Lys Thr Glu Gly Ile Arg Leu Tyr Gln Glu Lys Lys Tyr Ile
    50                  55                  60

Glu Ala Leu Pro Tyr Leu Asn Ala Pro Asp Ala Gln Lys Asp Pro Leu
65                  70                  75                  80

Val Gln Ser Ala Leu Gly Asn Met Phe Ser Met Gly Leu Gly Val Asp
                85                  90                  95

Val Asn Gln Glu Lys Ala Phe Asp Trp Tyr Leu Lys Ala Ala Lys Gln
            100                 105                 110

Asn Asn Ala Met Ala Gln Leu Tyr Val Ala Tyr Met Leu Glu Lys Gly
        115                 120                 125

Leu Gly Val Arg Lys Asn Asp Arg Glu Ala Phe Asn Trp Tyr Lys Lys
    130                 135                 140

Ala Ala Glu Gln Asn Val Pro Asn Ala Gln Tyr Lys Leu Gly Thr Leu
145                 150                 155                 160

Tyr Glu Lys Gly Ile Gly Thr Arg Ile Asn Leu Lys Glu Ala Leu Asn
                165                 170                 175

Trp Tyr Arg Lys Ala Ala Glu Gly Gly Leu Ser Gly Ala Gln Val Lys
            180                 185                 190

Leu Gly Arg Leu Tyr Ser Glu Gly Ile Gly Val Lys Arg Asp Tyr Thr
        195                 200                 205

Glu Ala Ala Arg Trp Phe Tyr Pro Ala Ala Glu Lys Gly Asp Val Met
    210                 215                 220

Ala Gln Thr Ala Leu Ala Phe Leu Phe Glu Asn Gly Leu Gly Val Gln
225                 230                 235                 240

Gln Asp Asp Ala Phe Ala Ile Ser Trp Tyr Ser Lys Ala Ala Glu Lys
                245                 250                 255

Gly Phe Ala Pro Ala Gln Asn Asn Leu Gly Tyr Leu Tyr Asp Asn Gly
            260                 265                 270

Ile Gly Val Leu Arg Asp Tyr Thr Thr Ala Arg Lys Trp Tyr Glu Ala
        275                 280                 285

Ala Ala Lys Gln Gly Asn Val Glu Ala Gln Phe Asn Leu Gly Gln Leu
    290                 295                 300

Tyr Thr Leu Gly His Gly Thr Val Gln Asp Tyr Gly Lys Ala Ala Glu
305                 310                 315                 320

Trp Leu Glu Lys Ala Ala Ala Lys Gly His Pro Lys Ala Leu Asn Asn
                325                 330                 335

Leu Gly Met Ala Ser Leu Asp Gly Met Gly Val Pro Met Asp Arg Val
            340                 345                 350
```

```
Lys Ala Gly Glu Tyr Phe Arg Lys Ala Ala Leu Leu Gly Asn Ala His
                355                 360                 365

Ala Gln Tyr Asn Leu Ala Thr Leu Tyr Val Gln His Pro Asp Ala Leu
            370                 375                 380

Thr Lys Asp Lys Arg Ser Lys Thr Asp Ala Leu Ala Leu Gln Trp Phe
385                 390                 395                 400

Lys Lys Ser Ala Ala Gly His Pro Ala Ala Met Ala Tyr Leu Ala
                405                 410                 415

Asp Val Tyr Thr Tyr Gly Lys Leu Gly Gln Arg Pro Asn Arg Lys Leu
            420                 425                 430

Ala Ala Ser Trp Lys Gln Lys Ala Asp Ala Ala Glu Glu Lys Arg Lys
                435                 440                 445

Arg Ala Gln Thr Ile Thr Pro Leu Pro Arg Thr Glu Ala Ala Arg Pro
    450                 455                 460

Ala Lys Thr Glu Pro Val Lys Pro Val Thr Lys Asp Phe Asn Pro Asn
465                 470                 475                 480

Asp Arg Asp Trp Leu Glu
                485

<210> SEQ ID NO 71
<211> LENGTH: 885
<212> TYPE: DNA
<213> ORGANISM: Oxalobacter formigenes

<400> SEQUENCE: 71
atgatcaatc gttcttttcaa gaatgcaaaa attatatttta tcctttttct tttatcattt      60
tgtataaatg tgtttgccgg tgatatagaa aaaggattaa agctgttcaa aaaacaggaa     120
tatgaaaagg cattgcctta ttttcagaaa ccggttgcgc aaaaaaatcc ggacgttcag     180
gctgcattgg gatacatgta tcgtgaaggt ttagccgttc gaaagacat tcaaaaggca     240 tttgatttat ttctggagtc agccagacaa acaatccga gaggacagta tggaatggga     300
accatgtatg accttggact gattgtcaaa caggataaag aaaaagcgtt caaatggtat     360
atgtatgcag ctgaaaatgg atacaagaat gcccaatata atattgggat tatgtatgcc     420
agaggaagag gaacaaaacg ggattacaaa aaagccaggg aatggtatga aaaagccgtt     480
ttgcagggac acaagggtgc tatgacgaat ttgggacttc tttattatcg gggatggggc     540
ggcccgaaag attatgctaa tcagcagaa ctgaatacac gggcggctaa attaggtgat     600
gatatagccc aatataatct ggcacgtgat tatgaaaatg gtaccggcgt tccaaaagat     660
tacaagcagg ctgtttactg gtatttcaag ggggctgaaa atggaaatgc aatggcgatg     720
gaacgattgt atgaagccta tcacctcaac cgattgggtt tgccgagaga cgatgaaaaa     780
gcgcattact gggctgaaaa agcccgggaa acccgccgta aaacaggaga actggctccc     840
gagtcaatga gcattatcga aaaaatagag cgaatctggt tctga                    885

<210> SEQ ID NO 72
<211> LENGTH: 294
<212> TYPE: PRT
<213> ORGANISM: Oxalobacter formigenes

<400> SEQUENCE: 72

Met Ile Asn Arg Ser Phe Lys Asn Ala Lys Ile Ile Phe Ile Leu Phe
1               5                   10                  15

Leu Leu Ser Phe Cys Ile Asn Val Phe Ala Gly Asp Ile Glu Lys Gly
            20                  25                  30
```

```
Leu Lys Leu Phe Lys Lys Gln Glu Tyr Glu Lys Ala Leu Pro Tyr Phe
         35                  40                  45
Gln Lys Pro Val Ala Gln Lys Asn Pro Asp Val Gln Ala Ala Leu Gly
 50                  55                  60
Tyr Met Tyr Arg Glu Gly Leu Ala Val Pro Lys Asp Ile Gln Lys Ala
 65                  70                  75                  80
Phe Asp Leu Phe Leu Glu Ser Ala Arg Gln Asn Asn Pro Arg Gly Gln
                 85                  90                  95
Tyr Gly Met Gly Thr Met Tyr Asp Leu Gly Leu Ile Val Lys Gln Asp
                100                 105                 110
Lys Glu Lys Ala Phe Lys Trp Tyr Met Tyr Ala Ala Glu Asn Gly Tyr
                115                 120                 125
Lys Asn Ala Gln Tyr Asn Ile Gly Ile Met Tyr Ala Arg Gly Arg Gly
            130                 135                 140
Thr Lys Arg Asp Tyr Lys Lys Ala Arg Glu Trp Tyr Glu Lys Ala Val
145                 150                 155                 160
Leu Gln Gly His Lys Gly Ala Met Thr Asn Leu Gly Leu Leu Tyr Tyr
                165                 170                 175
Arg Gly Trp Gly Gly Pro Lys Asp Tyr Ala Lys Ser Ala Glu Leu Asn
            180                 185                 190
Thr Arg Ala Ala Lys Leu Gly Asp Asp Ile Ala Gln Tyr Asn Leu Ala
        195                 200                 205
Arg Asp Tyr Glu Asn Gly Thr Gly Val Pro Lys Asp Tyr Lys Gln Ala
    210                 215                 220
Val Tyr Trp Tyr Phe Lys Gly Ala Glu Asn Gly Asn Ala Met Ala Met
225                 230                 235                 240
Glu Arg Leu Tyr Glu Ala Tyr His Leu Asn Arg Leu Gly Leu Pro Arg
                245                 250                 255
Asp Asp Glu Lys Ala His Tyr Trp Ala Glu Lys Ala Arg Glu Thr Arg
                260                 265                 270
Arg Lys Thr Gly Glu Leu Ala Pro Glu Ser Met Ser Ile Ile Glu Lys
            275                 280                 285
Ile Glu Arg Ile Trp Phe
    290

<210> SEQ ID NO 73
<211> LENGTH: 888
<212> TYPE: DNA
<213> ORGANISM: Oxalobacter formigenes

<400> SEQUENCE: 73
atggttgatt ttttatttaa aaatatcaga attatattta tcctctcttt ggtttcattc      60
agcctgaacc ttgaagccgc cgataccata aaccaaggac tggatttatt tcaaaaaaaa     120
caattcgaaa aagcgttacc ctatctggaa gcatcacatt ccaaaaacga tcctcgagta     180
caagcggcat taggatatat gtatcgggat gggctgggag tcgaaaaaga ttatcagaaa     240
gcgtttatgt tatttctgga gtctgccaaa caatccaatc ccaagggaca gttcggcgta     300
ggaagtatgt atgatcgtgg atttttttgtt aaacgtaata aggaaaaagc gtttaaatgg     360
tatctatacg cagctgagaa tggttatagt tctgctcaaa ataatgtagc ctggtcttat     420
gtacatggag agggaattcc taaagattac aaaaaagcca gagaatggta tgaaaaagca     480
atgattcaag acattcgaa tgccatggtt ggtttatcct ttatgtatta ttggggaaaa     540
ggcgtaaaaa aagatcgtaa taaagcagcg gaactggaca aacgggcggc agcgttggga     600
```

```
aacagaaaag gacagttcaa tctgggccgg gattacgaag atggaacagg tgttcccaaa    660
gactacaagc aagccgttta ctggtacttt aaagccgctg aaaacggtga tcccatggct    720
atggaacgtc tttatgaagc ctatcacctc aaccgattgg gtctgaagag agacgatgaa    780
aaagcccatt actgggctga aaagcccgg gaaacccgtc gaaaaacggg agaagtcgat    840
ccgcgttcat tgtctgtcat tgaaaaagtc agaatgatct ggttctga                888
```

<210> SEQ ID NO 74
<211> LENGTH: 295
<212> TYPE: PRT
<213> ORGANISM: Oxalobacter formigenes

<400> SEQUENCE: 74

```
Met Val Asp Phe Leu Phe Lys Asn Ile Arg Ile Ile Phe Ile Leu Ser
1               5                   10                  15

Leu Val Ser Phe Ser Leu Asn Leu Glu Ala Ala Asp Thr Ile Asn Gln
            20                  25                  30

Gly Leu Asp Leu Phe Gln Lys Lys Gln Phe Glu Lys Ala Leu Pro Tyr
        35                  40                  45

Leu Glu Ala Ser His Ser Lys Asn Asp Pro Arg Val Gln Ala Ala Leu
    50                  55                  60

Gly Tyr Met Tyr Arg Asp Gly Leu Gly Val Glu Lys Asp Tyr Gln Lys
65                  70                  75                  80

Ala Phe Met Leu Phe Leu Glu Ser Ala Lys Gln Ser Asn Pro Lys Gly
                85                  90                  95

Gln Phe Gly Val Gly Ser Met Tyr Asp Arg Gly Phe Phe Val Lys Arg
            100                 105                 110

Asn Lys Glu Lys Ala Phe Lys Trp Tyr Leu Tyr Ala Ala Glu Asn Gly
        115                 120                 125

Tyr Ser Ser Ala Gln Asn Asn Val Ala Trp Ser Tyr Val His Gly Glu
    130                 135                 140

Gly Ile Pro Lys Asp Tyr Lys Lys Ala Arg Glu Trp Tyr Glu Lys Ala
145                 150                 155                 160

Met Ile Gln Gly His Ser Asn Ala Met Val Gly Leu Ser Phe Met Tyr
                165                 170                 175

Tyr Trp Gly Lys Gly Val Lys Lys Asp Arg Asn Lys Ala Ala Glu Leu
            180                 185                 190

Asp Lys Arg Ala Ala Ala Leu Gly Asn Arg Lys Gly Gln Phe Asn Leu
        195                 200                 205

Gly Arg Asp Tyr Glu Asp Gly Thr Gly Val Pro Lys Asp Tyr Lys Gln
    210                 215                 220

Ala Val Tyr Trp Tyr Phe Lys Ala Ala Glu Asn Gly Asp Pro Met Ala
225                 230                 235                 240

Met Glu Arg Leu Tyr Glu Ala Tyr His Leu Asn Arg Leu Gly Leu Lys
                245                 250                 255

Arg Asp Asp Glu Lys Ala His Tyr Trp Ala Leu Lys Ala Arg Glu Thr
            260                 265                 270

Arg Arg Lys Thr Gly Glu Val Asp Pro Arg Ser Leu Ser Val Ile Glu
        275                 280                 285

Lys Val Arg Met Ile Trp Phe
    290                 295
```

<210> SEQ ID NO 75
<211> LENGTH: 954
<212> TYPE: DNA

<213> ORGANISM: Oxalobacter formigenes

<400> SEQUENCE: 75

```
atggaaagcc ataaagaaat caagtcaatt ttaaaagaac ttagccagat gaaaaaacaa    60
tctttatttc tcatcataat tgcaatgatt ctgacaatat ccgcttgtac agaaaaagag   120
tataaatacc tcgcagatga aaagcagga atcgaatact atcaaaacgg atcatatgat   180
aaagcgttgg catcactaaa aaaacatat ggttccggaa gtatggaagc cgcttattat   240
cttggcgaaa tgtatcgtca gggtaatggg gttgaaaaag atagaatcgt ttcttgcaat   300
tactatcaaa aatcagcaga aggggaaac aggaaagcct ttttgagagc aggaacctgt   360
catataccgg ataccagaga tggagaagga ttcaaagaaa cattcaaatg gtttaaaaaa   420
gcgtctgaag aattaaaaga aaccgatttg aatgaagcag aaaaaaaaga catgtatatc   480
aggcttggaa ttatgtatta cgctggaaaa ggtacactac aggattggag tgaagccgcg   540
aagtggtttg aaaaagctgc cgaaatgggg gatgcctact cacagggagg tctggcgtta   600
ttatattatt ccggcgatgg tgttttaact gacaggaaaa aagcgcgtta ttgggcagaa   660
aaagcagcgg cacaaggtaa tagtacagga gaaggtattc ttggaatgtt ataccaatat   720
agtcttccgc cggataaaga tatgagaaaa gctgtctatt ggtacaagaa atcagccgat   780
cagggaaatc caatatccca gtatcaattg gctgttatct atgaaaatgg tgatggtgtt   840
ccaaaaaacc tcgaaaaagc gcgctattac tatgaacagg catcgaaaag caaatatgat   900
ctgacaaaaa acagtttaaa ggaatttgaa tcgcgaaaca aagtttgca gtga    954
```

<210> SEQ ID NO 76
<211> LENGTH: 317
<212> TYPE: PRT
<213> ORGANISM: Oxalobacter formigenes

<400> SEQUENCE: 76

```
Met Glu Ser His Lys Glu Ile Lys Ser Ile Leu Lys Glu Leu Ser Gln
1               5                  10                  15

Met Lys Lys Gln Ser Leu Phe Leu Ile Ile Ile Ala Met Ile Leu Thr
            20                  25                  30

Ile Ser Ala Cys Thr Glu Lys Glu Tyr Lys Tyr Leu Ala Asp Glu Lys
        35                  40                  45

Ala Gly Ile Glu Tyr Tyr Gln Asn Gly Ser Tyr Asp Lys Ala Leu Ala
    50                  55                  60

Ser Leu Lys Lys Thr Tyr Gly Ser Gly Ser Met Glu Ala Ala Tyr Tyr
65                  70                  75                  80

Leu Gly Glu Met Tyr Arg Gln Gly Asn Gly Val Glu Lys Asp Arg Ile
                85                  90                  95

Val Ser Cys Asn Tyr Tyr Gln Lys Ser Ala Glu Gly Gly Asn Arg Lys
            100                 105                 110

Ala Phe Leu Arg Ala Gly Thr Cys His Ile Pro Asp Thr Arg Asp Gly
        115                 120                 125

Glu Gly Phe Lys Glu Thr Phe Lys Trp Phe Lys Lys Ala Ser Glu Glu
    130                 135                 140

Leu Lys Glu Thr Asp Leu Asn Glu Ala Glu Lys Lys Asp Met Tyr Ile
145                 150                 155                 160

Arg Leu Gly Ile Met Tyr Tyr Ala Gly Lys Gly Thr Leu Gln Asp Trp
                165                 170                 175

Ser Glu Ala Ala Lys Trp Phe Glu Lys Ala Ala Glu Met Gly Asp Ala
            180                 185                 190
```

```
Tyr Ser Gln Gly Gly Leu Ala Leu Leu Tyr Tyr Ser Gly Asp Gly Val
        195                 200                 205

Leu Thr Asp Arg Lys Lys Ala Arg Tyr Trp Ala Glu Lys Ala Ala Ala
    210                 215                 220

Gln Gly Asn Ser Thr Gly Glu Gly Ile Leu Gly Met Leu Tyr Gln Tyr
225                 230                 235                 240

Ser Leu Pro Pro Asp Lys Asp Met Arg Lys Ala Val Tyr Trp Tyr Lys
            245                 250                 255

Lys Ser Ala Asp Gln Gly Asn Pro Ile Ser Gln Tyr Gln Leu Ala Val
        260                 265                 270

Ile Tyr Glu Asn Gly Asp Gly Val Pro Lys Asn Leu Glu Lys Ala Arg
        275                 280                 285

Tyr Tyr Tyr Glu Gln Ala Ser Lys Ser Lys Tyr Asp Leu Thr Lys Asn
    290                 295                 300

Ser Leu Lys Glu Phe Glu Ser Arg Asn Lys Ser Leu Gln
305                 310                 315

<210> SEQ ID NO 77
<211> LENGTH: 1083
<212> TYPE: DNA
<213> ORGANISM: Oxalobacter formigenes

<400> SEQUENCE: 77
atgctgaaaa aatcattatc tctttcgatt atccttttc tcttgttttc cttatcgggc      60
tgtgagaaga acggtgagga aaacaagagc aaggggatg tttttttattc cagagggat    120 tatgaaaatg ccctgtctgt ttacaaacag gaggcaaaac ggggcgattc gcatgccttg   180
ctcggtttgt gcaagatgta tgaggatgga aaggggtca aggaaaacga tcggctggct   240
ttccagtatt gcatgcaggc ggccaaacgg ggtgaggtga aggcacagaa gcgtctgggg   300
atgatgtatt acaagggtac cggggtggcg aggaatgtgc atgaagcgcg tttctggttc   360
aatcaggcgg ccttgtcgga cgatccggag gcgctttatt atctcgggat cgcttatttg   420
aaagggatcg gcggggagaa agactttcat caggcgcatg accttttga aagggcggcc    480 gatgagggac atgtgaatgc catgtggaag ctgtatgaga tgttcaatga aggaaccggt   540
gtcaggcagg acaggcagga ggcgttcaaa tggctgatga gctggcggc cgatggcgac   600 atacgcgcgc agttccttgc cggttcgtcg tatctgaccg gcaatggggt gaaggctgat   660
cctgccgagg cggtcaggtg gtttgaaaag gcggcgcagc agggcagtgt tgatgcccag   720
acttcactgg ttttatatta tctgggcaac gagccagtcc gtctggatga agcgcgaagc   780
tgggcggcga aactggaaaa ccagacgggt tcgcgcggtg tcggggcggt gttcaggcgt   840 ttttcactg agatgggaga gtggcctgag ccggaacgca cgcatgaacg gataaaagac   900
tggttcgatt ctcttttttc gacgaaagac ccggatctgc tttatggtct cggcttttg    960 tacgagctgg gttatcaggg gcagcgcgat atggacaagg cgctcgccct ctataaaagg  1020
gcggcggctc tggggaacgt gaatgcgatt aaaaaactga agaactcca gtccgttttt   1080 taa                                                                1083

<210> SEQ ID NO 78
<211> LENGTH: 360
<212> TYPE: PRT
<213> ORGANISM: Oxalobacter formigenes

<400> SEQUENCE: 78
```

```
Met Leu Lys Lys Ser Leu Ser Leu Ser Ile Leu Phe Leu Phe
1               5                   10                  15

Ser Leu Ser Gly Cys Glu Lys Asn Gly Glu Asn Lys Ser Lys Gly
            20                  25                  30

Asp Val Phe Tyr Ser Arg Gly Asp Tyr Glu Asn Ala Leu Ser Val Tyr
            35                  40                  45

Lys Gln Glu Ala Lys Arg Gly Asp Ser His Ala Leu Leu Gly Leu Cys
        50                  55                  60

Lys Met Tyr Glu Asp Gly Lys Gly Val Lys Glu Asn Asp Arg Leu Ala
65                  70                  75                  80

Phe Gln Tyr Cys Met Gln Ala Ala Lys Arg Gly Glu Val Lys Ala Gln
                85                  90                  95

Lys Arg Leu Gly Met Met Tyr Tyr Lys Gly Thr Gly Val Ala Arg Asn
            100                 105                 110

Val His Glu Ala Arg Phe Trp Phe Asn Gln Ala Ala Leu Ser Asp Asp
            115                 120                 125

Pro Glu Ala Leu Tyr Tyr Leu Gly Ile Ala Tyr Leu Lys Gly Ile Gly
        130                 135                 140

Gly Glu Lys Asp Phe His Gln Ala His Asp Leu Phe Glu Arg Ala Ala
145                 150                 155                 160

Asp Glu Gly His Val Asn Ala Met Trp Lys Leu Tyr Glu Met Phe Asn
                165                 170                 175

Glu Gly Thr Gly Val Arg Gln Asp Arg Gln Ala Phe Lys Trp Leu
            180                 185                 190

Met Lys Leu Ala Ala Asp Gly Asp Ile Arg Ala Gln Phe Leu Ala Gly
        195                 200                 205

Ser Ser Tyr Leu Thr Gly Asn Gly Val Lys Ala Asp Pro Ala Glu Ala
        210                 215                 220

Val Arg Trp Phe Glu Lys Ala Ala Gln Gln Gly Ser Val Asp Ala Gln
225                 230                 235                 240

Thr Ser Leu Val Leu Tyr Tyr Leu Gly Asn Glu Pro Val Arg Leu Asp
                245                 250                 255

Glu Ala Arg Ser Trp Ala Ala Lys Leu Glu Asn Gln Thr Gly Ser Arg
            260                 265                 270

Gly Val Gly Ala Val Phe Arg Arg Phe Phe Thr Glu Met Gly Glu Trp
        275                 280                 285

Pro Glu Pro Glu Arg Thr His Glu Arg Ile Lys Asp Trp Phe Asp Ser
        290                 295                 300

Leu Phe Ser Thr Lys Asp Pro Asp Leu Leu Tyr Gly Leu Gly Phe Leu
305                 310                 315                 320

Tyr Glu Leu Gly Tyr Gln Gly Gln Arg Asp Met Asp Lys Ala Leu Ala
                325                 330                 335

Leu Tyr Lys Arg Ala Ala Ala Leu Gly Asn Val Asn Ala Ile Lys Lys
            340                 345                 350

Leu Lys Glu Leu Gln Ser Val Phe
            355                 360

<210> SEQ ID NO 79
<211> LENGTH: 876
<212> TYPE: DNA
<213> ORGANISM: Oxalobacter formigenes

<400> SEQUENCE: 79
atgaaacgat tttgtaaagc acttttcctc tcactcctga tgcttgtagg tatacatgct    60
```

```
ctggctgata acgttactga aggtaaccgg ctttatagggg caaaacaata tgaagaggcg    120
atgagctttt tcatgaagct ggatgcgcag aaaagtccgg aaatcatgaa tcgtatcggt    180
ttcatgtatg acgctggtcg ggggggtggaa agaaacggga atattgcttt tcaatggtat    240
cgcaaggcag ctgaaacagg attggcaaaa gctcaataca atctgggatt atgctttcaa    300
aatggaattg gtgttaaaaa agatatcaac gaagccataa atggtatctc aaggccgca    360 gaacagggat atcccgatgc ggaatccaaa atgggttatc tgaccgtaac cgggaaaggc    420
gtcaaacagg atttcaaaca ggccatgcaa tggtaccggc gtgctgtaga gcatggcaac    480
atacatgcca tcccggagct cggtatcatg tatgaggaag tcttggcgt caaaaaggac    540 aagacccatg ctgtccagta ttacattatg ggggcggaaa aaggaaacgt ccgggcacag    600
tttttgctgg cggaagccta ccgttacggc cgggcatca aaaacgacga tgagcgttcg    660
ctctactggt acaagaaggc ggcggaaaac ggcagtgccg atgcctacga tgcgttaggc    720
agcgtgtatg ccaacgaaca gctggggcag aaaaaggaca ggaaaaaagc cggggaaatg    780
gtggaaaaag ccattgaaat ccgcaagcag aatggagagg gcgatcccga tgccagacgc    840
cgcctgaagt ttttcggggt gaagctggat gattag                              876

<210> SEQ ID NO 80
<211> LENGTH: 291
<212> TYPE: PRT
<213> ORGANISM: Oxalobacter formigenes

<400> SEQUENCE: 80

Met Lys Arg Phe Cys Lys Ala Leu Phe Leu Ser Leu Leu Met Leu Val
1               5                   10                  15

Gly Ile His Ala Leu Ala Asp Asn Val Thr Glu Gly Asn Arg Leu Tyr
            20                  25                  30

Arg Ala Lys Gln Tyr Glu Glu Ala Met Ser Phe Phe Met Lys Leu Asp
        35                  40                  45

Ala Gln Lys Ser Pro Glu Ile Met Asn Arg Ile Gly Phe Met Tyr Asp
    50                  55                  60

Ala Gly Arg Gly Val Glu Arg Asn Gly Asn Ile Ala Phe Gln Trp Tyr
65                  70                  75                  80

Arg Lys Ala Ala Glu Thr Gly Leu Ala Lys Ala Gln Tyr Asn Leu Gly
                85                  90                  95

Leu Cys Phe Gln Asn Gly Ile Gly Val Lys Lys Asp Ile Asn Glu Ala
            100                 105                 110

Ile Lys Trp Tyr Leu Lys Ala Ala Glu Gln Gly Tyr Pro Asp Ala Glu
        115                 120                 125

Ser Lys Met Gly Tyr Leu Thr Val Thr Gly Lys Gly Val Lys Gln Asp
    130                 135                 140

Phe Lys Gln Ala Met Gln Trp Tyr Arg Arg Ala Val Glu His Gly Asn
145                 150                 155                 160

Ile His Ala Ile Pro Glu Leu Gly Ile Met Tyr Glu Glu Gly Leu Gly
                165                 170                 175

Val Lys Lys Asp Lys Thr His Ala Val Gln Tyr Tyr Ile Met Gly Ala
            180                 185                 190

Glu Lys Gly Asn Val Arg Ala Gln Phe Leu Leu Ala Glu Ala Tyr Arg
        195                 200                 205

Tyr Gly Arg Gly Ile Lys Asn Asp Asp Glu Arg Ser Leu Tyr Trp Tyr
    210                 215                 220

Lys Lys Ala Ala Glu Asn Gly Ser Ala Asp Ala Tyr Asp Ala Leu Gly
```

```
                225                 230                 235                 240
Ser Val Tyr Ala Asn Glu Gln Leu Gly Gln Lys Lys Asp Arg Lys Lys
                    245                 250                 255

Ala Gly Glu Met Val Glu Lys Ala Ile Glu Ile Arg Lys Gln Asn Gly
                260                 265                 270

Glu Gly Asp Pro Asp Ala Arg Arg Leu Lys Phe Phe Gly Val Lys
            275                 280                 285

Leu Asp Asp
    290

<210> SEQ ID NO 81
<211> LENGTH: 852
<212> TYPE: DNA
<213> ORGANISM: Oxalobacter formigenes

<400> SEQUENCE: 81
atgtgtaaaa actattcaat tgattacaga atatatttc gcgttttaat tcttttttta      60
ttggcttgtt ttcttttaac gcctgcatac gccaatgaca ttactcaggg attgaaatac    120
tataaaaaag aagaatatca aaaagcatat cgttattttt ccacaccggc tgctcaaaag    180
aatccccggg ttcaacgtat attgggatat atgtatttaa agggtcttgc cgtcaagcag    240
gattatcaaa aggcgatgtt ctggtatggc aaatcagctg atcagggtaa tcctcaagcc    300
atgtacgata ttggcgttat gtacgatttt ggacagggtg tgaaacagga tcatgaaaaa    360
gcgattcaat ggtatcagcg ctccgcttta aaggatatg ctgacgcaca atataacctt    420
ggtatcgctt atgaaaaggg agaaggtact cagcaaaatt acgctaaagc gcgtgaatgg    480
tatcaaaaag cagtcacaca gggtaatgtc agtgctatgg tcaatttagg caatctttat    540
ggggaaggtc tcggcggtga aaaaaacgac tcaaaagcct tgatctttta caaaaaagct    600
gccgaaaaag gtgattcggc cgcccaatat aatctcgccg aatactaccg tgccggctta    660 gctacccac gagacctcga caaagccatc tactggtacg aaaagagcgc tgcagagggc    720
accatcaagg caatggacaa actggccaga atctatcggg tcggctacaa acacatccct    780
gccaatcagg ccttgtccga tgaatgggcc gacaaggctg caaaggcacg tgcaagggaa    840
gccgtcaggt aa                                                        852

<210> SEQ ID NO 82
<211> LENGTH: 283
<212> TYPE: PRT
<213> ORGANISM: Oxalobacter formigenes

<400> SEQUENCE: 82

Met Cys Lys Asn Tyr Ser Ile Asp Tyr Arg Ile Tyr Phe Arg Val Leu
1               5                   10                  15

Ile Leu Phe Leu Leu Ala Cys Phe Leu Leu Thr Pro Ala Tyr Ala Asn
            20                  25                  30

Asp Ile Thr Gln Gly Leu Lys Tyr Tyr Lys Glu Glu Tyr Gln Lys
        35                  40                  45

Ala Tyr Arg Tyr Phe Ser Thr Pro Ala Ala Gln Lys Asn Pro Arg Val
    50                  55                  60

Gln Arg Ile Leu Gly Tyr Met Tyr Leu Lys Gly Leu Ala Val Lys Gln
65                  70                  75                  80

Asp Tyr Gln Lys Ala Met Phe Trp Tyr Gly Lys Ser Ala Asp Gln Gly
                85                  90                  95

Asn Pro Gln Ala Met Tyr Asp Ile Gly Val Met Tyr Asp Phe Gly Gln
```

```
                    100                 105                 110
Gly Val Lys Gln Asp His Glu Lys Ala Ile Gln Trp Tyr Gln Arg Ser
            115                 120                 125
Ala Leu Lys Gly Tyr Ala Asp Ala Gln Tyr Asn Leu Gly Ile Ala Tyr
        130                 135                 140
Glu Lys Gly Glu Gly Thr Gln Gln Asn Tyr Ala Lys Ala Arg Glu Trp
145                 150                 155                 160
Tyr Gln Lys Ala Val Thr Gln Gly Asn Val Ser Ala Met Val Asn Leu
                165                 170                 175
Gly Asn Leu Tyr Gly Glu Gly Leu Gly Gly Glu Lys Asn Asp Ser Lys
            180                 185                 190
Ala Phe Asp Leu Tyr Lys Lys Ala Ala Glu Lys Gly Asp Ser Ala Ala
        195                 200                 205
Gln Tyr Asn Leu Ala Glu Tyr Tyr Arg Ala Gly Leu Ala Thr Pro Arg
        210                 215                 220
Asp Leu Asp Lys Ala Ile Tyr Trp Tyr Glu Lys Ser Ala Ala Glu Gly
225                 230                 235                 240
Thr Ile Lys Ala Met Asp Lys Leu Ala Arg Ile Tyr Arg Val Gly Tyr
                245                 250                 255
Lys His Ile Pro Ala Asn Gln Ala Leu Ser Asp Glu Trp Ala Asp Lys
            260                 265                 270
Ala Ala Lys Ala Arg Ala Arg Glu Ala Val Arg
        275                 280

<210> SEQ ID NO 83
<211> LENGTH: 909
<212> TYPE: DNA
<213> ORGANISM: Oxalobacter formigenes

<400> SEQUENCE: 83
atgaaacagc cttatccata tttgttcttc aaaatgaaat ttctttcaaa aatattcttt      60
ttttattttt ttttaggtat aagcagcagt gttttttgcag ataatgcaaa acagggatg    120 agtttgttcg agtcagcgaa atatgagcaa gcgatgactt atttcctgaa accggatgct    180
cagagaaatg cagaagtact taatcatatt ggttatatgt atgacaatgg attaggtgtt    240
aggcaaaatc caaaactggc taatcaatgg tatagaaaag catcagaaaa aggatttcct    300
gctgctgatt tcaatattgg attaagtttt gaatcaggat ctggtgttaa aaaagatatc    360
aacgaagcca taaatggta tctcaaggct gcagaacagg atatcccga tgcagaatcc     420 aaaatgggtt atctgaccgt aaccggaaaa ggcgtcaaac aggatttcaa acaggccatg    480
caatggtacc ggcgtgccgt tgaacatggc agtgttcatg ccatttcaga gctcggtatc    540
ctgtatgagg aaggtcttgg cgtcaaaaag gacaagaccc atgccgtcca gtattacatc    600
atgggtgccg aaaagggaaa cgtcagggca cagttcctgt ggcggaagc ctaccgttac     660 ggcctgggca tcaaaaacga cgatgagcgt tcgctctact ggtacaacaa ggcagcggaa    720
aacgggagtg ccgatgccta cgatgcgtta ggcagcgtgt atgccaacga acagctgggc    780
cagaaaaaag acaggaaaaa agcaggcgaa atggtggaaa agccattga aatccgcaag     840 cagaatggag agggcgatcc cgatgccaga cgccgcctga ggttttcgg ggtgaagctg     900 gatgactga                                                            909

<210> SEQ ID NO 84
<211> LENGTH: 302
<212> TYPE: PRT
```

<213> ORGANISM: Oxalobacter formigenes

<400> SEQUENCE: 84

```
Met Lys Gln Pro Tyr Pro Tyr Leu Phe Phe Lys Met Lys Phe Leu Ser
1               5                   10                  15
Lys Ile Phe Phe Phe Tyr Phe Phe Leu Gly Ile Ser Ser Ser Val Phe
                20                  25                  30
Ala Asp Asn Ala Lys Thr Gly Met Ser Leu Phe Glu Ser Ala Lys Tyr
            35                  40                  45
Glu Gln Ala Met Thr Tyr Phe Leu Lys Pro Asp Ala Gln Arg Asn Ala
        50                  55                  60
Glu Val Leu Asn His Ile Gly Tyr Met Tyr Asp Asn Gly Leu Gly Val
65                  70                  75                  80
Arg Gln Asn Pro Lys Leu Ala Asn Gln Trp Tyr Arg Lys Ala Ser Glu
                85                  90                  95
Lys Gly Phe Pro Ala Ala Asp Phe Asn Ile Gly Leu Ser Phe Glu Ser
            100                 105                 110
Gly Ser Gly Val Lys Lys Asp Ile Asn Glu Ala Ile Lys Trp Tyr Leu
        115                 120                 125
Lys Ala Ala Glu Gln Gly Tyr Pro Asp Ala Glu Ser Lys Met Gly Tyr
    130                 135                 140
Leu Thr Val Thr Gly Lys Gly Val Lys Gln Asp Phe Lys Gln Ala Met
145                 150                 155                 160
Gln Trp Tyr Arg Arg Ala Val Glu His Gly Ser Val His Ala Ile Ser
                165                 170                 175
Glu Leu Gly Ile Leu Tyr Glu Gly Leu Gly Val Lys Lys Asp Lys
            180                 185                 190
Thr His Ala Val Gln Tyr Tyr Ile Met Gly Ala Glu Lys Gly Asn Val
        195                 200                 205
Arg Ala Gln Phe Leu Leu Ala Glu Ala Tyr Arg Tyr Gly Leu Gly Ile
    210                 215                 220
Lys Asn Asp Asp Glu Arg Ser Leu Tyr Trp Tyr Asn Lys Ala Ala Glu
225                 230                 235                 240
Asn Gly Ser Ala Asp Ala Tyr Asp Ala Leu Gly Ser Val Tyr Ala Asn
                245                 250                 255
Glu Gln Leu Gly Gln Lys Lys Asp Arg Lys Lys Ala Gly Glu Met Val
            260                 265                 270
Glu Lys Ala Ile Glu Ile Arg Lys Gln Asn Gly Glu Gly Asp Pro Asp
        275                 280                 285
Ala Arg Arg Arg Leu Arg Phe Phe Gly Val Lys Leu Asp Asp
    290                 295                 300
```

<210> SEQ ID NO 85
<211> LENGTH: 789
<212> TYPE: DNA
<213> ORGANISM: Oxalobacter formigenes

<400> SEQUENCE: 85

| | | | | | |
|---|---|---|---|---|---|
| atgcggctgt | ttgaagctgg | aaaataccag | caggccatga | cgtatttcat | gaaggaggat | 60 |
| gcccagaaga | atccggccgt | gatcaatcgt | attggctata | tgtatgatta | cgggctcggc | 120 |
| gttgaaaaaa | acaggcaaat | cagttttcag | tggtataaaa | aagcaggaga | aatgggggag | 180 |
| gccgctgcgc | agtttaatgt | cggactattc | tatgagaaag | gttatggcgt | tcctcaagat | 240 |
| ataaatatgg | ctatcgaatg | gtttcgtaaa | tctgcaaaac | aacaatatcc | gaatgctgaa | 300 |

```
gcgaaaatgg gttatctgac ggcgacagga aaaggaacca aacaaagttt tgtggaagct    360
atgaagtggt atcggtcagc tgctgagcat ggcaatatta atgttttctc agaaatagga    420
attatgtatg aggaggggta tggcgtcaaa aaaaacaaga accgtgctgt ccagtattac    480
attatgggag ctgataaagg aaatgccaaa gcgcagtatc ttttaggtca tgcctaccaa    540
tatggtcgtg gcatcaaaga tgatcctgaa cgggcgctgc actggtatcg taaagcggcg    600
gaacagggaa atgccgatgc cttgcaggca ctggggggta tttatgtaca tggcctgttg    660
aaccagaagg aagacaggga aaaggtgaaa aatatattg aagaggcgat tagaatccgc    720
aagcaaacgg gtcagctaga tccggctgcg atgaggcggt tgcggctttt gggcatcgat    780
atagagtga                                                           789
```

<210> SEQ ID NO 86
<211> LENGTH: 262
<212> TYPE: PRT
<213> ORGANISM: Oxalobacter formigenes

<400> SEQUENCE: 86

```
Met Arg Leu Phe Glu Ala Gly Lys Tyr Gln Gln Ala Met Thr Tyr Phe
1               5                   10                  15

Met Lys Glu Asp Ala Gln Lys Asn Pro Ala Val Ile Asn Arg Ile Gly
            20                  25                  30

Tyr Met Tyr Asp Tyr Gly Leu Gly Val Glu Lys Asn Arg Gln Ile Ser
        35                  40                  45

Phe Gln Trp Tyr Lys Lys Ala Gly Glu Met Gly Glu Ala Ala Ala Gln
    50                  55                  60

Phe Asn Val Gly Leu Phe Tyr Glu Lys Gly Tyr Gly Val Pro Gln Asp
65                  70                  75                  80

Ile Asn Met Ala Ile Glu Trp Phe Arg Lys Ser Ala Lys Gln Gln Tyr
                85                  90                  95

Pro Asn Ala Glu Ala Lys Met Gly Tyr Leu Thr Ala Thr Gly Lys Gly
            100                 105                 110

Thr Lys Gln Ser Phe Val Glu Ala Met Lys Trp Tyr Arg Ser Ala Ala
        115                 120                 125

Glu His Gly Asn Ile Asn Val Phe Ser Glu Ile Gly Ile Met Tyr Glu
    130                 135                 140

Glu Gly Tyr Gly Val Lys Lys Asn Lys Asn Arg Ala Val Gln Tyr Tyr
145                 150                 155                 160

Ile Met Gly Ala Asp Lys Gly Asn Ala Lys Ala Gln Tyr Leu Leu Gly
                165                 170                 175

His Ala Tyr Gln Tyr Gly Arg Gly Ile Lys Asp Asp Pro Glu Arg Ala
            180                 185                 190

Leu His Trp Tyr Arg Lys Ala Ala Glu Gln Gly Asn Ala Asp Ala Leu
        195                 200                 205

Gln Ala Leu Gly Gly Ile Tyr Val His Gly Leu Leu Asn Gln Lys Glu
    210                 215                 220

Asp Arg Glu Lys Gly Glu Lys Tyr Ile Glu Glu Ala Ile Arg Ile Arg
225                 230                 235                 240

Lys Gln Thr Gly Gln Leu Asp Pro Ala Ala Met Arg Arg Leu Arg Leu
                245                 250                 255

Leu Gly Ile Asp Ile Glu
            260
```

<210> SEQ ID NO 87

<211> LENGTH: 939
<212> TYPE: DNA
<213> ORGANISM: Oxalobacter formigenes

<400> SEQUENCE: 87

```
atgttaaaat acatcctgtt aattcagata gtatcaatta tgaaaaaatt tttattttat      60
tttttgtttt tatcaatttc attactgata atgtcaggat gtgacgataa aaatatactt     120
gatgaaaaag aaggtgttga atattataaa cagaaacaat atgaaaaagc gttacctcta     180
ttggaaaagt cggcttcatc aggtaattcc atcgcatctt attatttagg agagatgttt     240
tataaaggtg aaggagttga aaagaatgaa ataccggtt gtcaacgata tctggaatct      300
tcaaaagggg gcaataaaaa cgcttatttg gtgacggcca tctgttttta tacaggtagg     360
ggattggaaa agaatgatgc cgaagcattc aaatgggcga aaaagttga aaatgaaata      420
aatgaaacag gtcttggtga gtatgaccgg aaacattttt attttctaat gcagaatatc     480
tatttgtcag gaagaggtac tttgcaggat ttgagcgagg cagccaaatg gacagagaaa     540
atcgccaatt tgggtgatcc tgtctcacag ggtggtttag cggttttgta ctataatggc     600
aatggagttt tgaccgacag gaaaaaagcg cgttactggg cagaaaaagc ggccgcgcaa     660
ggcaatgata caggagaagt ggttcttggt atgttgaacc agtatagttt gcctcctgaa     720
caaaatttgg aaaaagcagc agaatggtat ttgaaatcag cagctcaggg aaataccgca     780
gcacaacatc agttggcggt tatgtatgaa aaggagaag gggttccgca agatttgaaa      840
aaagcccgtt attattatga agaagcggca aagagtaagt atgaagaacc caaaaaagcc     900
cttgaggaat tcaatgccac gtatcaaagt aaaaactaa                             939
```

<210> SEQ ID NO 88
<211> LENGTH: 312
<212> TYPE: PRT
<213> ORGANISM: Oxalobacter formigenes

<400> SEQUENCE: 88

```
Met Leu Lys Tyr Ile Leu Leu Ile Gln Ile Val Ser Ile Met Lys Lys
1               5                   10                  15

Phe Leu Phe Tyr Phe Leu Phe Leu Ser Ile Ser Leu Leu Ile Met Ser
            20                  25                  30

Gly Cys Asp Asp Lys Asn Ile Leu Asp Glu Lys Glu Gly Val Glu Tyr
        35                  40                  45

Tyr Lys Gln Lys Gln Tyr Glu Lys Ala Leu Pro Leu Leu Glu Lys Ser
    50                  55                  60

Ala Ser Ser Gly Asn Ser Ile Ala Ser Tyr Tyr Leu Gly Glu Met Phe
65                  70                  75                  80

Tyr Lys Gly Glu Gly Val Glu Lys Asn Glu Asn Thr Gly Cys Gln Arg
                85                  90                  95

Tyr Leu Glu Ser Ser Lys Gly Gly Asn Lys Asn Ala Tyr Leu Val Thr
            100                 105                 110

Ala Ile Cys Phe Tyr Thr Gly Arg Gly Leu Glu Lys Asn Asp Ala Glu
        115                 120                 125

Ala Phe Lys Trp Ala Lys Lys Val Glu Asn Glu Ile Asn Glu Thr Gly
    130                 135                 140

Leu Gly Glu Tyr Asp Arg Lys His Phe Tyr Phe Leu Met Gln Asn Ile
145                 150                 155                 160

Tyr Leu Ser Gly Arg Gly Thr Leu Gln Asp Leu Ser Glu Ala Ala Lys
                165                 170                 175
```

Trp Thr Glu Lys Ile Ala Asn Leu Gly Asp Pro Val Ser Gln Gly Gly
            180                 185                 190

Leu Ala Val Leu Tyr Tyr Asn Gly Asn Gly Val Leu Thr Asp Arg Lys
        195                 200                 205

Lys Ala Arg Tyr Trp Ala Glu Lys Ala Ala Gln Gly Asn Asp Thr
    210                 215                 220

Gly Glu Val Val Leu Gly Met Leu Asn Gln Tyr Ser Leu Pro Pro Glu
225                 230                 235                 240

Gln Asn Leu Glu Lys Ala Ala Glu Trp Tyr Leu Lys Ser Ala Ala Gln
                245                 250                 255

Gly Asn Thr Ala Ala Gln His Gln Leu Ala Val Met Tyr Glu Lys Gly
            260                 265                 270

Glu Gly Val Pro Gln Asp Leu Lys Lys Ala Arg Tyr Tyr Glu Glu
        275                 280                 285

Ala Ala Lys Ser Lys Tyr Glu Glu Pro Lys Lys Ala Leu Glu Glu Phe
    290                 295                 300

Asn Ala Thr Tyr Gln Ser Lys Asn
305                 310

<210> SEQ ID NO 89
<211> LENGTH: 1104
<212> TYPE: DNA
<213> ORGANISM: Oxalobacter formigenes

<400> SEQUENCE: 89

| | | | | |
|---|---|---|---|---|
| atgaaaaagt | ttattgtttc | agtgtttta | ttgggatggc | ttccgttata tgctgccggt | 60 |
| tcttctttgc | aggaaacaga | agaagtcgct | gtggcaaatg | aaatgagtga agccggttcg | 120 |
| gtcgatacag | atcgtttcaa | tgttccattg | caaaaagaaa | agaagcgcca gtcacctcgt | 180 |
| gaaaaacaaa | aaagagtgat | gaatacagag | aaaacaggta | ttgcgatcat cgcacccggc | 240 |
| ggttatgttc | cggattcgga | ccttcagcgg | gcaatcggtg | tgctgaagtc caggggatat | 300 |
| gaggttttca | attatgttga | tccccaaaaa | cgtcatgaac | gttttgcggc aaatgatgaa | 360 |
| gagcgaagcc | gtcagattat | ggaagcggca | acgaatccgg | atgtgaagat tgtgattgca | 420 |
| ttgcggggtg | gctacgggac | gacgcggctt | ttgcacgatc | ttgattttgc caaactggcc | 480 |
| aaaagcggaa | aactctttgt | cggtcacagc | gatttcacgg | ttttcgaaat ggcattgtta | 540 |
| aagcatggag | ccgtcagttt | ttccggcccg | atgattcaaa | gcgattttac gcgaggtgat | 600 |
| ctgagcgctt | ttaccttgaa | tcatttcgat | gaaaccatga | catcgccgga acatcggtc | 660 |
| aagtgggttt | ccaaagacaa | tcccgatgtc | gatgtcgagg | gaacgctgtg gggcggcaac | 720 |
| ctgacaatgc | tggctcatat | ggccgggact | ccctggatgc | cggacatttc cggtggcatt | 780 |
| ctgtttgtgg | aagacattca | cgaacatccc | tatcgcgtcg | agcgtatgct gctccagctg | 840 |
| gatgaatcag | gtatcctcaa | gaaacagaaa | gctctcgtgt | tgggacattt tccgaattc | 900 |
| aaactttccg | actacgataa | tggctacgat | ttcaacgcca | tgctttcctg gctccgttcg | 960 |
| cgtctgtcga | tacccgttgt | gaccggtttg | cctttcgggc | atacgaaaga caaagtcact | 1020 |
| ttgcctgtcg | ggggcagagc | gcatttgatg | tccaaggcag | gcaagattca actcgatatt | 1080 |
| ggggattatc | caacggtaag | gtaa | | | 1104 |

<210> SEQ ID NO 90
<211> LENGTH: 367
<212> TYPE: PRT
<213> ORGANISM: Oxalobacter formigenes

```
<400> SEQUENCE: 90

Met Lys Lys Phe Ile Val Ser Val Phe Leu Leu Gly Trp Leu Pro Leu
1               5                   10                  15

Tyr Ala Ala Gly Ser Ser Leu Gln Glu Thr Glu Val Ala Val Ala
            20                  25                  30

Asn Glu Met Ser Glu Ala Gly Ser Val Asp Thr Asp Arg Phe Asn Val
            35                  40                  45

Pro Leu Gln Lys Glu Lys Lys Arg Gln Ser Pro Arg Glu Lys Gln Lys
        50                  55                  60

Arg Val Met Asn Thr Glu Lys Thr Gly Ile Ala Ile Ala Pro Gly
65                  70                  75                  80

Gly Tyr Val Pro Asp Ser Asp Leu Gln Arg Ala Ile Gly Val Leu Lys
                85                  90                  95

Ser Arg Gly Tyr Glu Val Phe Asn Tyr Val Asp Pro Gln Lys Arg His
            100                 105                 110

Glu Arg Phe Ala Ala Asn Asp Glu Arg Ser Arg Gln Ile Met Glu
            115                 120                 125

Ala Ala Thr Asn Pro Asp Val Lys Ile Val Ile Ala Leu Arg Gly Gly
    130                 135                 140

Tyr Gly Thr Thr Arg Leu Leu His Asp Leu Asp Phe Ala Lys Leu Ala
145                 150                 155                 160

Lys Ser Gly Lys Leu Phe Val Gly His Ser Asp Phe Thr Val Phe Glu
                165                 170                 175

Met Ala Leu Leu Lys His Gly Ala Val Ser Phe Ser Gly Pro Met Ile
            180                 185                 190

Gln Ser Asp Phe Thr Arg Gly Asp Leu Ser Ala Phe Thr Leu Asn His
        195                 200                 205

Phe Asp Glu Thr Met Thr Ser Pro Glu Thr Ser Val Lys Trp Val Ser
210                 215                 220

Lys Asp Asn Pro Asp Val Asp Val Glu Gly Thr Leu Trp Gly Gly Asn
225                 230                 235                 240

Leu Thr Met Leu Ala His Met Ala Gly Thr Pro Trp Met Pro Asp Ile
                245                 250                 255

Ser Gly Gly Ile Leu Phe Val Glu Asp Ile His Glu His Pro Tyr Arg
            260                 265                 270

Val Glu Arg Met Leu Leu Gln Leu Asp Glu Ser Gly Ile Leu Lys Lys
        275                 280                 285

Gln Lys Ala Leu Val Leu Gly His Phe Ser Glu Phe Lys Leu Ser Asp
    290                 295                 300

Tyr Asp Asn Gly Tyr Asp Phe Asn Ala Met Leu Ser Trp Leu Arg Ser
305                 310                 315                 320

Arg Leu Ser Ile Pro Val Val Thr Gly Leu Pro Phe Gly His Thr Lys
                325                 330                 335

Asp Lys Val Thr Leu Pro Val Gly Gly Arg Ala His Leu Met Ser Lys
            340                 345                 350

Ala Gly Lys Ile Gln Leu Asp Ile Gly Asp Tyr Pro Thr Val Arg
            355                 360                 365

<210> SEQ ID NO 91
<211> LENGTH: 948
<212> TYPE: DNA
<213> ORGANISM: Oxalobacter formigenes

<400> SEQUENCE: 91
```

```
atgagtgaaa acggctggga acgtgaagtt ctcgaaaaac tgatgctgca aaccctgaaa    60
gagcaacggg cacgccgccg gtggggtatc tttttcaagc tgacgacgat cattctggtt   120
attttgtca ttttctcgat caagagcctt cttttttcca gcaaggaaac cgttcccgtc   180
cagaaacata cggcgatggt cgaaatccgc gggacgatcg attcctccgg caattcgtcg   240
gcagccaata tcatcaaggc gctggacaag gcctatgacg agccactggc aacaggcgtt   300
atcctgaaaa tcaacagccc gggcggaagc cctgttcagg caggcatgat ttatgatgaa   360
atccggcgtt tgcgtgaggt tcatcccgac aagcctcttt acgtcgtcgt tgaagaatta   420
tgcgcttccg gcggttatta tgttgccgca gcggcagaca agatctttgt cgacaaggcc   480
agtctggtcg gttccatcgg tgtcatgatc aacggtttcg gagtcaccgg cctgatgcag   540
aaactcggcg tcgagcgccg cctgttgacg gccgggaat acaagggttt ctctgacccg   600
ttttctcccc aaacgccaca gcaggtccag tatgcccaat ccatgctgaa ccagattcac   660
cagcaattca tcgaagttgt ccgtcagggc aggggcgaca ggctgaaaga aacagggaa   720
atctatagcg gtctggtttt tctcggtcct gaagcgatca aatgggggct ggctgacgaa   780
ctgggtacgg tcgaaagtgt tgcccgtgac gtgatcgggg aacctgtcat cgtcgattac   840
accgaacagg aaagactgtc tgaccgtttc ctgaagaaat tcggtgcctc cgtcggttat   900
ggagcggttc aggccggtct ggatatcaat cccgttccct gcattga              948
```

<210> SEQ ID NO 92
<211> LENGTH: 315
<212> TYPE: PRT
<213> ORGANISM: Oxalobacter formigenes
<400> SEQUENCE: 92

```
Met Ser Glu Asn Gly Trp Glu Arg Glu Val Leu Glu Lys Leu Met Leu
1               5                   10                  15

Gln Thr Leu Lys Glu Gln Arg Ala Arg Arg Trp Gly Ile Phe Phe
            20                  25                  30

Lys Leu Thr Thr Ile Ile Leu Val Ile Phe Val Ile Phe Ser Ile Lys
        35                  40                  45

Ser Leu Ser Phe Ser Ser Lys Glu Thr Val Pro Val Gln Lys His Thr
    50                  55                  60

Ala Met Val Glu Ile Arg Gly Thr Ile Asp Ser Ser Gly Asn Ser Ser
65                  70                  75                  80

Ala Ala Asn Ile Ile Lys Ala Leu Asp Lys Ala Tyr Asp Glu Pro Leu
                85                  90                  95

Ala Thr Gly Val Ile Leu Lys Ile Asn Ser Pro Gly Gly Ser Pro Val
            100                 105                 110

Gln Ala Gly Met Ile Tyr Asp Glu Ile Arg Arg Leu Arg Glu Val His
        115                 120                 125

Pro Asp Lys Pro Leu Tyr Val Val Glu Glu Leu Cys Ala Ser Gly
    130                 135                 140

Gly Tyr Tyr Val Ala Ala Ala Ala Asp Lys Ile Phe Val Asp Lys Ala
145                 150                 155                 160

Ser Leu Val Gly Ser Ile Gly Val Met Ile Asn Gly Phe Gly Val Thr
                165                 170                 175

Gly Leu Met Gln Lys Leu Gly Val Glu Arg Arg Leu Leu Thr Ala Gly
            180                 185                 190

Glu Tyr Lys Gly Phe Leu Asp Pro Phe Ser Pro Gln Thr Pro Gln Gln
        195                 200                 205
```

```
Val Gln Tyr Ala Gln Ser Met Leu Asn Gln Ile His Gln Gln Phe Ile
    210                 215                 220
Glu Val Val Arg Gln Gly Arg Gly Asp Arg Leu Lys Glu Asn Arg Glu
225                 230                 235                 240
Ile Tyr Ser Gly Leu Val Phe Leu Gly Pro Glu Ala Ile Lys Met Gly
                245                 250                 255
Leu Ala Asp Glu Leu Gly Thr Val Glu Ser Val Ala Arg Asp Val Ile
            260                 265                 270
Gly Glu Pro Val Ile Val Asp Tyr Thr Glu Gln Glu Arg Leu Ser Asp
        275                 280                 285
Arg Phe Leu Lys Lys Phe Gly Ala Ser Val Gly Tyr Gly Ala Val Gln
    290                 295                 300
Ala Gly Leu Asp Ile Asn Pro Val Pro Leu His
305                 310                 315
```

<210> SEQ ID NO 93
<211> LENGTH: 1638
<212> TYPE: DNA
<213> ORGANISM: Oxalobacter formigenes

<400> SEQUENCE: 93

```
atgaaaaccg atttgccagg caaaaacgcc ataccgaaga acagaatgac catcaaccgg    60
ctgtttgcct acacccggat tccccgcatc cggccagccc tgaccatggc cctgtgtgcc   120
gccaccctgg ccggttgcgc cgtcggcccc gattacgtcc agccgccaat cgacgtacct   180
gccacctaca aggaagacag cctctggaaa accgccaaac cctcggacga atacccgcgc   240
ggcgcatggt ggagcgtttt caaagaccct gaactcgacc gactgatggt tctcttaaac   300
aagcagaacc tgaccatcgc gcaggcagaa gcccagtacc ggcaggcgca ggccctgttg   360
cgacaggcac agtccagcct cttcccgagc ctgtcgctgg acgcctccag aacacgcggt   420
ttccagtcca ataccagcac ctcggccagt acgcaaaacg ccttcgtcgg caacctgtca   480
tgggaagtgg acatctgggg tggcgtccgc cgcaacgtcg aagcgggcga agccggacgg   540
caagccagtg ctgcccagct ggaagccatc aaactgtcgt cacaggcgca aatggccacg   600
gcctacctgc aactggtcat cactgaccgt caggtcaaac aactggaaga agcgaaaccc   660
ctgctggccg aatcgctccg gctgacgaaa aaccagtttg ccgtcggtat cgtctccgac   720
gccgatgtgc gcaggcgga aagccagctg aaaacggcac aggccgccac cgtcgacatg   780
aaactggcgc gcagccagct cgaacactca atccgcgtct ctatcggaca agccccgtcc   840
accttgacca tcgacatggc gaaagccgac ccctacctgc cgcaaatccc ggccgggctg   900
ccttcggccc tgctccagcg ccgtcctgac gtcgcttccg ccgaacgcaa ggtcgcgcag   960
gccaacgccc tgatcggcgt cgcgaaatcc gccttcttcc cggccctgtc catctcggcc  1020
tccggcggct tccgcaattc ctccttcgcc gacctgttca ccgtaccgaa ccgcatctgg  1080
tcgatcggcc gcaaatcgc cctgtccatc ttcgatgcag gctgcgcag cgcccagacc  1140
gatcaggcaa tcgccgtcta tgatgaaacc gtcgccgcct accgccagaa agtgctgatc  1200
gccttccagg aagtcgagga caacctcgcg gcacaagcca tgctcggcga cgcatccgac  1260
atgcaaacag ctgccctgaa tgcggcgaaa cgggccgaga ccatcaccat gaaccagtac  1320
aaggccggcg tcgtcagtta catcaacgtg ctgatcgccc agaacacccg catcgcagca  1380
gaaacacccc tgtacaacgt caaaaaacgc cagttcacca gcagcgtcgc cttaatcgcc  1440
gccattggcg ggcaatggga gacgccaaag caaacagcaa ataccggca cggcatcacc  1500
```

-continued

```
ggaaaaaatg gagcagaaaa cggaaatgaa aagttaggga cgttttgtta ccggatcaat    1560
gattcctcat tcgggactga ttcggtaact tatcgacaaa tattcaaatc tgacaaaaga    1620
gaaaatacat ggatatag                                                  1638
```

<210> SEQ ID NO 94
<211> LENGTH: 545
<212> TYPE: PRT
<213> ORGANISM: Oxalobacter formigenes

<400> SEQUENCE: 94

| Met | Lys | Thr | Asp | Leu | Pro | Gly | Lys | Asn | Ala | Ile | Pro | Lys | Asn | Arg | Met |
|---|---|---|---|---|---|---|---|---|---|---|---|---|---|---|---|
| 1 | | | | 5 | | | | | 10 | | | | | 15 | |

| Thr | Ile | Asn | Arg | Leu | Phe | Ala | Tyr | Thr | Arg | Ile | Pro | Arg | Ile | Arg | Pro |
| | | | 20 | | | | | 25 | | | | | 30 | | |

| Ala | Leu | Thr | Met | Ala | Leu | Cys | Ala | Ala | Thr | Leu | Ala | Gly | Cys | Ala | Val |
| | | | 35 | | | | | 40 | | | | | 45 | | |

| Gly | Pro | Asp | Tyr | Val | Gln | Pro | Pro | Ile | Asp | Val | Pro | Ala | Thr | Tyr | Lys |
| | 50 | | | | | 55 | | | | | 60 | | | | |

| Glu | Asp | Ser | Leu | Trp | Lys | Thr | Ala | Lys | Pro | Ser | Asp | Glu | Tyr | Pro | Arg |
| 65 | | | | | 70 | | | | | 75 | | | | | 80 |

| Gly | Ala | Trp | Trp | Ser | Val | Phe | Lys | Asp | Pro | Glu | Leu | Asp | Arg | Leu | Met |
| | | | | 85 | | | | | 90 | | | | | 95 | |

| Val | Leu | Leu | Asn | Lys | Gln | Asn | Leu | Thr | Ile | Ala | Gln | Ala | Glu | Ala | Gln |
| | | | 100 | | | | | 105 | | | | | 110 | | |

| Tyr | Arg | Gln | Ala | Gln | Ala | Leu | Leu | Arg | Gln | Ala | Gln | Ser | Ser | Leu | Phe |
| | | 115 | | | | | 120 | | | | | 125 | | | |

| Pro | Ser | Leu | Ser | Leu | Asp | Ala | Ser | Arg | Thr | Arg | Gly | Phe | Gln | Ser | Asn |
| | 130 | | | | | 135 | | | | | 140 | | | | |

| Thr | Ser | Thr | Ser | Ala | Ser | Thr | Gln | Asn | Ala | Phe | Val | Gly | Asn | Leu | Ser |
| 145 | | | | | 150 | | | | | 155 | | | | | 160 |

| Trp | Glu | Val | Asp | Ile | Trp | Gly | Gly | Val | Arg | Arg | Asn | Val | Glu | Ala | Gly |
| | | | | 165 | | | | | 170 | | | | | 175 | |

| Glu | Ala | Gly | Arg | Gln | Ala | Ser | Ala | Ala | Gln | Leu | Glu | Ala | Ile | Lys | Leu |
| | | | 180 | | | | | 185 | | | | | 190 | | |

| Ser | Ser | Gln | Ala | Gln | Met | Ala | Thr | Ala | Tyr | Leu | Gln | Leu | Val | Ile | Thr |
| | | 195 | | | | | 200 | | | | | 205 | | | |

| Asp | Arg | Gln | Val | Lys | Gln | Leu | Glu | Glu | Ser | Gly | Thr | Leu | Leu | Ala | Glu |
| 210 | | | | | 215 | | | | | 220 | | | | | |

| Ser | Leu | Arg | Leu | Thr | Lys | Asn | Gln | Phe | Ala | Val | Gly | Ile | Val | Ser | Asp |
| 225 | | | | | 230 | | | | | 235 | | | | | 240 |

| Ala | Asp | Val | Ala | Gln | Ala | Glu | Ser | Gln | Leu | Lys | Thr | Ala | Gln | Ala | Ala |
| | | | 245 | | | | | 250 | | | | | 255 | | |

| Thr | Val | Asp | Met | Lys | Leu | Ala | Arg | Ser | Gln | Leu | Glu | His | Ser | Ile | Ala |
| | | | 260 | | | | | 265 | | | | | 270 | | |

| Val | Ser | Ile | Gly | Gln | Ala | Pro | Ser | Thr | Leu | Thr | Ile | Asp | Met | Ala | Lys |
| | | 275 | | | | | 280 | | | | | 285 | | | |

| Ala | Asp | Pro | Tyr | Leu | Pro | Gln | Ile | Pro | Ala | Gly | Leu | Pro | Ser | Ala | Leu |
| | | 290 | | | | | 295 | | | | | 300 | | | |

| Leu | Gln | Arg | Arg | Pro | Asp | Val | Ala | Ser | Ala | Glu | Arg | Lys | Val | Ala | Gln |
| 305 | | | | | 310 | | | | | 315 | | | | | 320 |

| Ala | Asn | Ala | Leu | Ile | Gly | Val | Ala | Lys | Ser | Ala | Phe | Phe | Pro | Ala | Leu |
| | | | 325 | | | | | 330 | | | | | 335 | | |

| Ser | Ile | Ser | Ala | Ser | Gly | Gly | Phe | Arg | Asn | Ser | Ser | Phe | Ala | Asp | Leu |
| | | | 340 | | | | | 345 | | | | | 350 | | |

```
Phe Thr Val Pro Asn Arg Ile Trp Ser Ile Gly Pro Gln Ile Ala Leu
            355                 360                 365
Ser Ile Phe Asp Ala Gly Leu Arg Ser Ala Gln Thr Asp Gln Ala Ile
    370                 375                 380
Ala Val Tyr Asp Glu Thr Val Ala Ala Tyr Arg Gln Lys Val Leu Ile
385                 390                 395                 400
Ala Phe Gln Glu Val Glu Asp Asn Leu Ala Ala Gln Ala Met Leu Gly
                405                 410                 415
Asp Ala Ser Asp Met Gln Thr Ala Ala Leu Asn Ala Ala Lys Arg Ala
            420                 425                 430
Glu Thr Ile Thr Met Asn Gln Tyr Lys Ala Gly Val Val Ser Tyr Ile
        435                 440                 445
Asn Val Leu Ile Ala Gln Asn Thr Arg Ile Ala Ala Glu Asn Thr Leu
    450                 455                 460
Tyr Asn Val Lys Lys Arg Gln Phe Thr Ser Ser Val Ala Leu Ile Ala
465                 470                 475                 480
Ala Ile Gly Gly Gln Trp Glu Thr Pro Lys Gln Thr Ala Lys Tyr Arg
                485                 490                 495
His Gly Ile Thr Gly Lys Asn Gly Ala Glu Asn Gly Asn Glu Lys Leu
            500                 505                 510
Gly Thr Phe Cys Tyr Arg Ile Asn Asp Ser Ser Phe Gly Thr Asp Ser
        515                 520                 525
Val Thr Tyr Arg Gln Ile Phe Lys Ser Asp Lys Arg Glu Asn Thr Trp
    530                 535                 540
Ile
545

<210> SEQ ID NO 95
<211> LENGTH: 1476
<212> TYPE: DNA
<213> ORGANISM: Oxalobacter formigenes

<400> SEQUENCE: 95
atgaaagtca gaaggacaaa gaagatgatt aagaaattaa ccctcgtttt actggctgcc      60
ggtgtcttga gcagttgcag tatggcgccc aattacgtgc gaccggatgc cccgattgaa     120
agccagttcc cgggcaacgc ggatgacgct tctgcaaaaa cgcccgtgac gcaaatcgga     180
tggaatgaat ttttccatga accgcgattg aaagcgctga tcgctgccgc aattgaaaac     240
aatcgtgatt tgagagtagc agccttgcga attgaggaag cgcgtgccct gtatggcatc     300
cagtgggctg accgtctccc gaatttcgaa gctcagggag ccggaacccg tcaaagaacg     360
gtcggcacaa ccggcggcat ggtaacacag ggcaattaca ctgttggcct gggtctggct     420
gccttcgagc tggacttctt cggaagggtg aaaagcctgt cggacgctgc actggcagaa     480
tatctggcca cggaagaagc ccaacgtgcc gcctatatca gccttgtttc ggaagtggcc     540
aaaacctatc tgaccgaacg tgcacaagcg cgacagattg agttggcaaa gaatcctac      600 gagtcttaca acgcagcta tgagctgatg caaaagcgtt atgaagtcgg tgcatcttcc      660
gcactggaat tgcgtcagta tgaaacgctg atgcaatcgg cactggtttc gctctccacc      720
ctgcaaagac aacgcgccca gacagaaaac gcacttgtcg tactgattgg tggaaagcag     780
atcaaggatc ttcctgcggc gcacgacttg tcggaagacg acatcatgca ggacattccc     840
gccggattgc cgtccgatct gatcaacaac cggccggaca ttcgccagta tgaacaattg     900
ctcaagtcag cgaacgccaa tatcggcgca gccagagcag ccttttttccc gcgtattacc     960
```

```
ctgacaggtt tgccggaac agcaagcccg actttatccg ccttttcga tgccgggtcc    1020 ggtgcatgga catttatgcc gcaactgaca ctgccgattt tcgatgcagg ccgcaatatc    1080
agcaatctgg atctggcaga ggctcgcaag aatatcgcgg tggcccaata tgaaaaaacc    1140
gttcaggtcg ctttccgtga agtcgctgac gccctgatgg cacgcgactg gttgaatgaa    1200
caggtcaagg ctcaggctgc tgttctgaaa tcagagacgg aacgcctgaa actgtccgaa    1260
gcgcggtaca caacggtat tgccagttcg ctggaagtat tcgattcaca cgccagcaa    1320 tttgcggcac agcagtcgct ggttgacgca cgtctgttac gcctgatcaa tacagtggaa    1380
ctgtatcgtt cactgggtgg cggcatcgtc gatgccaatg cgccgaaaac agccaaaaca    1440
actgctgaac cggtagcgca aaatactgaa ggctga                              1476
```

<210> SEQ ID NO 96
<211> LENGTH: 491
<212> TYPE: PRT
<213> ORGANISM: Oxalobacter formigenes

<400> SEQUENCE: 96

```
Met Lys Val Arg Arg Thr Lys Lys Met Ile Lys Lys Leu Thr Leu Val
1               5                   10                  15

Leu Leu Ala Ala Gly Val Leu Ser Ser Cys Ser Met Ala Pro Asn Tyr
            20                  25                  30

Val Arg Pro Asp Ala Pro Ile Glu Ser Gln Phe Pro Gly Asn Ala Asp
        35                  40                  45

Asp Ala Ser Ala Lys Thr Pro Val Thr Gln Ile Gly Trp Asn Glu Phe
    50                  55                  60

Phe His Glu Pro Arg Leu Lys Ala Leu Ile Ala Ala Ile Glu Asn
65                  70                  75                  80

Asn Arg Asp Leu Arg Val Ala Ala Leu Arg Ile Glu Glu Ala Arg Ala
                85                  90                  95

Leu Tyr Gly Ile Gln Trp Ala Asp Arg Leu Pro Asn Phe Glu Ala Gln
            100                 105                 110

Gly Ala Gly Thr Arg Gln Arg Thr Val Gly Thr Thr Gly Gly Met Val
        115                 120                 125

Thr Gln Gly Asn Tyr Thr Val Gly Leu Gly Leu Ala Ala Phe Glu Leu
    130                 135                 140

Asp Phe Phe Gly Arg Val Lys Ser Leu Ser Asp Ala Ala Leu Ala Glu
145                 150                 155                 160

Tyr Leu Ala Thr Glu Glu Ala Gln Arg Ala Ala Tyr Ile Ser Leu Val
                165                 170                 175

Ser Glu Val Ala Lys Thr Tyr Leu Thr Glu Arg Ala Gln Ala Arg Gln
            180                 185                 190

Ile Glu Leu Ala Lys Glu Ser Tyr Glu Ser Tyr Lys Arg Ser Tyr Glu
        195                 200                 205

Leu Met Gln Lys Arg Tyr Glu Val Gly Ala Ser Ala Leu Glu Leu
    210                 215                 220

Arg Gln Tyr Glu Thr Leu Met Gln Ser Ala Leu Val Ser Leu Ser Thr
225                 230                 235                 240

Leu Gln Arg Gln Arg Ala Gln Thr Glu Asn Ala Leu Val Val Leu Ile
                245                 250                 255

Gly Gly Lys Gln Ile Lys Asp Leu Pro Ala Ala His Asp Leu Ser Glu
            260                 265                 270

Asp Asp Ile Met Gln Asp Ile Pro Ala Gly Leu Pro Ser Asp Leu Ile
```

```
                275                 280                 285
Asn Asn Arg Pro Asp Ile Arg Gln Tyr Glu Gln Leu Leu Lys Ser Ala
            290                 295                 300

Asn Ala Asn Ile Gly Ala Ala Arg Ala Ala Phe Phe Pro Arg Ile Thr
305                 310                 315                 320

Leu Thr Gly Phe Ala Gly Thr Ala Ser Pro Thr Leu Ser Gly Leu Phe
                325                 330                 335

Asp Ala Gly Ser Gly Ala Trp Thr Phe Met Pro Gln Leu Thr Leu Pro
            340                 345                 350

Ile Phe Asp Ala Gly Arg Asn Ile Ser Asn Leu Asp Leu Ala Glu Ala
                355                 360                 365

Arg Lys Asn Ile Ala Val Ala Gln Tyr Glu Lys Thr Val Gln Val Ala
            370                 375                 380

Phe Arg Glu Val Ala Asp Ala Leu Met Ala Arg Asp Trp Leu Asn Glu
385                 390                 395                 400

Gln Val Lys Ala Gln Ala Val Leu Lys Ser Glu Thr Glu Arg Leu
                405                 410                 415

Lys Leu Ser Glu Ala Arg Tyr Asn Asn Gly Ile Ala Ser Ser Leu Glu
            420                 425                 430

Val Phe Asp Ser Gln Arg Gln Phe Ala Ala Gln Gln Ser Leu Val
                435                 440                 445

Asp Ala Arg Leu Leu Arg Leu Ile Asn Thr Val Glu Leu Tyr Arg Ser
            450                 455                 460

Leu Gly Gly Gly Ile Val Asp Ala Asn Ala Pro Lys Thr Ala Lys Thr
465                 470                 475                 480

Thr Ala Glu Pro Val Ala Gln Asn Thr Glu Gly
                485                 490

<210> SEQ ID NO 97
<211> LENGTH: 602
<212> TYPE: DNA
<213> ORGANISM: Oxalobacter formigenes

<400> SEQUENCE: 97
taacgtgagg aacagatcac atcgacaagc cttgccgatt gtctttccat ctcgatcaga    60
aaactgtcga caagcgcccg gaaatgacga taaaaaacga gagtcggcat ggcaatcagc   120
aaaccgaagc cggtattgta aagcgccaca gaaatcccgt gagccagttc cgcaggattg   180 gccctccgg cattttgtga accgaaaatc tcgatcatcc cgacaaccgt accgaacagg    240
cccatcaggg gagccagcgt ggcaatcgtc ccgatcgtcg tcagaaagcg ttccatctgg   300
agagcgacac tgcggccggt ttcttccatc gcttccttca tattgtcgcg ggaaacatcg   360
gaatgctgca atccggtcgc cagcactgtc cccaaaggcg aaccctttc cagtttgtcg    420 attgtcgccg catccacacg accttcacga tactcacgta tgacctgatc cagaagatgt   480
ggcggcaaaa tctttcggcg tctcagataa atgagacgtt cgataatcag ggccaatgca   540
ataacagagg cgatcagcaa aaaccagatc ggccatcctg ccgcttgaat gattgaaaac   600
ac                                                                 602

<210> SEQ ID NO 98
<211> LENGTH: 659
<212> TYPE: DNA
<213> ORGANISM: Oxalobacter formigenes

<400> SEQUENCE: 98
```

```
tgtccaaaca acaatttaac ctgatcgttt tcgattggga cggcaccctg atggacagta    60
cgtccgccat cgtcaagagc cttcaggatt cggcagccga tctgggcttg cccacaccag   120
acaaaaagaa agcggcgcat gtgatcggcc tcggccttcg agaagcgctg gaaaccgtcc   180
tgccggacgt cagcccggaa tactatccga aactcatcga cgctatcgt acccatttcc    240 tgaaaaacag cgtatcgctt tccctgttcg acggtgtcag ggaaatgctc gacgacctga   300
agaatcagga ttattttctg gcagtggcca ccggaaaaag ccgggccggt ctgaaccgcg   360
ccatcgacga ggtgggcttg cagggatatt tcgatgccag ccgcacggct gatgaaacgc   420
attccaaacc tcatccggcc atgttgctgg aactgaccga acagttgggc gaaccgatga   480
aacgcacggt catgatcggt gataccaccc atgatttgct gatggcaaac aatgccggtg   540
cctcgggcat cgctgtacaa tacggtgcac attcacccaa agaactgcaa ttgatgcatc   600
cgatgtattc agccgatacg gtcgaagaac tgcatcgctg gctgaatgaa aatgcctga   659
```

<210> SEQ ID NO 99
<211> LENGTH: 2747
<212> TYPE: DNA
<213> ORGANISM: Oxalobacter formigenes

<400> SEQUENCE: 99

```
tatcgttcaa gccggttcga ttcaagcagt ttttcaaatt ccgccgctgt caggggttca    60
gagaaaagat atccctgacc ataattgcat ccggcaccgg ccaacaacaa tctctgtcca   120
tcgtcctgga caccttcggc aatcactttc atgtccagtt tgtgcgccat aacgataatc   180
gcctcacaca aggccatatc cttgggttca ttttcgatat ggcgaacgaa agcctgatcg   240
attttcagat agtcgatcgg aaattttttc agataagaca atgaagaata tcccgtcccg   300
aaatcgtcca gtgccacttc cattccatat tgatgaaatt ccgccagccg atcaagcacc   360
tgggtattcg aaacaatcaa aacaccttct gttatttcca tcacgatgct gctgccaggt   420
acattcagtt tttctagcac ttcgaaccag tcgctgtaat cattcttgtt ctggaacacg   480
ataggcgaga tattgaaact gatttgcaag tcagggaaga gatgttctct ccatcggctg   540
agctccctgg caacctcccc gaaagcccag tccgagatcg tcaaaatctg accggtttct   600
tccgcaatga aaatgaattc tgtgggactg ataatgccac gaaccggatg gtgccagcgg   660
atcagtgctt cggcttttctg gatgcggcca gtctcaatct cgacaatcgg ctgatacagc   720
atttcaaatt gatgttcatt tatagctata cgcatgtcat tggccagcct tatccggttt   780
tgcgcagccg cctgcatgga tgccgtaaag taactcatcc ggttacgtcc ggccagtttg   840
gcggcataca aggcctgatc ggcatttctc atgagtgtat cgatatccgt gccgtcatcc   900
ggataaaccg taatgccgat acttcctgtc acatacgcaa tttcgctacc caactggtaa   960
ggctgggcca gggaacgcag gatgctgtgc gcaattttt ccattgtcgg caaatcggac  1020
aactctgtca gaataatggc aaactcatcg ccacccagac gtgacacggt atcgaattca  1080
cggacgcaat ccttcagacg tttcgcgacg tccagtaaca ggtgatcgcc cgcatcgtgc  1140
ccaagggtat cgttgatatc cttgaaatta ccagatcga gaaacagcag cgccagtttt  1200
tttccggact ggttgacctt gactagtccc tgtttcatcc tgtccatcag catgcgacga  1260
ttcggcaaat tcgtcaggaa atcgaaattc gcctgacgcc atatcatgtc ttccgcttct  1320
tttttctccg tgaaatcatt ggagagttca acgtaataac gaacggatct gtcttcgttg  1380
taaaccacat tgattgtcag ccatgatgca tacgattcgc cattcttgcg ccggttccag  1440
agttccccac gccagtaccc tttctcatcc aatgcatccc acatcgcctt gtaaaatgcc  1500
```

```
ttgtcctggc gtcccgaact caacagtttc ggatccctgc cgatcacttc ggcagcggta    1560
tagcctgtaa ttttttcaaa ggccggattg actgcaagaa tatgattgtc ggcattactg    1620
atcaaaatcg cttcactgga gttacggtac accagtgctg ccagttccag ttttcctcg     1680 tcttcctttc ttcgcgtaat atcccgtccg attcccagaa cacccaccag ttcgccgtcc    1740
ggcgttctga caggtgcctt gatcacatcg aaaaacaccc tgttgccaga caatgcataa    1800
gtgccccact gcttgatcac cagtggtttg ccttccttca gaatacgttt gtcctgttct    1860
tcaaaaagct cggcttcgtc atggctgaat atatcgaaat cggttttacc gataatatgc    1920
tcgtcagaaa gcccgacata atccttgtaa gcctgattac aggccagata aacgcccgca    1980 gaattttttca tccataccag atcgggaata ttttcaaaaa cgcttttcag tcgcgcctcg    2040
ctttgggtca gaacgacatt gaccttgttc agatcgtccg ttctgatctc aaccagtttc    2100
tccagattga caagcaactg gttccggatt cctgcaagc ggaccataaa tagaatggcc     2160
aaaaagaaca cgccatgag gcgattgaa atcccgatga ctttggtgcc ccaataaaaa      2220
aggtctgcat tatatgcgcc cagcggcaaa agcgtgatga cttccatttt ataggcactg    2280
acatcacggg gaccctgtcc tccggaaaaa atttcgctac tgcctttact ggttttggta    2340
tcggccgaga gaggtgaaag cgttttgaac gtccataggc cttcccgggt aatgaactgg    2400
ccttcttcct gattttttcat ccgctcccag gcagcaggat atcgatgagc atactcaag    2460 tcattttttat tgaacatgaa tccgaattca tcgttggaaa ccggtccttt cagccagaat    2520
ccgttctgat tgacgagcca ggcagaattg ccacgcatgc tcgtcaactg ctggaaccgg    2580
ccgatcattg aagtggcata gtagttcaac agaagaatgc ccttttctc ccctttttg      2640 ttgaagagag gcatcccgaa acggatcgtc gggacataag gctcctggat atggtcatct    2700
tcaatattca ggtcaagagg tgaaacatag acttcccctt ctttcaa                  2747

<210> SEQ ID NO 100
<211> LENGTH: 659
<212> TYPE: DNA
<213> ORGANISM: Oxalobacter formigenes

<400> SEQUENCE: 100
tgtccaaaca acaatttaac ctgatcgttt tcgattggga cggcaccctg atggacagta      60
cgtccgccat cgtcaagagc cttcaggatt cggcagccga tctgggcttg cccacaccag     120
acaaaaagaa agcggcgcat gtgatcggcc tcggccttcg agaagcgctg gaaaccgtcc     180
tgccggacgt cagcccggaa tactatccga aactcatcga gcgctatcgt acccatttcc     240
tgaaaaacag cgtatcgctt tccctgttcg acggtgtcag ggaaatgctc gacgacctga     300
agaatcagga ttatttttctg gcagtggcca ccggaaaaag ccgggccggt ctgaaccgcg    360
ccatcgacga ggtgggcttg cagggatatt tcgatgccag ccgcacggct gatgaaacgc    420
attccaaacc tcatccggcc atgttgctgg aactgaccga acagtgggc gaaccgatga     480 aacgcacggt catgatcggt gataccaccc atgatttgct gatggcaaac aatgccggtg    540
cctcgggcat cgctgtacaa tacggtgcac attcacccaa agaactgcaa ttgatgcatc    600
cgatgtattc agccgatacg gtcgaagaac tgcatcgctg gctgaatgaa aatgcctga    659

<210> SEQ ID NO 101
<211> LENGTH: 190
<212> TYPE: PRT
<213> ORGANISM: Oxalobacter formigenes
```

```
<400> SEQUENCE: 101

Leu Ile Val Phe Asp Trp Asp Gly Thr Leu Met Asp Ser Thr Ser Ala
1               5                   10                  15

Ile Val Lys Ser Leu Gln Asp Ser Ala Ala Asp Leu Gly Leu Pro Thr
            20                  25                  30

Pro Asp Lys Lys Ala Ala His Val Ile Gly Leu Gly Leu Arg Glu
        35                  40                  45

Ala Leu Glu Thr Val Leu Pro Asp Val Ser Pro Glu Tyr Tyr Pro Lys
    50                  55                  60

Leu Ile Glu Arg Tyr Arg Thr His Phe Leu Lys Asn Ser Val Ser Leu
65                  70                  75                  80

Ser Leu Phe Asp Gly Val Arg Glu Met Leu Asp Asp Leu Lys Asn Gln
            85                  90                  95

Asp Tyr Phe Leu Ala Val Ala Thr Gly Lys Ser Arg Ala Gly Leu Asn
        100                 105                 110

Arg Ala Ile Asp Glu Val Gly Leu Gln Gly Tyr Phe Asp Ala Ser Arg
    115                 120                 125

Thr Ala Asp Glu Thr His Ser Lys Pro His Pro Ala Met Leu Leu Glu
130                 135                 140

Leu Thr Glu Gln Leu Gly Glu Pro Met Lys Arg Thr Val Met Ile Gly
145                 150                 155                 160

Asp Thr Thr His Asp Leu Leu Met Ala Asn Asn Ala Gly Ala Ser Gly
                165                 170                 175

Ile Ala Val Gln Tyr Gly Ala His Ser Pro Lys Glu Leu Gln
            180                 185                 190

<210> SEQ ID NO 102
<211> LENGTH: 112
<212> TYPE: PRT
<213> ORGANISM: Oxalobacter formigenes

<400> SEQUENCE: 102

Phe Glu Asn Ile Pro Asp Leu Val Trp Met Lys Asn Ser Ala Gly Val
1               5                   10                  15

Tyr Leu Ala Cys Asn Gln Ala Tyr Lys Asp Tyr Val Gly Leu Ser Asp
            20                  25                  30

Glu His Ile Ile Gly Lys Thr Asp Phe Asp Ile Phe Ser His Asp Glu
        35                  40                  45

Ala Glu Leu Phe Glu Glu Gln Asp Lys Arg Ile Leu Lys Glu Gly Lys
    50                  55                  60

Pro Leu Val Ile Lys Gln Trp Gly Thr Tyr Ala Leu Ser Gly Asn Arg
65                  70                  75                  80

Val Phe Phe Asp Val Ile Lys Ala Pro Val Arg Thr Pro Asp Gly Glu
            85                  90                  95

Leu Val Gly Val Leu Gly Ile Gly Arg Asp Ile Thr Arg Arg Lys Glu
        100                 105                 110

<210> SEQ ID NO 103
<211> LENGTH: 190
<212> TYPE: PRT
<213> ORGANISM: Oxalobacter formigenes

<400> SEQUENCE: 103

Lys Ala Ala Lys Ser Gly Asn Ala Glu Ala Gln Tyr Leu Phe Gly Met
1               5                   10                  15

Leu Val Tyr Asp Gly Arg Gly Val Gln Gln Asp Asn Cys Val Ala Met
```

```
            20                  25                  30
Leu Trp Trp Met Lys Ala Ala Glu Gln Asn His Ala Lys Ala Leu Val
         35                  40                  45

Met Leu Gly Asn Leu His Arg Lys Gly Gln Cys Ile Ala Glu Asn Tyr
 50                  55                  60

Pro Lys Ala Ile Ala Tyr Trp Lys Arg Ala Val Gln Asn Asn Val
 65                  70                  75                  80

Trp Ala Tyr His Asn Leu Gly Thr Ala Tyr Tyr Asp Gly Ile Gly Val
                 85                  90                  95

Asp Lys Asn Pro His Glu Ala Val Arg Trp Lys Lys Ala Ala Glu
                100                 105                 110

Leu Gly Phe Pro Glu Ser Gln Asn Asn Leu Gly Ala Leu Tyr Asn Asp
             115                 120                 125

Gly Asn Gly Val Asp Arg Asp Tyr Gln Glu Ala Val Phe Trp Tyr Arg
         130                 135                 140

Lys Ser Ala Leu Gln Gly Asp Glu Leu Gly Gln Tyr Asn Leu Gly Val
145                 150                 155                 160

Ala Tyr Tyr Gly Arg Gly Ile Lys Lys Asp Phe Ser Glu Ala Val
                165                 170                 175

Ser Trp Tyr Lys Lys Ser Ala Glu Gln Asp Tyr Ala Gln Ala
                180                 185                 190

<210> SEQ ID NO 104
<211> LENGTH: 249
<212> TYPE: PRT
<213> ORGANISM: Oxalobacter formigenes

<400> SEQUENCE: 104

Leu Gly Thr Ala Tyr Tyr Asp Gly Ile Gly Val Asp Lys Asn Pro His
 1               5                  10                  15

Glu Ala Val Arg Trp Trp Lys Lys Ala Ala Glu Leu Gly Phe Pro Glu
                 20                  25                  30

Ser Gln Asn Asn Leu Gly Ala Leu Tyr Asn Asp Gly Asn Gly Val Asp
             35                  40                  45

Arg Asp Tyr Gln Glu Ala Val Phe Trp Tyr Arg Lys Ser Ala Leu Gln
 50                  55                  60

Gly Asp Glu Leu Gly Gln Tyr Asn Leu Gly Val Ala Tyr Tyr Gly
 65                  70                  75                  80

Arg Gly Ile Lys Lys Asp Phe Ser Glu Ala Val Ser Trp Tyr Lys Lys
                 85                  90                  95

Ser Ala Glu Gln Asp Tyr Ala Gln Ala Gln His Asn Leu Gly Val Thr
                100                 105                 110

Tyr Tyr Glu Gly Glu Gly Ile Lys Lys Asp Tyr Ala Lys Ala Val Tyr
             115                 120                 125

Trp Trp Lys Lys Ala Ala Glu Gln Gly Ile Pro Gln Ser Gln Tyr Asn
         130                 135                 140

Leu Gly Ile Ala Tyr Glu Gly Gly Trp Gly Ala Glu Lys Asn Pro Glu
145                 150                 155                 160

Asn Ala Val Phe Trp Tyr Arg Lys Ala Ala Glu Gln Gly His Ala Asp
                165                 170                 175

Ala Gln Asn Arg Leu Gly Ile Ala Tyr Arg Tyr Gly Thr Gly Val Arg
             180                 185                 190

Lys Asn Pro Ala Leu Ser Val Lys Trp Leu Glu Lys Ala Ala Lys Gln
         195                 200                 205
```

-continued

```
Gly Leu Ala Arg Ala Gln Phe Asn Leu Gly Lys Thr Phe Tyr Ile Gly
    210                 215                 220

Ala Gly Ile Asn Lys Asn Thr Asp Lys Ala Val Tyr Trp Phe Ile Lys
225                 230                 235                 240

Ala Ala Asn Gln Gly Phe Thr Glu Ala
                245

<210> SEQ ID NO 105
<211> LENGTH: 172
<212> TYPE: PRT
<213> ORGANISM: Oxalobacter formigenes

<400> SEQUENCE: 105

Tyr Arg Lys Ala Ala Glu Gln Gly His Ala Asp Ala Gln Asn Arg Leu
1                5                  10                  15

Gly Ile Ala Tyr Arg Tyr Gly Thr Gly Val Arg Lys Asn Pro Ala Leu
            20                  25                  30

Ser Val Lys Trp Leu Glu Lys Ala Ala Lys Gln Gly Leu Ala Arg Ala
        35                  40                  45

Gln Phe Asn Leu Gly Lys Thr Phe Tyr Ile Gly Ala Gly Ile Asn Lys
    50                  55                  60

Asn Thr Asp Lys Ala Val Tyr Trp Phe Ile Lys Ala Ala Asn Gln Gly
65                  70                  75                  80

Phe Thr Glu Ala Gln Ala Tyr Ile Gly Met Ile Tyr Phe Lys Gly Lys
                85                  90                  95

Tyr Val Ala Lys Asn Glu Lys Lys Gly Phe Tyr Trp Leu Lys Lys Ala
            100                 105                 110

Ala Glu Lys Asp Ser Ala Lys Ala Gln Ala Phe Leu Gly Ala Leu Tyr
        115                 120                 125

Ile Ala Gly Asn Glu Val Lys Pro Asn Ile Lys Glu Gly Val Ala Leu
    130                 135                 140

Thr Lys Lys Ala Ala Leu Gln Gly Asn Tyr Glu Ala Gln Thr Leu Leu
145                 150                 155                 160

Gly Phe Cys Tyr Glu Asn Gly Leu Glu Val Lys Lys
                165                 170
```